US008715649B2

(12) United States Patent
Dinarello et al.

(10) Patent No.: US 8,715,649 B2
(45) Date of Patent: May 6, 2014

(54) COMPOSITIONS AND METHODS OF USE FOR ALPHA-1 ANTITRYPSIN HAVING NO SIGNIFICANT SERINE PROTEASE INHIBITOR ACTIVITY

(75) Inventors: Charles A. Dinarello, Boulder, CO (US); Eli C. Lewis, Be'er Sheva (IL)

(73) Assignee: The Regents of The University of Colorado, A Body Corporate

( * ) Notice: Subject to any disclaimer, the term of this patent is extended or adjusted under 35 U.S.C. 154(b) by 381 days.

(21) Appl. No.: 12/322,201

(22) Filed: Jan. 30, 2009

(65) Prior Publication Data

US 2009/0203580 A1 Aug. 13, 2009

Related U.S. Application Data

(63) Continuation-in-part of application No. 12/177,798, filed on Jul. 22, 2008, which is a continuation-in-part of application No. 11/916,521, filed as application No. PCT/US2006/022436 on Jun. 7, 2006, now abandoned, application No. 12/322,201, which is a continuation-in-part of application No. 12/106,052, filed on Apr. 18, 2008, now abandoned.

(60) Provisional application No. 60/687,850, filed on Jun. 7, 2005, provisional application No. 60/913,174, filed on Apr. 20, 2007.

(51) Int. Cl.
*A61K 38/48* (2006.01)
*A61K 39/00* (2006.01)
*A61K 45/00* (2006.01)
*A61K 47/00* (2006.01)
*C07H 21/04* (2006.01)

(52) U.S. Cl.
USPC ............. 424/94.64; 424/178.1; 424/192.1; 424/278.1; 435/810

(58) Field of Classification Search
None
See application file for complete search history.

(56) References Cited

U.S. PATENT DOCUMENTS

| | | | |
|---|---|---|---|
| 5,492,889 A | 2/1996 | Lezdey et al. | |
| 5,604,201 A * | 2/1997 | Thomas et al. | 514/2.4 |
| 6,022,855 A | 2/2000 | Thomas et al. | |
| 6,750,321 B1 * | 6/2004 | Chen et al. | 530/317 |
| 6,924,267 B2 | 8/2005 | Daemen et al. | |
| 7,304,033 B2 | 12/2007 | Larsen et al. | |
| 2003/0053998 A1 | 3/2003 | Daemen et al. | |

FOREIGN PATENT DOCUMENTS

| | | | |
|---|---|---|---|
| EP | 05111882 A2 | | 10/1992 |
| WO | WO 94/16073 A2 * | | 7/1994 |
| WO | WO02053092 A2 | | 7/2002 |

OTHER PUBLICATIONS

Merck Manual (16th Edition, Berkow, Ed. 1992, Rahway, NJ, Merck Research Laboratories).*
Courtney et al (Nature 1985, 313(10): 149-151).*
Paccani et al (J. Biol. Chem. 2002, 277(2): 1509-1513, abstract).*
Baecher-Allan and Hafler (Immunological Reviews 2006, 212:203-216).
Bell, J.J., et al., J. Immunol, 2008; 180:1508:1516.
(The Potomac Journal, 2010) Chaiet, P. pp. 1-7.
Dong, et al. (Ped/Transplant, 1999, 161:118-189).
Goodnow, C. (Lancet, 2001, 357:2115-2121).
Kraus and Mayer, (Curr. Opin. Gastroenterol, 2005, 21:692-696).
Lewis, et al. (PNAS USA Aug. 2005 102:12153-8, published online before print Aug. 10, 2005).
Lieberman, J., Augmentation therapy reduces frequency of lung infections in antitrypsin deficiency: a new hypothesis with supporting data, Chest, 2000, vol. 118, No. 5, p. 1480-5.
Marketletter, Sep. 13, 2009, 2 pages.
O'Riordan, et al. (Transplantation, 1997, 63(3): 1052-1055).
Panasyk and Mazur. "Disseminated pulmonary tuberculosis, diabetes mellitus and amyloidosis in a patient with hereditary alpha 1-antitrypsin deficiency," Probl. Tuberk, 1988, No. 1, p. 72-72.
Pozzilli, et al. (Diabetol, 2000, 43:1000-1004).
Rothe et al (J. Immunol, 1999, 163:1230-1236).
Schroeder, et al. (J. Surg. Sci. Res. 2003, 111:109-119).
Skyler, et al. (Diabetes Care, 2005, 28:1068-1076).
Song, et al. (Gene Therapy 2004, 11:181-186).
Strom (PNAS USA Aug. 2005 102: 12153-8, published online before print Aug. 29, 2005).
Yang, et al. (J. Am. Soc. Nephrol, 2003, 14:214-225).
International Search Report and Written Opinion of the International Searching Authority, PCT/US08/60848, Dec. 22, 2008.
Lomas, et al., "Preparation and Characterization of Latent alpha-1 antitrypsin." Journal of Biological Chemistry, 270, pp. 5282-5288, Mar. 10, 1995.
Anderson, Inhibition of HIV-1 gp 160-dependent Membrane Fusion by a Furin-directed Alpha 1-Antitrypsin Variant, The Journal of Biological Chemistry, vol. 268, No. 33 (Nov. 25, 1993), pp. 24887-24891.
Gettins, Serpin Structure, Mechanism, and Function, American Chemical Society, vol. 102, (Nov. 8, 2002) pp. 4751-4803.
Kirani, Co-Existence of Pulmonary Tuberculosis and Diabetes Mellitus: Some Observations, Ind. J. Tub, No. 164, pp. 47-48 (1998).
Lewis, Antithrombin Pittsburgh: An Alpha 1-Antitrypsin Variant Causing Hemorrhagic Disease, Blood Journal, vol. 51, No. 1 (Jan. 1978) pp. 129-137.
Palomino, New Anti-Tuberculosis Drugs: Strategies, Sources and New Molecules, Current Medicinal Chemistry, vol. 16, (2009) pp. 1898-1904.

* cited by examiner

*Primary Examiner* — Gerald R Ewoldt
*Assistant Examiner* — Marianne DiBrino
(74) *Attorney, Agent, or Firm* — Faegre Baker Daniels LLP

(57) ABSTRACT

Embodiments herein illustrate methods and compositions for treating medical disorders. In certain embodiments, compositions and methods relate to reducing, inhibiting or treating graft rejection, transplant rejection or diabetes in a subject. Other embodiments herein relate to compounds including naturally occurring and synthetic mutant compositions of alpha-1 antitrypsin, wherein the alpha-1 antitrypsin has no significant serine protease inhibitor activity.

10 Claims, 56 Drawing Sheets

C

D

G

H

A

B

C

D

Figs. 6A-6C
A
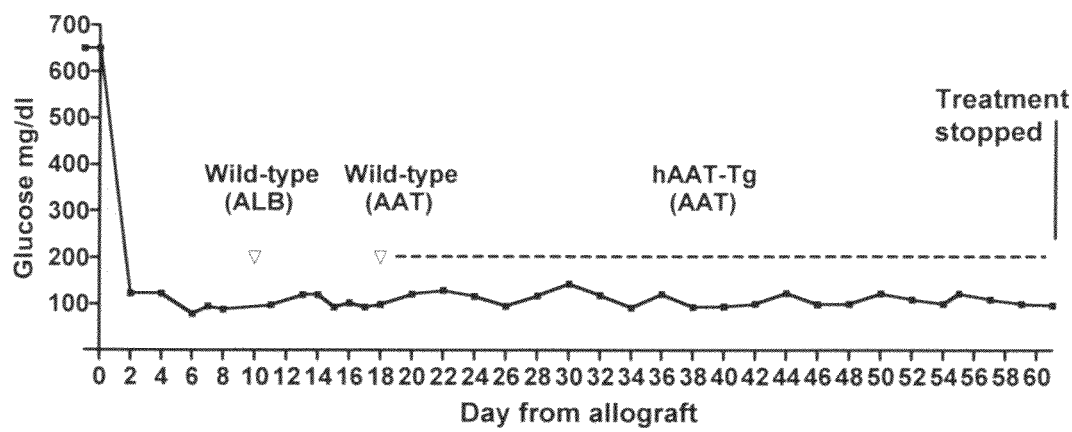
B
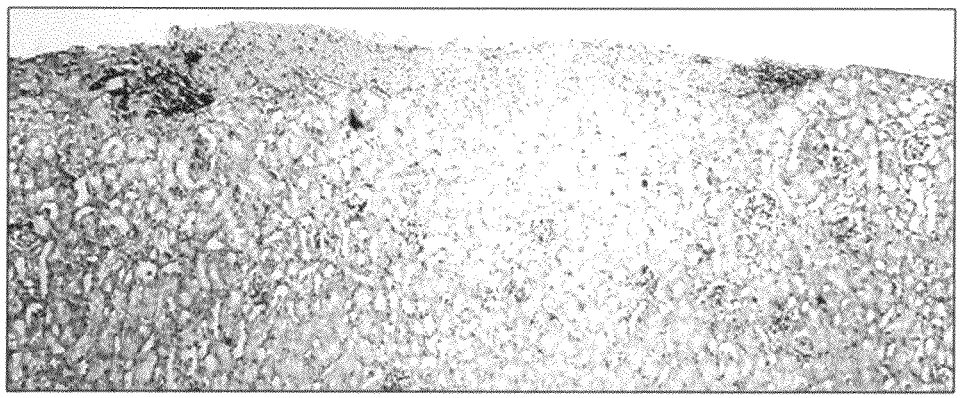
C
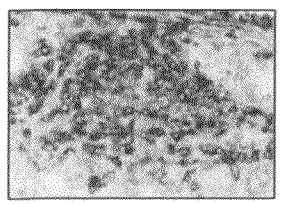
CD4
(Lymphocytes)
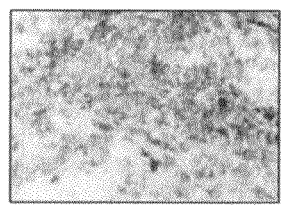
CD11b
(Monocytes/PMN)

C

D

C

D

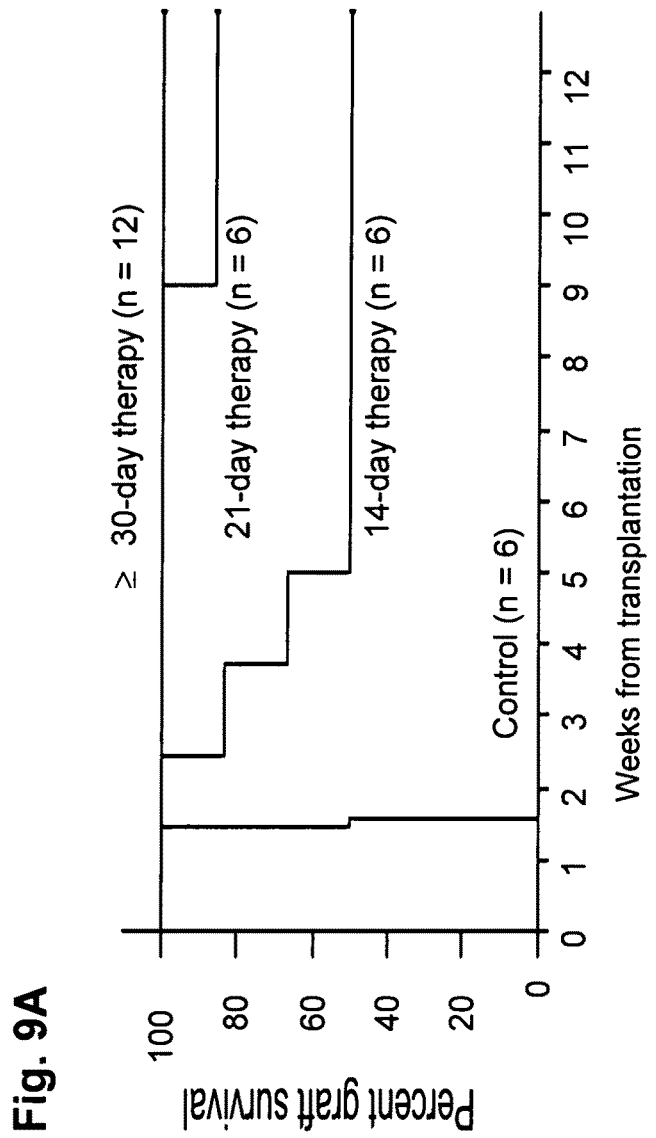

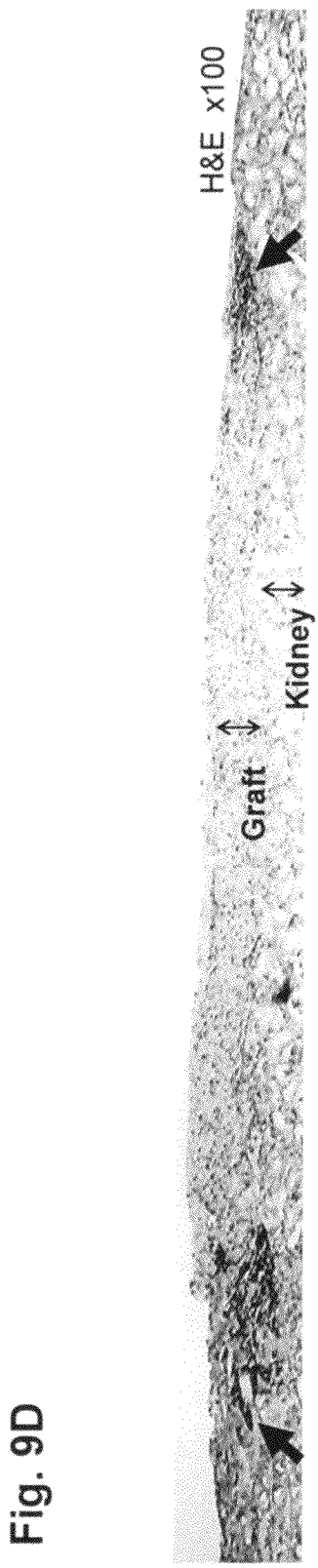

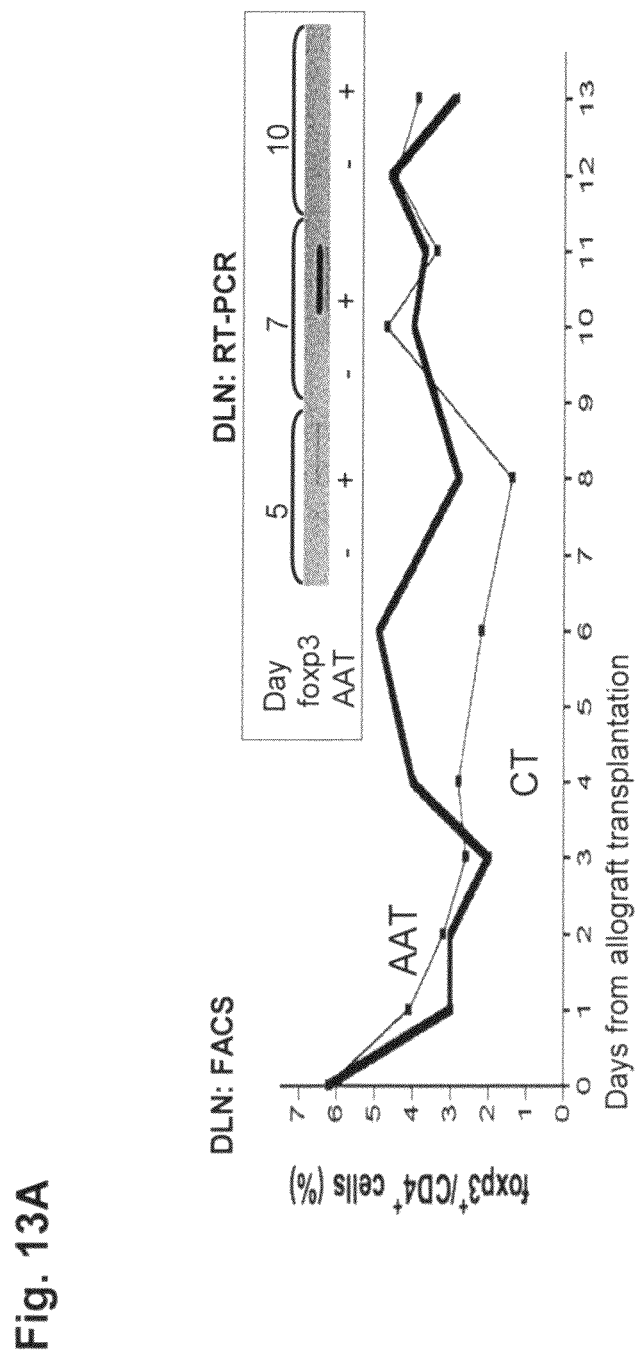

Fig. 31

| Reactive centre: engineered and natural variants | | | | | | | | | | | |
|---|---|---|---|---|---|---|---|---|---|---|---|
| Serpin | P4 | P3 | P2 | P1 | P1' | P2' | P3' | P4' | P5' | Inhibits | SEQ ID NO. | Oxidation |
| α1-Antitrypsin | Ala | Ile | Pro | Met | Ser | Ile | Pro | Pro | Glu | elastase | 104 | + |
| Pittsburgh variant | Ala | Ile | Pro | Arg | Ser | Ile | Pro | Pro | Glu | thrombin | 105 | − |
| Val-recombinant | Ala | Ile | Pro | Val | Ser | Ile | Pro | Pro | Glu | elastase | 106 | − |
| Leu-recombinant | Ala | Ile | Pro | Leu | Ser | Ile | Pro | Pro | Glu | Cat G. elastase | 107 | − |
| P2Cys-recombinant | Ala | Ile | Cys | Met | Ser | Ile | Pro | Pro | Glu | non-functional | 108 | |
| Ala-recombinant | Ala | Ile | Pro | Ala | Ser | Ile | Pro | Pro | Glu | elastase | 109 | − |
| Christchurch variant | Ala | Ile | Pro | Met | Ser | Ile | Pro | Pro | Lys | elastase | 110 | + |
| P3-P3'-recombinant | Ala | Ala | Gly | Arg | Ser | Leu | Asn | Pro | Glu | non-functional | 111 | |
| Antithrombin | Ile | Ala | Gly | Arg | Ser | Leu | Asn | Pro | Asn | thrombin | 112 | − |
| Denver variant* | Ile | Ala | Gly | Arg | Leu | Leu | Asn | Pro | Asn | non-functional | 113 | − |

Stephens, Thalley and Hirs (1985).

Fig. 36

```
                          Proline
pEF-AAT    →  TTTAGAGGCCATATACCCATGTCTATCCCCCCGAGGTCAAGTTCAACAAACCCTTTGTCTT
              ||||||||||||||||   |||||||||||||||||||||||||||||||||||||||||
pEF-AATcys →  TTTAGAGGCCATATATGCATGTCTATCCCCCCGAGGTCAAGTTCAACAAACCCTTTGTCTT
                          Cysteine
```

Sequence verification of mutated plasmid. Sequence analysis confirms an intact reactive center loop sequence outside a mutated amino acid site.

```
                        SEQUENCE LISTING

<160> NUMBER OF SEQ ID NOS: 113

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Phe Val Phe Leu Met
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Phe Val Phe Ala Met
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Phe Val Ala Leu Met
1               5

<210> SEQ ID NO 4
<211> LENGTH: 5
<212> TYPE: PRT
<213> ORGANISM: Artificial
<220> FEATURE:
<223> OTHER INFORMATION: synthetic peptide

<400> SEQUENCE: 4

Phe Val Phe Leu Ala
1               5

<210> SEQ ID NO 5
<211> LENGTH: 5
<212> TYPE: PRT
<213> ORGANISM: Artificial
<220> FEATURE:
<223> OTHER INFORMATION: synthetic peptide

<400> SEQUENCE: 5

Phe Leu Val Phe Ile
1               5

<210> SEQ ID NO 6
<211> LENGTH: 5
<212> TYPE: PRT
```

```
<213> ORGANISM: Artificial
<220> FEATURE:
<223> OTHER INFORMATION: synthetic peptide

<400> SEQUENCE: 6

Phe Leu Met Ile Ile
1               5

<210> SEQ ID NO 7
<211> LENGTH: 5
<212> TYPE: PRT
<213> ORGANISM: Artificial
<220> FEATURE:
<223> OTHER INFORMATION: synthetic peptide

<400> SEQUENCE: 7

Phe Leu Phe Val Leu
1               5

<210> SEQ ID NO 8
<211> LENGTH: 5
<212> TYPE: PRT
<213> ORGANISM: Artificial
<220> FEATURE:
<223> OTHER INFORMATION: synthetic peptide

<400> SEQUENCE: 8

Phe Leu Phe Val Val
1               5

<210> SEQ ID NO 9
<211> LENGTH: 5
<212> TYPE: PRT
<213> ORGANISM: Artificial
<220> FEATURE:
<223> OTHER INFORMATION: synthetic peptide

<400> SEQUENCE: 9

Phe Leu Phe Leu Ile
1               5

<210> SEQ ID NO 10
<211> LENGTH: 5
<212> TYPE: PRT
<213> ORGANISM: Artificial
<220> FEATURE:
<223> OTHER INFORMATION: synthetic peptide

<400> SEQUENCE: 10

Phe Leu Phe Phe Ile
1               5

<210> SEQ ID NO 11
<211> LENGTH: 5
<212> TYPE: PRT
<213> ORGANISM: Artificial
<220> FEATURE:
<223> OTHER INFORMATION: synthetic peptide

<400> SEQUENCE: 11

Phe Leu Met Phe Ile
1               5

<210> SEQ ID NO 12
<211> LENGTH: 5
<212> TYPE: PRT
<213> ORGANISM: Artificial
<220> FEATURE:
```

<223> OTHER INFORMATION: synthetic peptide

<400> SEQUENCE: 12

Phe Met Leu Leu Ile
1               5

<210> SEQ ID NO 13
<211> LENGTH: 5
<212> TYPE: PRT
<213> ORGANISM: Artificial
<220> FEATURE:
<223> OTHER INFORMATION: synthetic peptide

<400> SEQUENCE: 13

Phe Ile Ile Met Ile
1               5

<210> SEQ ID NO 14
<211> LENGTH: 5
<212> TYPE: PRT
<213> ORGANISM: Artificial
<220> FEATURE:
<223> OTHER INFORMATION: synthetic peptide

<400> SEQUENCE: 14

Phe Leu Phe Cys Ile
1               5

<210> SEQ ID NO 15
<211> LENGTH: 5
<212> TYPE: PRT
<213> ORGANISM: Artificial
<220> FEATURE:
<223> OTHER INFORMATION: synthetic peptide

<400> SEQUENCE: 15

Phe Leu Phe Ala Val
1               5

<210> SEQ ID NO 16
<211> LENGTH: 5
<212> TYPE: PRT
<213> ORGANISM: Artificial
<220> FEATURE:
<223> OTHER INFORMATION: synthetic peptide

<400> SEQUENCE: 16

Phe Val Tyr Leu Ile
1               5

<210> SEQ ID NO 17
<211> LENGTH: 5
<212> TYPE: PRT
<213> ORGANISM: Artificial
<220> FEATURE:
<223> OTHER INFORMATION: synthetic peptide

<400> SEQUENCE: 17

Phe Ala Phe Leu Met
1               5

<210> SEQ ID NO 18
<211> LENGTH: 5
<212> TYPE: PRT
<213> ORGANISM: Artificial
<220> FEATURE:
<223> OTHER INFORMATION: synthetic peptide

```
<400> SEQUENCE: 18

Ala Val Phe Leu Met
1               5

<210> SEQ ID NO 19
<211> LENGTH: 10
<212> TYPE: PRT
<213> ORGANISM: Homo sapiens

<400> SEQUENCE: 19

Met Pro Ser Ser Val Ser Trp Gly Ile Leu
1               5                   10

<210> SEQ ID NO 20
<211> LENGTH: 10
<212> TYPE: PRT
<213> ORGANISM: Homo sapiens

<400> SEQUENCE: 20

Leu Leu Ala Gly Leu Cys Cys Leu Val Pro
1               5                   10

<210> SEQ ID NO 21
<211> LENGTH: 10
<212> TYPE: PRT
<213> ORGANISM: Homo sapiens

<400> SEQUENCE: 21

Val Ser Leu Ala Glu Asp Pro Gln Gly Asp
1               5                   10

<210> SEQ ID NO 22
<211> LENGTH: 10
<212> TYPE: PRT
<213> ORGANISM: Homo sapiens

<400> SEQUENCE: 22

Ala Ala Gln Lys Thr Asp Thr Ser His His
1               5                   10

<210> SEQ ID NO 23
<211> LENGTH: 10
<212> TYPE: PRT
<213> ORGANISM: Homo sapiens

<400> SEQUENCE: 23

Asp Gln Asp His Pro Thr Phe Asn Lys Ile
1               5                   10

<210> SEQ ID NO 24
<211> LENGTH: 10
<212> TYPE: PRT
<213> ORGANISM: Homo sapiens

<400> SEQUENCE: 24

Thr Pro Asn Leu Ala Glu Phe Ala Phe Ser
1               5                   10

<210> SEQ ID NO 25
<211> LENGTH: 10
<212> TYPE: PRT
<213> ORGANISM: Homo sapiens

<400> SEQUENCE: 25

Leu Tyr Arg Gln Leu Ala His Gln Ser Asn
```

-continued

```
<210> SEQ ID NO 26
<211> LENGTH: 10
<212> TYPE: PRT
<213> ORGANISM: Homo sapiens

<400> SEQUENCE: 26

Ser Thr Asn Ile Phe Phe Ser Pro Val Ser
1               5                   10

<210> SEQ ID NO 27
<211> LENGTH: 10
<212> TYPE: PRT
<213> ORGANISM: Homo sapiens

<400> SEQUENCE: 27

Ile Ala Thr Ala Phe Ala Met Leu Ser Leu
1               5                   10

<210> SEQ ID NO 28
<211> LENGTH: 10
<212> TYPE: PRT
<213> ORGANISM: Homo sapiens

<400> SEQUENCE: 28

Gly Thr Lys Ala Asp Thr His Asp Glu Ile
1               5                   10

<210> SEQ ID NO 29
<211> LENGTH: 10
<212> TYPE: PRT
<213> ORGANISM: Homo sapiens

<400> SEQUENCE: 29

Leu Glu Gly Leu Asn Phe Asn Leu Thr Glu
1               5                   10

<210> SEQ ID NO 30
<211> LENGTH: 10
<212> TYPE: PRT
<213> ORGANISM: Homo sapiens

<400> SEQUENCE: 30

Ile Pro Glu Ala Gln Ile His Glu Gly Phe
1               5                   10

<210> SEQ ID NO 31
<211> LENGTH: 10
<212> TYPE: PRT
<213> ORGANISM: Homo sapiens

<400> SEQUENCE: 31

Gln Glu Leu Leu Arg Thr Leu Asn Gln Pro
1               5                   10

<210> SEQ ID NO 32
<211> LENGTH: 10
<212> TYPE: PRT
<213> ORGANISM: Homo sapiens

<400> SEQUENCE: 32

Asp Ser Gln Leu Gln Leu Thr Thr Gly Asn
1               5                   10
```

```
<210> SEQ ID NO 33
<211> LENGTH: 10
<212> TYPE: PRT
<213> ORGANISM: Homo sapiens

<400> SEQUENCE: 33

Gly Leu Phe Leu Ser Glu Gly Leu Lys Leu
1               5                   10

<210> SEQ ID NO 34
<211> LENGTH: 10
<212> TYPE: PRT
<213> ORGANISM: Homo sapiens

<400> SEQUENCE: 34

Val Asp Lys Phe Leu Glu Asp Val Lys Lys
1               5                   10

<210> SEQ ID NO 35
<211> LENGTH: 10
<212> TYPE: PRT
<213> ORGANISM: Homo sapiens

<400> SEQUENCE: 35

Leu Tyr His Ser Glu Ala Phe Thr Val Asn
1               5                   10

<210> SEQ ID NO 36
<211> LENGTH: 10
<212> TYPE: PRT
<213> ORGANISM: Homo sapiens

<400> SEQUENCE: 36

Phe Gly Asp Thr Glu Glu Ala Lys Lys Gln
1               5                   10

<210> SEQ ID NO 37
<211> LENGTH: 10
<212> TYPE: PRT
<213> ORGANISM: Homo sapiens

<400> SEQUENCE: 37

Ile Asn Asp Tyr Val Glu Lys Gly Thr Gln
1               5                   10

<210> SEQ ID NO 38
<211> LENGTH: 10
<212> TYPE: PRT
<213> ORGANISM: Homo sapiens

<400> SEQUENCE: 38

Gly Lys Ile Val Asp Leu Val Lys Glu Leu
1               5                   10

<210> SEQ ID NO 39
<211> LENGTH: 10
<212> TYPE: PRT
<213> ORGANISM: Homo sapiens

<400> SEQUENCE: 39

Asp Arg Asp Thr Val Phe Ala Leu Val Asn
1               5                   10

<210> SEQ ID NO 40
<211> LENGTH: 10
<212> TYPE: PRT
```

<213> ORGANISM: Homo sapiens

<400> SEQUENCE: 40

Tyr Ile Phe Phe Lys Gly Lys Trp Glu Arg
1               5                   10

<210> SEQ ID NO 41
<211> LENGTH: 10
<212> TYPE: PRT
<213> ORGANISM: Homo sapiens

<400> SEQUENCE: 41

Pro Phe Glu Val Lys Asp Thr Glu Glu Glu
1               5                   10

<210> SEQ ID NO 42
<211> LENGTH: 10
<212> TYPE: PRT
<213> ORGANISM: Homo sapiens

<400> SEQUENCE: 42

Asp Phe His Val Asp Gln Val Thr Thr Val
1               5                   10

<210> SEQ ID NO 43
<211> LENGTH: 10
<212> TYPE: PRT
<213> ORGANISM: Homo sapiens

<400> SEQUENCE: 43

Lys Val Pro Met Met Lys Arg Leu Gly Met
1               5                   10

<210> SEQ ID NO 44
<211> LENGTH: 10
<212> TYPE: PRT
<213> ORGANISM: Homo sapiens

<400> SEQUENCE: 44

Phe Asn Ile Gln His Cys Lys Lys Leu Ser
1               5                   10

<210> SEQ ID NO 45
<211> LENGTH: 10
<212> TYPE: PRT
<213> ORGANISM: Homo sapiens

<400> SEQUENCE: 45

Ser Trp Val Leu Leu Met Lys Tyr Leu Gly
1               5                   10

<210> SEQ ID NO 46
<211> LENGTH: 10
<212> TYPE: PRT
<213> ORGANISM: Homo sapiens

<400> SEQUENCE: 46

Asn Ala Thr Ala Ile Phe Phe Leu Pro Asp
1               5                   10

<210> SEQ ID NO 47
<211> LENGTH: 10
<212> TYPE: PRT
<213> ORGANISM: Homo sapiens

<400> SEQUENCE: 47

Glu Gly Lys Leu Gln His Leu Glu Asn Glu
1               5                   10

<210> SEQ ID NO 48
<211> LENGTH: 10
<212> TYPE: PRT
<213> ORGANISM: Homo sapiens

<400> SEQUENCE: 48

Leu Thr His Asp Ile Ile Thr Lys Phe Leu
1               5                   10

<210> SEQ ID NO 49
<211> LENGTH: 10
<212> TYPE: PRT
<213> ORGANISM: Homo sapiens

<400> SEQUENCE: 49

Glu Asn Glu Asp Arg Arg Ser Ala Ser Leu
1               5                   10

<210> SEQ ID NO 50
<211> LENGTH: 10
<212> TYPE: PRT
<213> ORGANISM: Homo sapiens

<400> SEQUENCE: 50

His Leu Pro Lys Leu Ser Ile Thr Gly Thr
1               5                   10

<210> SEQ ID NO 51
<211> LENGTH: 10
<212> TYPE: PRT
<213> ORGANISM: Homo sapiens

<400> SEQUENCE: 51

Tyr Asp Leu Lys Ser Val Leu Gly Gln Leu
1               5                   10

<210> SEQ ID NO 52
<211> LENGTH: 10
<212> TYPE: PRT
<213> ORGANISM: Homo sapiens

<400> SEQUENCE: 52

Gly Ile Thr Lys Val Phe Ser Asn Gly Ala
1               5                   10

<210> SEQ ID NO 53
<211> LENGTH: 10
<212> TYPE: PRT
<213> ORGANISM: Homo sapiens

<400> SEQUENCE: 53

Asp Leu Ser Gly Val Thr Glu Glu Ala Pro
1               5                   10

<210> SEQ ID NO 54
<211> LENGTH: 10
<212> TYPE: PRT
<213> ORGANISM: Homo sapiens

<400> SEQUENCE: 54

Leu Lys Leu Ser Lys Ala Val His Lys Ala
1               5                   10

<210> SEQ ID NO 55
<211> LENGTH: 10
<212> TYPE: PRT
<213> ORGANISM: Homo sapiens

<400> SEQUENCE: 55

Val Leu Thr Ile Asp Glu Lys Gly Thr Glu
1               5                   10

<210> SEQ ID NO 56
<211> LENGTH: 10
<212> TYPE: PRT
<213> ORGANISM: Homo sapiens

<400> SEQUENCE: 56

Ala Ala Gly Ala Met Phe Leu Glu Ala Ile
1               5                   10

<210> SEQ ID NO 57
<211> LENGTH: 10
<212> TYPE: PRT
<213> ORGANISM: Homo sapiens

<400> SEQUENCE: 57

Pro Met Ser Ile Pro Pro Glu Val Lys Phe
1               5                   10

<210> SEQ ID NO 58
<211> LENGTH: 10
<212> TYPE: PRT
<213> ORGANISM: Homo sapiens

<400> SEQUENCE: 58

Asn Lys Pro Phe Val Phe Leu Met Ile Glu
1               5                   10

<210> SEQ ID NO 59
<211> LENGTH: 10
<212> TYPE: PRT
<213> ORGANISM: Homo sapiens

<400> SEQUENCE: 59

Gln Asn Thr Lys Ser Pro Leu Phe Met Gly
1               5                   10

<210> SEQ ID NO 60
<211> LENGTH: 8
<212> TYPE: PRT
<213> ORGANISM: Homo sapiens

<400> SEQUENCE: 60

Lys Val Val Asn Pro Thr Gln Lys
1               5

<210> SEQ ID NO 61
<211> LENGTH: 394
<212> TYPE: PRT
<213> ORGANISM: Homo sapiens

<400> SEQUENCE: 61

Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
             35                  40                  45

Asn Ile Phe Phe Ser Pro Val Ser Ile Ala Thr Ala Phe Ala Met Leu
 50                  55                  60

Ser Leu Gly Thr Lys Ala Asp Thr His Asp Glu Ile Leu Glu Gly Leu
 65                  70                  75                  80

Asn Phe Asn Leu Thr Glu Ile Pro Gly Ala Gln Ile His Glu Gly Phe
                 85                  90                  95

Gln Glu Leu Leu Arg Thr Leu Asn Gln Pro Asp Ser Gln Leu Gln Leu
                100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
            130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
            210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
            275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
            355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
actcctccgt accctcaacc                                              20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
gcattgccca ggtatttcat                                              20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
actgtcaact tcggggacac                                              20

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
catgcctaaa cgcttcatca                                              20

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
ctccatgagc tttgtacaag g                                            21

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
tgctgatgta ccagttgggg                                              20

<210> SEQ ID NO 68
<211> LENGTH: 24
<212> TYPE: DNA
<213> ORGANISM: Artificial Sequence
<220> FEATURE:
<223> OTHER INFORMATION: primer

<400> SEQUENCE: 68
catttgcatc ctcctggttt ctga                                         24

<210> SEQ ID NO 69
<211> LENGTH: 24
<212> TYPE: DNA
<213> ORGANISM: Artificial Sequence
<220> FEATURE:

<223> OTHER INFORMATION: primer

<400> SEQUENCE: 69
gagtgagttt tccccttccg tgtg                                              24

<210> SEQ ID NO 70
<211> LENGTH: 32
<212> TYPE: DNA
<213> ORGANISM: Artificial Sequence
<220> FEATURE:
<223> OTHER INFORMATION: primer

<400> SEQUENCE: 70
ttcaagctcc acttcaagct ctacagcgga ag                                     32

<210> SEQ ID NO 71
<211> LENGTH: 32
<212> TYPE: DNA
<213> ORGANISM: Artificial Sequence
<220> FEATURE:
<223> OTHER INFORMATION: primer

<400> SEQUENCE: 71
gacagaaggc tatccatctc ctcagaaagt cc                                     32

<210> SEQ ID NO 72
<211> LENGTH: 24
<212> TYPE: DNA
<213> ORGANISM: Artificial Sequence
<220> FEATURE:
<223> OTHER INFORMATION: primer

<400> SEQUENCE: 72
tgtgaaaata agagcaaggc agtg                                              24

<210> SEQ ID NO 73
<211> LENGTH: 22
<212> TYPE: DNA
<213> ORGANISM: Artificial Sequence
<220> FEATURE:
<223> OTHER INFORMATION: primer

<400> SEQUENCE: 73
cattcatggc cttgtagaca cc                                                22

<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
gcctcagaag catgataagc                                                   20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
cccagagtga tacagatgtc                                                   20

<210> SEQ ID NO 76

```
<211> LENGTH: 25
<212> TYPE: DNA
<213> ORGANISM: Artificial Sequence
<220> FEATURE:
<223> OTHER INFORMATION: primer

<400> SEQUENCE: 76
tccagaactt acggaagcac ccacg                                           25

<210> SEQ ID NO 77
<211> LENGTH: 25
<212> TYPE: DNA
<213> ORGANISM: Artificial Sequence
<220> FEATURE:
<223> OTHER INFORMATION: primer

<400> SEQUENCE: 77
caggttcact gaagttggcg atcac                                           25

<210> SEQ ID NO 78
<211> LENGTH: 20
<212> TYPE: DNA
<213> ORGANISM: Artificial Sequence
<220> FEATURE:
<223> OTHER INFORMATION: primer

<400> SEQUENCE: 78
agggctggca ttgttctcta                                                 20

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
cttcagaggc aggaaacagg                                                 20

<210> SEQ ID NO 80
<211> LENGTH: 18
<212> TYPE: DNA
<213> ORGANISM: Artificial Sequence
<220> FEATURE:
<223> OTHER INFORMATION: primer

<400> SEQUENCE: 80
cgctcgcttc tctgtgca                                                   18

<210> SEQ ID NO 81
<211> LENGTH: 21
<212> TYPE: DNA
<213> ORGANISM: Artificial Sequence
<220> FEATURE:
<223> OTHER INFORMATION: primer

<400> SEQUENCE: 81
attttctgaa ccaagggagc t                                               21

<210> SEQ ID NO 82
<211> LENGTH: 19
<212> TYPE: DNA
<213> ORGANISM: Artificial Sequence
<220> FEATURE:
<223> OTHER INFORMATION: primer

<400> SEQUENCE: 82
```

```
tgccggctcc tcagtgctg                                              19

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83 aaacttttg accgcccttg a                                            21

<210> SEQ ID NO 84
<211> LENGTH: 20
<212> TYPE: DNA
<213> ORGANISM: Artificial Sequence
<220> FEATURE:
<223> OTHER INFORMATION: primer

<400> SEQUENCE: 84
attgaccact acctgggcaa                                             20

<210> SEQ ID NO 85
<211> LENGTH: 25
<212> TYPE: DNA
<213> ORGANISM: Artificial Sequence
<220> FEATURE:
<223> OTHER INFORMATION: primer

<400> SEQUENCE: 85
gagatacact tcaacacttt gacct                                       25

<210> SEQ ID NO 86
<211> LENGTH: 21
<212> TYPE: DNA
<213> ORGANISM: Artificial Sequence
<220> FEATURE:
<223> OTHER INFORMATION: primer

<400> SEQUENCE: 86
cagaaaccat cagcaagcag g                                           21

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
ttgacaaaag cctgggtggg                                             20

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
gaccctgcaa gatgcaagcc                                             20

<210> SEQ ID NO 89
<211> LENGTH: 20
<212> TYPE: DNA
<213> ORGANISM: Artificial Sequence
<220> FEATURE:
```

<223> OTHER INFORMATION: primer

<400> SEQUENCE: 89
gagcggatga aggtaaagcg                                               20

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
cccaccctac gaagtaccaa                                               20

<210> SEQ ID NO 91
<211> LENGTH: 20
<212> TYPE: DNA
<213> ORGANISM: Artificial Sequence
<220> FEATURE:
<223> OTHER INFORMATION: primer

<400> SEQUENCE: 91
ctggtcaagg tcatggtgtg                                               20

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
cccacctaca ggcccttctc                                               20

<210> SEQ ID NO 93
<211> LENGTH: 18
<212> TYPE: DNA
<213> ORGANISM: Artificial Sequence
<220> FEATURE:
<223> OTHER INFORMATION: primer

<400> SEQUENCE: 93
ggcatgggca tccacagt                                                 18

<210> SEQ ID NO 94
<211> LENGTH: 25
<212> TYPE: DNA
<213> ORGANISM: Artificial Sequence
<220> FEATURE:
<223> OTHER INFORMATION: primer

<400> SEQUENCE: 94
gaacaaaaag gtacatggcc cctga                                         25

<210> SEQ ID NO 95
<211> LENGTH: 26
<212> TYPE: DNA
<213> ORGANISM: Artificial Sequence
<220> FEATURE:
<223> OTHER INFORMATION: primer

<400> SEQUENCE: 95
ccttctgttc cctcttcagt gaggta                                        26

<210> SEQ ID NO 96

```
<211> LENGTH: 25
<212> TYPE: DNA
<213> ORGANISM: Artificial Sequence
<220> FEATURE:
<223> OTHER INFORMATION: primer

<400> SEQUENCE: 96
atgcccatcg tgcacaggga cctca                                          25

<210> SEQ ID NO 97
<211> LENGTH: 23
<212> TYPE: DNA
<213> ORGANISM: Artificial Sequence
<220> FEATURE:
<223> OTHER INFORMATION: primer

<400> SEQUENCE: 97
cgttctgcca cactgggctg tga                                            23

<210> SEQ ID NO 98
<211> LENGTH: 21
<212> TYPE: DNA
<213> ORGANISM: Artificial Sequence
<220> FEATURE:
<223> OTHER INFORMATION: primer

<400> SEQUENCE: 98
gtagccctgc tcactcttct t                                              21

<210> SEQ ID NO 99
<211> LENGTH: 20
<212> TYPE: DNA
<213> ORGANISM: Artificial Sequence
<220> FEATURE:
<223> OTHER INFORMATION: primer

<400> SEQUENCE: 99
aggtacagtc ccgtgtcaac                                                20

<210> SEQ ID NO 100
<211> LENGTH: 25
<212> TYPE: DNA
<213> ORGANISM: Artificial Sequence
<220> FEATURE:
<223> OTHER INFORMATION: primer

<400> SEQUENCE: 100
ggagatcctt cgaggagcag cactt                                          25

<210> SEQ ID NO 101
<211> LENGTH: 25
<212> TYPE: DNA
<213> ORGANISM: Artificial Sequence
<220> FEATURE:
<223> OTHER INFORMATION: primer

<400> SEQUENCE: 101
ggcgatttag cagcagatat aagaa                                          25

<210> SEQ ID NO 102
<211> LENGTH: 62
<212> TYPE: DNA
<213> ORGANISM: Homo sapiens

<400> SEQUENCE: 102
tttagaggcc atacccatgt ctatcccccc cgaggtcaag ttcaacaaac cctttgtct     60
```

```
tt                                                              62

<210> SEQ ID NO 103
<211> LENGTH: 62
<212> TYPE: DNA
<213> ORGANISM: Artificial Sequence
<220> FEATURE:
<223> OTHER INFORMATION: mutant

<400> SEQUENCE: 103
tttagaggcc atatgcatgt ctatcccccc cgaggtcaag ttcaacaaac cccttgtct    60 tt                                                              62

<210> SEQ ID NO 104
<211> LENGTH: 9
<212> TYPE: PRT
<213> ORGANISM: Homo sapiens

<400> SEQUENCE: 104

Ala Ile Pro Met Ser Ile Pro Pro Glu
1               5

<210> SEQ ID NO 105
<211> LENGTH: 9
<212> TYPE: PRT
<213> ORGANISM: Artificial Sequence
<220> FEATURE:
<223> OTHER INFORMATION: synthetic peptide

<400> SEQUENCE: 105

Ala Ile Pro Arg Ser Ile Pro Pro Glu
1               5

<210> SEQ ID NO 106
<211> LENGTH: 9
<212> TYPE: PRT
<213> ORGANISM: Artificial Sequence
<220> FEATURE:
<223> OTHER INFORMATION: synthetic peptide

<400> SEQUENCE: 106

Ala Ile Pro Val Ser Ile Pro Pro Glu
1               5

<210> SEQ ID NO 107
<211> LENGTH: 9
<212> TYPE: PRT
<213> ORGANISM: Artificial Sequence
<220> FEATURE:
<223> OTHER INFORMATION: synthetic peptide

<400> SEQUENCE: 107

Ala Ile Pro Leu Ser Ile Pro Pro Glu
1               5

<210> SEQ ID NO 108
<211> LENGTH: 9
<212> TYPE: PRT
<213> ORGANISM: Artificial Sequence
<220> FEATURE:
<223> OTHER INFORMATION: synthetic peptide

<400> SEQUENCE: 108

Ala Ile Cys Met Ser Ile Pro Pro Glu
1               5
```

```
<210> SEQ ID NO 109
<211> LENGTH: 9
<212> TYPE: PRT
<213> ORGANISM: Artificial Sequence
<220> FEATURE:
<223> OTHER INFORMATION: synthetic peptide

<400> SEQUENCE: 109

Ala Ile Pro Ala Ser Ile Pro Pro Glu
1               5

<210> SEQ ID NO 110
<211> LENGTH: 9
<212> TYPE: PRT
<213> ORGANISM: Artificial Sequence
<220> FEATURE:
<223> OTHER INFORMATION: synthetic peptide

<400> SEQUENCE: 110

Ala Ile Pro Met Ser Ile Pro Pro Lys
1               5

<210> SEQ ID NO 111
<211> LENGTH: 9
<212> TYPE: PRT
<213> ORGANISM: Artificial Sequence
<220> FEATURE:
<223> OTHER INFORMATION: synthetic peptide

<400> SEQUENCE: 111

Ala Ala Gly Arg Ser Leu Asn Pro Glu
1               5

<210> SEQ ID NO 112
<211> LENGTH: 9
<212> TYPE: PRT
<213> ORGANISM: Artificial Sequence
<220> FEATURE:
<223> OTHER INFORMATION: synthetic peptide

<400> SEQUENCE: 112

Ile Ala Gly Arg Ser Leu Asn Pro Asn
1               5

<210> SEQ ID NO 113
<211> LENGTH: 9
<212> TYPE: PRT
<213> ORGANISM: Artificial Sequence
<220> FEATURE:
<223> OTHER INFORMATION: synthetic peptide

<400> SEQUENCE: 113

Ile Ala Gly Arg Leu Leu Asn Pro Asn
1               5
```

COMPOSITIONS AND METHODS OF USE FOR ALPHA-1 ANTITRYPSIN HAVING NO SIGNIFICANT SERINE PROTEASE INHIBITOR ACTIVITY

CROSS REFERENCE TO RELATED APPLICATIONS

The present application claims priority to and is a continuation in part of U.S. patent application Ser. No. 12/177,798 filed on Jul. 22, 2008, which is a continuation in part of U.S. application Ser. No. 11/916,521 filed on Dec. 4, 2007, which is a U.S. National Stage Entry of PCT/US2006/022436, filed Jun. 7, 2005, which claims the benefit of U.S. Provisional Patent Application Ser. No. 60/687,850, filed on Jun. 7, 2005.

Further, the present application claims priority to and is a continuation in part of U.S. patent application Ser. No. 12/106,052 filed on Apr. 18, 2008, which claims the benefit of U.S. Provisional Patent Application Ser. No. 60/913,174 filed on Apr. 20, 2007.

Pursuant to 35 U.S.C. 119(e), 120, 121, and 365(c), the prior applications listed in paragraphs 002 and 003 of this application are incorporated herein by reference in their entirety

FEDERALLY FUNDED RESEARCH

The studies disclosed herein were supported in part by grant number AI-15614 from the National Institutes of Health. The U.S. government may have certain rights to practice the subject invention.

FIELD

Embodiments herein relate to compositions, methods and uses for alpha-1 antitrypsin (α-1 antitrypsin, AAT) or analog or mutant thereof having no significant serine protease inhibitor activity. In certain embodiments, AAT can have significantly reduced or eliminated serine protease inhibitor activity. Other embodiments relate to compositions and methods for reducing graft rejection in a subject undergoing or having undergone a transplant using AAT having no significant serine protease inhibitor activity. In certain embodiments, a composition having no significant serine protease inhibitor activity comprises a mutant AAT composition.

BACKGROUND

Normal plasma concentration of alpha-1 antitrypsin (AAT) ranges from 1.3 to 3.5 mg/ml. Under certain conditions, AAT can behave as an acute phase reactant and increase 3-4-fold during host response to inflammation and/or tissue injury or dramatic change such as with pregnancy, acute infection, and tumors. AAT easily diffuses into tissue spaces and forms a 1:1 complex with target proteases, principally neutrophil elastase. Other enzymes such as trypsin, chymotrypsin, cathepsin G, plasmin, thrombin, tissue kallikrein, and factor Xa can also serve as substrates. The enzyme/inhibitor complex is then removed from circulation by binding to serpin-enzyme complex (SEC) receptor and catabolized by the liver and spleen.

There are many diseases that culminate in organ dysfunction or failure. Representative non-limiting examples include renal failure due to diabetes melitus, hypertension, urinary output obstruction, drug-induced toxicity, or hypoperfusion, as well as cardiac dysfunction due to ischemic coronary artery disease, cardiomyopathy/infection, or valvulopathy. Pulmonary diseases include substantial damage due to chronic obstructive pulmonary disease (COPD, including chronic bronchitis and emphysema), AAT deficiency, cystic fibrosis, and interstitial fibrosis. Under certain conditions, the only therapeutic option for treatment of a subject may be organ transplantation. Pancreatic-islet transplantation provides diabetic patients with the only option for a tightly-controlled blood glucose level, as proven to be essential for prevention of diabetic complications. In the case of islets, post-transplant inflammation, which precedes immune rejection, is a critical determinant of graft survival. This early inflammation is mediated by cells other than the impending allospecific immune cells.

One challenge to therapeutic transplantation is the damaging effects of the host immune system on the transplant. MHC molecules exist on the surfaces of cells and the particular structures of MHC molecules are typically unique for each individual (with the exception of identical twins, where the MHC molecule complements are identical). The immune system is programmed to attack foreign or "non-self" MHC-bearing tissues. For these reasons, when an organ or tissue is transplanted into a recipient, an effort is made to optimize the degree of tissue matching between donor and recipient. MHC antigens are characterized for the recipient and donors. Matching a donor to an allograft recipient by MHC structure reduces the magnitude of the rejection response. An archetypal example is blood group matching. Most transplants are allografts that occur between non-identical members of the same species. Since these matches are imperfect, there is an expected graft rejection immune response associated with allografts. Current methods used, in order to enhance graft survival, include medications to suppress the immune response which can result in graft rejection. These medications are referred to immunosuppressant or antirejection drugs, such as prednisone, cyclosporine A, and cyclophosphamide, to name a few. As mentioned above, local inflammation is experienced immediately after grafting, and cells that are particularly sensitive to non-specific inflammation, such as islets, can endure graft dysfunction more severely than other types.

Despite advances in the field of antirejection therapy, graft maintenance remains a challenge since the available antirejection therapies are imperfect. For example, immunosuppression enhances the risk for opportunistic infection or neoplasia. Toxicities abound and include, but are not limited to, diabetes, organ dysfunction, renal failure, hepatic dysfunction, hematological defects, neuromuscular and psychiatric side effects, and many others. Therefore, there is a need for a more effective anti-rejection medical treatment that prolong graft survival and improve the quality of life.

Bone marrow transplantation is a unique kind of transplant where immune cells from a donor are transferred into a recipient, thereby conferring the donor immune system into the recipient. Here, the graft is capable of generating an immune response against the host, and this is termed "graft versus host" disease (GVHD). Immunosuppressive and antimicrobial treatment is required to block adverse consequences of GVHD, and a need exists for safer and more effective inhibitors of the adverse effects by the graft.

Because of some of the difficulties and inadequacies of conventional therapy for treating transplantation complications and associated side-effects, new therapeutic modalities are needed.

SUMMARY

Embodiments herein provide for methods and compositions for treating a subject having a medical disorder. A disorder may be organ failure, diabetes, someone undergoing a transplant (e.g. soft tissue or an organ) or organ disfunction due to disease or other cause.

Certain embodiments concern compositions for treating a subject having a medical disorder. In accordance with these embodiments, a composition can include, alpha-1 antitrypsin, or alleles thereof (for example, there are approximately 100 naturally occurring AAT variants), or fragments thereof or analogs thereof or fusion protein thereof (e.g. a human IgG or fragment of human IgG) where all compositions have no significant serine protease inhibition activity. In further embodiments, a composition contemplated herein includes, but is not limited to, modifying the composition to increase stability of the composition (e.g. polyethylene glycol linked molecules such as AAT or fragment thereof having no significant serine protease inhibition activity, etc.) It is contemplated herein that a composition may include a deglycosylated form of AAT or fragment thereof, analogs thereof, or recombinant form thereof, having no significant serine protease inhibition activity. Some embodiments herein include, but are not limited to, a composition using AAT having no significant serine protease inhibition activity wherein the AAT is naturally occurring M phenotype.

Compositions contemplated herein may further include an agent selected from the group consisting of an anti-inflammatory agent, an immunosuppressive agent, an immunomodulatory agent, an anti-viral agent, an anti-pathogenic agent, an anti-bacterial agent, a reverse transcriptase inhibitor, a protease inhibitor, and a combination thereof.

In certain embodiments, compositions herein can be administered orally, systemically, via an implant, time released or slow-release compositions (e.g. gel, microparticles etc.), intravenously, topically, intrathecally, subcutaneously, by inhalation, nasally, or by other means known in the art or a combination thereof.

Certain methods of treatment further concern reducing or eliminating one or more symptoms associated with a medical disorder. Further, some embodiments herein include symptoms that are characteristic of a disease, infection or onset thereof.

Some embodiments herein concern compositions of use for reducing or eliminating serine protease inhibition activity in the composition where no significant serine protease inhibitor activity is detectable. In accordance with these embodiments, alpha-1 antitrypsin, a fragment thereof, an analog thereof, alleles thereof or fusion molecule thereof, or combinations thereof can be heated to a temperature of about 85° C. to about 100° C. for about 1 minute to about 40 minutes, or about 5 minutes, or 10 minutes etc. In other particular embodiments, alpha-1 antitrypsin, a fragment thereof, an analog thereof, or fusion molecule thereof, can be heated and/or chemically treated until no significant serine protease inhibitor activity is detected. Certain methods can further include assessing serine protease inhibition activity of the alpha-1 antitrypsin, a fragment thereof, an analog thereof, or fusion molecule thereof, or combinations thereof using a serine protease inhibitor activity assay. It is contemplated herein that serine protease inhibitor activity can be measured before and/or after treatment.

In certain embodiments, compositions and methods disclosed herein can be used to reduce or prevent pain and/or symptoms associated with medical indications. In accordance with these embodiments, reduction in pain and or symptoms associated with a medical indication is on the order of about 10-20%, or about 30-40%, or about 50-60%, or about 75-100% reduction or inhibition.

In certain embodiments, α1-antitrypsin used in the methods and compositions herein can include, but is not limited to, Aralast™ (Baxter), Zemaira™ (Aventis Behring), Prolastin™ (Bayer), Aprotonin™ or Trasylol™ (Bayer Pharmaceutical Corporation) and Ulinistatin™ (Ono Pharmaceuticals, Inc.) or any combination thereof. In other embodiments, AAT or an AAT fragment or an AAT analog used in methods and compositions herein can include naturally occurring AAT or AAT fragment or analog or allele thereof.

In other embodiments, an anti-inflammatory compound or immunomodulatory drug can include, but is not limited to, interferon; interferon derivatives comprising betaseron, β-interferon; prostane derivatives comprising iloprost, cicaprost; glucocorticoids comprising cortisol, prednisolone, methylprednisolone, dexamethasone; immunosuppressives comprising cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives comprising ACTH and analogs thereof, soluble TNF-receptors; TNF-antibodies; soluble receptors of interleukines, other cytokines, T-cell-proteins; antibodies against receptors of interleukines, other cytokines, T-cell-proteins; and calcipotriols and analogues thereof taken either alone or in any combination thereof.

In certain embodiments, compositions for administration can be in a range of between about 10 ng and about 10 mg per ml or mg of the formulation. A therapeutically effective amount of AAT peptides or drugs that have similar activities as AAT or peptides drug may be measured in molar concentrations and may range between about 1 nM and about 10 mM. The formulation is also contemplated in combination with a pharmaceutically or cosmetically acceptable carrier. Precise doses can be established by well known routine clinical trials without undue experimentation.

In some embodiments, pharmaceutical compositions contemplated herein are administered orally, systemically, via an implant, intravenously, topically, intrathecally, intracranially, intraventricularly, by inhalation or nasally.

In certain embodiments, the subject or mammal is a human.

In other embodiments, the subject or mammal can be a domesticated or a non-domesticated mammal.

In certain embodiments, synthetic and/or naturally occurring peptides may be used in compositions and methods herein for example, providing other than serine protease inhibitor activity of AAT. Homologues, natural peptides, with sequence homologies to AAT including peptides directly derived from cleavage of AAT may be used or other peptides such as, peptides that have AAT-like activity other than serine protease inhibitor activity. Other peptidyl derivatives, e.g., aldehyde or ketone derivatives of such peptides are also contemplated herein. Without limiting to AAT and peptide derivatives of AAT, compounds like oxadiazole, thiadiazole and triazole peptoids and substances can include, but are not limited to, certain phenylenedialkanoate esters, CE-2072, UT-77, and triazole peptoids. Examples of analogues are TLCK (tosyl-L-lysine chloromethyl ketone) or TPCK (tosyl-L-phenylalanine chloromethyl ketone) or any combination thereof.

In certain embodiments, human AAT mutants were generated having no significant serine protease inhibitor activity. In other embodiments, constructs of human AAT mutants having no significant serine protease activity can be associated with a vector. Vectors include, but are not limited to, genetic therapy vectors (e.g. EF vector of Epstein Barr Virus). In some embodiments vectors associated with a human AAT construct having no significant serine protease inhibitor activity may be used to treat a subject undergoing or having undergone a transplant. Other embodiments concern AAT-derived fragment constructs adapted to have no significant serine protease inhibitor activity. In accordance with these embodiments, constructs can be generated and amplified to produce large quantities of AAT having no significant serine protease inhibitor activity. Industrial sized scale production is contemplated in order to produce large quantities of AAT having no significant serine protease inhibitor activity for use in treatment and procedures contemplated herein. In certain embodiments, attenuated viruses may be used to produce an AAT construct. In other embodiments, attenuated viruses or viral fragments known in the art may be used to introduce AAT constructs having no significant serine protease activity to a subject using, for example, gene therapy techniques. In other embodiments, bacterial hosts may be used to produce large quantities of AAT having no significant serine protease inhibitor activity.

Embodiments of the present invention provide for methods for treating a subject having or in need of a transplant. In accordance with these embodiments, a subject may be treated with a composition for reducing the risk of a transplant rejection. For example, subjects undergoing a transplant can be administered a composition of AAT or fragment of AAT having no significant serine protease activity. In other embodiments, an AAT composition can be derived from an AAT construct expressed and produced by a microorganism wherein the AAT construct has no significant serine protease inhibitor activity. Compositions contemplated herein can be administered before transplantation, during transplantation, after transplantation or combination thereof. In addition, compositions may further include one or more anti-transplant rejection agent, anti-inflammatory agent, immunosuppressive agent, immunomodulatory agent, anti-microbial agent, or a combination thereof.

A transplant may include an organ transplant and/or a non-organ transplant. For example lung, kidney, heart, liver, cornea, skin, stem cells, soft tissue (e.g. facial component transplant), intestinal transplants, bone marrow, pancreatic islet, pancreas transplant or combination thereof are contemplated.

Embodiments of the present invention provide for methods for ameliorating symptoms or signs experienced by a subject having or in need of a transplant. In accordance with these embodiments, symptoms or signs may include conditions associated with graft versus host disease (GVHD), or graft rejection. In one example, methods disclosed herein may be used to treat a subject undergoing bone marrow transplantation. In another embodiment, symptoms or signs may include but is not limited to one or more of the following, kidney failure, lung failure, heart failure, reduced renal function (increased creatinine, decreased urine output), reduced pulmonary function (increased shortness of breadth, fever, cough, sputum, hypoxemia), reduced cardiac function (shortness of breach, chest pain, fatigue, pulmonary or peripheral edema, valvulopathy), reduced islet function (increased glucose, diabetes melitus), graft versus host disease (gastrointestinal (GI) ulceration, pulmonary failure, skin ulceration, coagulopothy, CNS dysfunction (mental status changes, coma) CMV (cytomeglovirus infection, viral, fungal parasitic infection)).

Other embodiments provide for methods for promoting prolonged graft survival and function in a subject including administering to a subject in need thereof a therapeutically effective amount of a composition including a substance of AAT having no significant serine protease inhibitor activity.

In another embodiment, methods herein provide for inducing immune tolerance specific for a graft and/or reduce the need for immunosuppressive therapy. In accordance with this embodiment, the immune system of the transplant recipient may have reduced or lost the specific ability to attack the graft while maintaining its ability to mount any other type of immune attack. In accordance with this method the subject can be administered a composition including a compound effective amount of a composition including a substance of AAT having no significant serine protease inhibitor activity.

In certain embodiments of the present invention, an anti-inflammatory agents or immunomodulatory agents can be included in any of the compositions disclosed. These agents include, but are not limited to, one or more of interferon, interferon derivatives including betaseron, beta-interferon, prostane derivatives including iloprost, cicaprost; glucocorticoids including cortisol, prednisolone, methyl-prednisolone, dexamethasone; immunosuppressives including cyclosporine A, FK-506, methoxsalene, thalidomide, sulfasalazine, azathioprine, methotrexate; lipoxygenase inhibitors comprising zileutone, MK-886, WY-50295, SC-45662, SC-41661A, BI-L-357; leukotriene antagonists; peptide derivatives including ACTH and analogs thereof; soluble TNF-receptors; TNF-antibodies; soluble receptors of interleukins, other cytokines, T-cell-proteins; antibodies against receptors of interleukins, other cytokines, T-cell-proteins; and calcipotriols; Celcept®, mycophenolate mofetil, and analogues thereof taken either alone or in combination.

Embodiments of the present invention provide for methods for reducing graft rejection in a subject. In accordance with these embodiments, a subject may be treated with a composition for reducing the risk of graft rejection responses or a side-effect of a graft rejection response in a subject. In accordance with this method, the subject can be administered a composition including a compound effective amount of a composition including a substance of AAT having no significant serine protease inhibitor activity. In one example, reducing graft rejection may include reducing the symptoms associated with graft rejection in a subject having an organ transplant, such as a kidney transplant or a bowel transplant or a non-organ transplant, such as a bone marrow transplant soft tissue transplant.

In accordance with embodiments disclosed herein, any of the disclosed compositions may be used to ameliorate symptoms associated with a transplant and/or transplant rejection. These symptoms may include but are not limited to, infiltration of graft with cells and/or serum factors (for example, complement, anti-graft antibodies), increased cytokine and/or chemokine production, increased nitric oxide production, increased apoptosis and cell death, and increased immune response against the transplant tissue and/or cells.

In another aspect, method of ameliorating a symptom or sign associated with transplantation in a subject in need of said amelioration are contemplated. In accordance with this embodiment, a composition may be administered to a subject such as a pharmaceutically effective amount including a compound effective amount of a composition including a substance of AAT having no significant serine protease inhibitor activity.

In certain embodiments, synthetic and/or naturally occurring peptides may be used in compositions and methods disclosed in embodiments herein. Homologues, natural peptides, derived from AAT including peptides directly derived from cleavage of AAT may be used or other peptides such as, peptides that inhibit serine proteases or have AAT-like activity. Other peptidyl derivatives, e.g., aldehyde or ketone derivatives of such peptides are also contemplated herein.

Without limiting to AAT and peptide derivatives of AAT, compounds like oxadiazole, thiadiazole and triazole peptoids and substances comprising certain phenylenedialkanoate esters, CE-2072, UT-77, and triazole peptoids may be used. Examples of analogues are TLCK (tosyl-L-lysine chloromethyl ketone) or TPCK (tosyl-L-phenylalanine chloromethyl ketone).

In some embodiments, AAT peptides contemplated for use in the compositions and methods of the present invention are also intended to include any and all of those specific AAT peptides including, but not limited to, the 10 amino acid AAT peptides of SEQ ID NO. 61 depicted supra. Any combination of consecutive amino acids depicting a portion of AAT or AAT-like activity may be used, such as amino acids 2-12, amino acids 3-13, 4-14, etc. of SEQ ID NO. 61, as well as any and all AAT peptide fragments corresponding to select amino acids of SEQ ID NO. 61. Applicants are herein entitled to compositions based upon any and all AAT peptide variants based upon the amino acid sequence depicted in SEQ ID NO. 61.

In one aspect of the invention, pharmaceutical compositions can be administered orally, systemically, via an implant, intravenously, topically, intrathecally, intratracheally, intracranially, subcutaneously, intravaginally, intraventricularly, intranasally such as inhalation, mixed with grafts by flushing of organ or suspension of cells, or any combination thereof.

Other embodiments concern methods for preventing or reducing the risk of developing an organ or cellular transplant rejection in a subject having had or undergoing a cellular transplant, the method comprising administering to the subject a composition comprising a mutant AAT construct or other AAT molecule having no significant serine protease inhibitor activity. Any composition herein can be administered to the subject before transplantation, during transplantation, after transplantation or combination thereof. A composition contemplated herein can further include one or more anti-transplant rejection agent, anti-inflammatory agent, immunosuppressive agent, immunomodulatory agent, antimicrobial agent, or a combination thereof. A composition herein can include, but is not limited to a carboxy-terminal peptide or amino-terminal peptides corresponding to AAT, an analog thereof, any derivative of AAT carboxy terminus that binds to serpin-enzyme complex (SEC) receptor or a combination thereof. Cellular transplant can be a cornea, bone marrow, liver, stem cell, pancreatic islet, pancreas, kidney, lung, intestinal transplant, or a combination thereof. In certain embodiments, a cellular transplant can be a pancreatic islet cell transplant.

Immunosuppressive agent can be chosen from inhibitors of apoptosis, serine protease inhibitors, reducers of lymphocyte numbers, reducers of cytokine production, reducers of cytokine activities, monoclonal antibodies, reducers of cytokine receptors, reducers of nitric oxide production and a combination thereof.

Other agents contemplated herein can include reducers of cytokine production, reducers of cytokine activities, reducers of cytokine receptors is an inhibitor of one or more of TNFα (tumor necrosis factor alpha), IL-1 (interleukin-1), IL-12 (interleukin-12), IL-18 (interleukin-118), IL-17 (interleukin-17), IL-23 (interleukin-23), IL-32 (interleukin-32), IFNγ (interferon gamma) or a combination thereof In other methods contemplated herein, treating organ or cellular transplant rejection in a subject is contemplated by identifying a subject having or in need of a cellular or organ transplant; performing cellular or organ transplantation on the subject; and administering a therapeutically effective amount of a composition comprising AAT, AAT-like compound, AAT analog, AAT derivative, serine protease inhibitor, one or more carboxy-terminal peptides derived from AAT, any derivative of AAT carboxy terminus that binds to serpin-enzyme complex (SEC) receptor or combination thereof to the subject. In accordance with these methods, treating the subject with the composition reduces the risk of transplantation rejection by at least 10% compared to a subject not treated with the composition.

Other embodiments herein include treating diabetes in a subject by identifying a subject having or at risk of developing diabetes; performing pancreatic islet cell transplantation on the subject; and administering a therapeutically effective amount of a composition comprising AAT having no significant serine protease inhibitor activity, AAT-like compound, AAT analog, AAT derivative, one or more peptides derived from AAT, any derivative or fragment of AAT carboxy terminus having no significant serine protease inhibitor activity or combination thereof to a subject having a transplant or having had a transplant. Administering the composition may include administering the composition to the organ or cells to be transplanted before transplant, administering the composition to the subject before transplant, administering the composition to the subject during transplantation, administering the composition to the subject after transplantation or a combination thereof. Certain subjects contemplated herein have or are at risk of developing Type 1 diabetes. These subjects may have been diagnosed with early phase type 1 diabetes. Other subjects may have or are at risk of developing Type 2 diabetes. It is contemplated that using compositions disclosed herein may reduce the symptoms associated with diabetes by 10%, or 20%, or 30% or more. It is also contemplated that using compositions disclosed herein may reduce or eliminate graft rejection and/or cell rejection in a subject having had or undergoing a transplant.

Yet other embodiments herein include methods reducing a side-effect of cellular transplant rejection in a subject, the method comprising administering to the subject a composition comprising AAT having no significant serine protease inhibitor activity, one or more carboxy-terminal peptides derived from AAT having no significant serine protease inhibitor activity, or human AAT-derived mutant having no significant serine protease inhibitor activity. In accordance with these embodiments, a side effects of cellular or organ transplant can be production of pro-inflammatory cytokines, infiltration of immunocompetent cells, infiltration of inflammatory cells, infiltration of cytotoxic T-cells, infiltration of mature dendritic cells, infiltration of monocytes, production of nitric oxide, production of prostaglandins, production of reactive oxygen species, production of super oxide radicals, infiltration of natural killer cells, infiltration of natural killer T-cells and a combination thereof.

Other exemplary methods include preventing or reducing the risk of developing pancreatic islet cell transplant rejection in a subject having had or undergoing a pancreatic islet cell transplant, the method comprising administering to the subject a composition comprising alpha-1 antitrypsin (AAT), one or more carboxy-terminal peptides derived from AAT, engager of the SEC receptor, alpha-1 antitrypsin-like compound, serine protease inhibitor or combination thereof. A subject may have juvenile or late onset type 1 diabetes or type 2 diabetes. Reducing the risk of developing pancreatic islet cell transplant rejection in a subject can include reducing the risk by at least 10 percent in the subject compared to a second subject not treated with the composition.

In certain embodiments, the subject is a human. In some embodiments, the subject is a domesticated animal or livestock.

A pharmaceutical composition contemplated herein may include, AAT having no significant serine protease inhibitor activity, AAT analog having no significant serine protease inhibitor activity, AAT derivative having no significant serine protease inhibitor activity, one or more peptides derived from AAT having no significant serine protease inhibitor activity, one or more carboxy-terminal peptides derived from AAT having no significant serine protease inhibitor activity, any derivative or fragment of AAT carboxy terminus that binds to serpin-enzyme complex (SEC) receptor having no significant serine protease inhibitor activity or combination thereof and optionally, at least one of an anti-transplant rejection agent, an anti-inflammatory agent, an immunosuppressive agent, an immunomodulatory agent, and an anti-microbial agent. In accordance with these embodiments, the pharmaceutical composition can be AAT having no significant serine protease inhibitor activity, AAT analog having no significant serine protease inhibitor activity AAT derivative having no significant serine protease inhibitor activity, peptide or carboxy-terminal peptide corresponding to AAT having no significant serine protease inhibitor activity, any derivative or fragment of AAT carboxy terminus having no significant serine protease inhibitor activity that binds to serpin-enzyme complex (SEC) receptor or combination thereof and one or more anti-transplant rejection agents.

Other exemplary methods can include methods for inducing immunological tolerance in a subject undergoing a cellular or organ transplant including, but not limited to, administering to the subject a composition comprising AAT having no significant serine protease inhibitor activity or an AAT mutant having no significant serine protease inhibitor activity or combination thereof. wherein the subject is undergoing islet cell transplant. One cellular transplant can be pancreatic islet cell transplant. One transplant can be a temporary cadaver transplant of skin in a burn patient where compositions herein inhibit rejection of the temporary cadaver treatments.

Other exemplary methods can include, at least one of increasing numbers of or increasing effectiveness and/or of sustaining T-regulatory cells in a subject by administering an AAT or AAT derivative composition having no significant serine protease inhibitor activity to the subject.

Yet other exemplary methods can include increasing immune tolerance in a subject in need thereof by administering AAT having no significant serine protease inhibitor activity or AAT derivative or fragment(s) or AAT mutant composition having no significant serine protease inhibitor activity to the subject in need thereof. In addition, these methods may further include inhibiting dendridic cell maturation. For example, compositions contemplated herein may be administered to a subject having, undergoing or previously having had a transplant.

Other exemplary methods herein include reducing antigen presentation by dendritic cells by administering an AAT or AAT derivative composition having no significant serine protease inhibitor activity to the cells. In accordance with these embodiments, the cells are cells of a human subject and administration is to the subject in need of reducing antigen presentation. Other examples herein include inhibiting maturation of dendritic cells by administering AAT, any derivative or fragment of AAT carboxy terminus having no significant serine protease inhibitor activity or AAT derivative composition having no significant serine protease inhibitor activity to a subject having, undergoing or previously having had a transplant.

As such, those skilled in the art will appreciate that the conception, upon which this disclosure is based, can readily be used as a basis for designing other methods for carrying out the several features and advantages of the present invention.

BRIEF DESCRIPTION OF THE DRAWINGS

The following drawings form part of the present specification and are included to further demonstrate certain embodiments disclosed herein. Embodiments may be better understood by reference to one or more of these drawings in combination with the detailed description of specific embodiments presented herein.

FIGS. 6A-6D illustrates the effect of AAT on Islet allograft transplantation. 6A illustrates the time course study after transplantation. 6B illustrates an immune infiltrate found outside the graft area. 6C illustrates an increase in the presence of CD4+ and a comparative decrease in monocytes and neutrophils. 6D illustrates levels of glucose reflecting a level of tolerance with respect to days following allografting of the same donor (left) and a $3^{rd}$ donor re-graft (right), indicating induction of specific immune tolerance.

FIGS. 9A-9D illustrate exemplary extended AAT monotherapy where exposure induces strain-specific immune tolerance towards islet allografts in mice. Islet allograft transplantation was performed and blood glucose was followed in mice that received albumin (ALB, n=6) or hAAT monotherapy (n=24) for various periods of times. (A) Islet graft survival curve. (B) Summary of uninterrupted normoglycemic intervals achieved during and after hAAT monotherapy ("First graft") and during a second grafting procedure that was carried out in explanted animals in the absence of therapy ("Second graft") (n=7). Double-underlined headings indicate number of hAAT monotherapy and therapy-free days. The outcome of the second grafting procedure is indicated per individual mouse. (C) Representative Blood glucose follow-up. Albumin (ALB)-treated animals are represented by dashed line. Day of hAAT treatment withdrawal is indicated. Treatment-free glucose levels were determined during the ensuing days. Graft removal by nephrectomy, resulting in hyperglycemia, is indicated. A second grafting without further hAAT treatment was performed with same strain islet allograft (left) or third strain islet allograft (right). Transplantation outcome of the second grafting is monitored for 50 days. (D) Histology. Representative day 72 explanted graft from hAAT-treated mice 20 days after withdrawal of hAAT treatment. H&E stain, image of entire islet graft site. Islet mass appears flanked by a dense mononuclear cell population (thick arrows).

FIGS. 13A-13C represent exemplary time-dependent hAAT-induced distribution of Treg cells between DLN and allograft. Foxp3-GFP knock-in mice (H-2b) were grafted with wild-type Balb/c tissue (H-2d). Mice received a 10-day hAAT treatment or albumin protocol (see FIG. 9). (A) Inguinal DLN. FACS analysis of CD4+-sorted foxp3-GFP-positive DLN cells. Inset, RT-PCR for foxp3 mRNA transcripts in DLN. Illustrated are representative time-points. (B) Matrigel-skin graft. Treg cells in matrigel grafts on day 10 identified by fluorescent microscopy of unstained material (left) plus DAPI-counter stained material (right). (C) Islet graft. Day 14 Treg cells identified in the "cuff" site (see FIG. 9D). Anti-GFP antibody immunostaining and DAPI counter-staining. Representative image of three hAAT-treated grafts. Grafts from albumin-treated mice contained no "cuff" (not shown).

FIG. 25B represents an exemplary histogram of the effects of AAT (5 mg/ml, 0.8 mg/ml) or HI AAT (striped bar, 5 mg/ml, 0.8 mg/ml) on HIV production represented by p24 production (pg/ml) in stimulated U1 cells.

FIG. 31 represents an exemplary table of engineered and natural AAT variants.

FIG. 36 represents sequences of control and a mutant having no significant serine protease inhibitor activity.

DESCRIPTION OF ILLUSTRATIVE EMBODIMENTS

Definitions

Figure 1A:
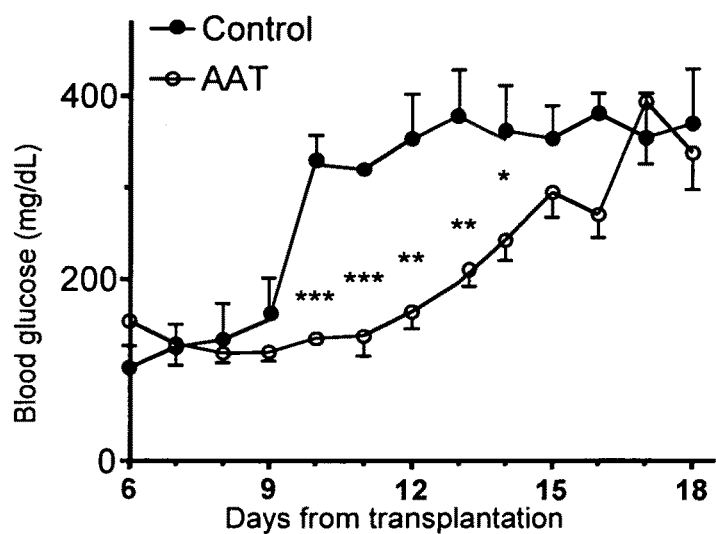
FIGS. 1A-1D illustrates an exemplary method of treating islet allografts with AAT. Islets from DBA/2 mice (H-2d) were transplanted under the renal capsule of streptozotocin-induced hyperglycemic C57BL/6 mice (H-2b). (A) Glucose levels from days 6-18. (B) Treatment protocols. Control and full AAT treatment are described in panel A. Early AAT treatment consists of treatment on days −1, 1 and 3 (2 mg, n=3). Late AAT treatment consists of treatment from day 2 and on every 2 days (2 mg, n=3). (C) Effect of mouse anti-human-AAT antibodies. Dashed line indicates post transplantation glucose levels of a mouse under full AAT treatment protocol (see A, B) that was immunized by multiple administrations of human AAT prior to transplantation (1 representative, n=3). Solid line indicates glucose levels of a non-immunized mouse treated under full AAT treatment protocol (1 representative, n=10). Arrow indicates detection of treatment-induced, anti-human-AAT antibodies in the non-immunized representative mouse. (D) Comparison of day 15 post-transplantation glucose levels in mice that were under full treatment protocol with ALB (n=3) or AAT (non-immunized n=10, immunized n=3). Of the AAT-treated group, antibodies were detected on day 15 in 3/3 immunized mice and in 6/10 non-immunized mice.

As used herein, "a" or "an" may mean one or more than one of an item.

As used herein, "about" can mean plus or minus 10%, for example, about 10 minutes can mean from 9 to 11 minutes.

As used herein "analog of alpha-1-antitrypsin" may mean a compound having alpha-1-antitrypsin-like activity other than serine protease inhibitor activity. In one embodiment, an analog of alpha-1-antitrypsin is a functional derivative of alpha-1-antitrypsin. In a more particular embodiment, an analog of alpha-1-antitrypsin is a compound with no significant serine protease inhibitor activity.

DETAILED DESCRIPTION

In the following sections, various exemplary compositions and methods are described in order to detail various embodiments of the invention. It will be obvious to one skilled in the art that practicing the various embodiments does not require the employment of all or even some of the specific details outlined herein, but rather that concentrations, times and other specific details may be modified through routine experimentation. In some cases, well known methods, or components have not been included in the description.

Embodiments herein provide for methods and compositions for treating a subject having a medical disorder. Certain embodiments concern compositions for treating a subject having a medical disorder. In accordance with these embodiments, the composition may include, alpha-1 antitrypsin, a fragment thereof, an analog thereof, or fusion molecule thereof, having no significant serine protease inhibition activity. In other embodiments, a composition may further include, but is not limited to, an anti-inflammatory agent, an immunosuppressive agent, an immunomodulatory agent, an antimicrobial agent, an anti-viral agent, an anti-bacterial agent, and a combination thereof.

Other embodiments herein concern methods of treating a subject with a medical disorder including administering to the subject in need of such a treatment a therapeutically effective amount of a composition including but not limited alpha-1 antitrypsin, a fragment thereof, an analog thereof, or fusion molecule thereof, mutant molecule thereof having no significant serine protease inhibition activity. In accordance with these embodiments, the disorder can be a need for a transplant or diabetes.

Certain embodiments herein concern organ dysfunction or failure. There are many diseases that culminate in organ dysfunction or failure. Representative non-limiting examples include renal failure due to diabetes melitus, hypertension, urinary output obstruction, drug-induced toxicity, or hypoperfusion, as well as cardiac dysfunction due to ischemic coronary artery disease, cardiomyopathy/infection, or valvulopathy. Pulmonary diseases include substantial damage due to chronic obstructive pulmonary disease (COPD, including chronic bronchitis and emphysema), AAT deficiency, cystic fibrosis, and interstitial fibrosis. Under certain conditions, the only therapeutic option for treatment of a subject may be organ transplantation. Pancreatic-islet transplantation provides diabetic patients with the only option for a tightly-controlled blood glucose level, as proven to be essential for prevention of diabetic complications. In the case of islets, post-transplant inflammation, which precedes immune rejection, is a critical determinant of graft survival. This early inflammation is mediated by cells other than the impending allospecific immune cells.

Despite advances in the field of antirejection therapy, graft maintenance remains a challenge since the available antirejection therapies are imperfect. For example, immunosuppression enhances the risk for opportunistic infection or neoplasia. Toxicities abound and include, but are not limited to, diabetes, organ dysfunction, renal failure, hepatic dysfunction, hematological defects, neuromuscular and psychiatric side effects, and many others. Therefore, there is a need for a more effective anti-rejection medical treatment that prolong graft survival and improve the quality of life.

Bone marrow transplantation is a unique kind of transplant where immune cells from a donor are transferred into a recipient, thereby conferring the donor immune system into the recipient. Here, the graft is capable of generating an immune response against the host, and this is termed "graft versus host" disease (GVHD). Immunosuppressive and antimicrobial treatment is required to block adverse consequences of GVHD, and a need exists for safer and more effective inhibitors of the adverse effects by the graft. methods or components have not been included in the description.

Embodiments of the present invention provide for methods for treating a subject having or in need of a transplant. In accordance with these embodiments, a subject may be treated with a composition of AAT mutant, having no significant serine protease inhibitor activity. In addition, one embodiment provides for methods including treating a subject with a composition comprising a compound having an AAT mutant associated with a gene therapy delivery fragment or in a matrix capable of quick or slow release delivery to a subject in need thereof. In one embodiment, the composition can include AAT, analog thereof having no significant serine protease inhibitor activity to for example, promote transplant survival or reduce a side effect of the transplant. Further, the administration of the composition can be before transplantation, during transplantation, after transplantation or combination thereof. In addition, the composition may further include one or more additional therapies such as immunosuppressive therapies. A transplant of the present invention may include transplantation of an organ such as lung, kidney, heart, liver, skin, pancreas, or bowel organ or non-organ such bone marrow, pancreatic islet, cornea, and/or soft tissue.

Human pancreatic islet transplantation has a low 5-year graft survival rate. The current immunosuppression protocol in this procedure is void of anti-inflammatory corticosteroids. AAT reduces cytokine-mediated islet damage and interferes with inflammatory processes. Certain embodiments disclosed herein concern AAT-mutants having no significant serine protease inhibitor activity for monotherapy for allografts with anti-inflammatory conditions that impair dendritic cell maturation and favor development of antigen-specific T regulatory cell. Given its established safety in patients, AAT-mutants or fragments or peptides having no significant serine protease inhibitor activity may be considered for use during human islet transplantation.

Islet transplantation can provide type-1 diabetes patients with glycemic control that can eliminate or significantly reduce a need for exogenous insulin injections. In this procedure, isolated islets are introduced into the hepatic portal circulation of a diabetic patient. The immunosuppressive protocol used for islet transplantation excludes diabetogenic corticosteroids and therefore is void of anti-inflammatory activity. To date, islet loss in most transplant patients steadily progresses and results in a low 5-year graft survival rate.

Islets are particularly prone to injury during inflammatory conditions. Immediately after transplantation, viable islet mass rapidly decreases, regardless of allogeneic discrepancy. As damage intensifies, necrotic islet beta cells secrete injurious cytokines and chemokines while presenting allogeneic antigens to the host. Thus, grafted islets actively participate in the inflammatory flare and become activators, and targets, of resident macrophages.

Extent of inflammation and injury can determine the degree of antigen presentation and closely affects the expansion of allospecific effector cells. In addition, the favorable state of immune tolerance can be elaborated by a shift in balance between effector T cells and protective regulatory T (Treg) cells, a process which requires the uninterrupted activity of IL-2. By reducing the intensity of inflammation while allowing IL-2 activity one may provide optimal conditions for prolonged allograft survival.

As disclosed herein, effects of extended AAT-mutant having no significant serine protease inhibitor activity monotherapy on islet allograft rejection were examined. In order to allow extended therapy with hAAT-mutant having no significant serine protease inhibitor activity, mice heterozygous for the human AAT transgene (hAAT-Tg) were used as graft recipients. In these mice, the human AAT sequence is preceded by a surfactant promoter, thus limiting hAAT-mutant expression to lung epithelial cells and circulating hAAT-mutant having no significant serine protease inhibitor activity levels to less than 10 ng/ml. Thus, the impact of monotherapy on the process of allograft rejection was examined in the setting of a normal immune system. After rendered diabetic, mice were grafted with islets from another mouse strain and were treated with hAAT-mutant having no significant serine protease inhibitor activity for extended periods of time. Unexpectedly, therapy withdrawal revealed the fervent induction of strain-specific treatment-induced immune tolerance.

Embodiments herein provide for administration of compositions including, but not limited to, AAT having no significant serine protease inhibitor activity, derivatives or fragments or peptides of AAT having no significant serine protease inhibitor activity, AAT-mutants having no significant serine protease inhibitor activity, peptides derived from the last 80 amino acids of the carboxy-terminus of AAT having no significant serine protease inhibitor activity, or AAT derivative or composition with AAT-like activity having no significant serine protease inhibitor activity to a subject having or previously having had graft surgery for example, cellular implantation, cellular supplementation, organ implantation and/or tissue implantation. In certain embodiments, a subject in need of increased immune tolerance is contemplated to reduce rejection of implanted or grafted cells, tissue or organ. In other embodiments, administration of AAT having no significant serine protease inhibitor activity or AAT-mutant having no significant serine protease inhibitor activity to a subject can be prior to implantation to reduce rejection and/or reduce immune response to the transplantation. Subject contemplated herein in need of immune tolerance include, but are not limited to, subjects having undergone a transplant or subjects scheduled for a transplant.

In certain embodiments, a subject may be administered one or more infusions of an AAT or AAT-mutant or AAT derived peptide composition having no significant serine protease inhibitor activity to reduce rejection or increase tolerance of a transplant or prolong acceptance of the transplanted organ or tissue in the subject. In certain examples, the subject may have undergone a transplant recently, a month ago or a year or more prior to administration of the AAT composition.

In certain embodiments, compositions of AAT or AAT derivative, or carboxy terminal fragment of AAT capable of binding to the SEC receptor or compositions with AAT-like activity may be administered to a subject in need thereof to induce immune tolerance in the subject. As used herein carboxy terminal region of AAT can include the last 80 amino acids of SEQ ID NO.: 61 or hAAT molecule. In other embodiments, peptides derived from AAT can include 10-mers, 20-mers, 30-mers, 40-mers, 50-mers and more of a human AAT molecule wherein any of the contemplated peptides have no significant serine protease inhibitor activity.

Yet other embodiments herein concern administering AAT-mutant compositions or AAT peptide-derivatives or compositions with AAT-like activity having no significant serine protease inhibitor activity to a burn patient. For example, these compositions can be administered to a burn patient undergoing interim therapy of cadaver skin applied to burned regions of the patient. In accordance with these embodiments, the patient can be administered iv AAT compositions having no significant serine protease inhibitor activity at periodic times (e.g. daily, weekly or monthly) to prolong the tolerance period for the cadaver skin permitting re-growth of the patient's own tissue.

In other exemplary embodiments, a subject contemplated herein may have early phase type 1 diabetes. This disease often affects young children and can be called "juvenile type 1 diabetes." There is also a similar type 1 diabetes that affects older individuals and is called "late onset" type 1 diabetes. Embodiments herein contemplate that AAT-mutant or AAT derived peptides having no significant serine protease inhibitor activity suppress the immune response. Since both juvenile, as well as late onset type 1 diabetes, have an autoimmune response directed against the insulin producing beta cells in the pancreatic islets, ATT having no significant serine protease inhibitor activity can be used as a treatment for both juvenile as well as late onset type 1 diabetes via the T-regulatory cells. In addition, the anti-inflammatory properties of AAT, contributes to protecting the beta cells from the cytotoxic effects of pro-inflammatory cytokines and inflammatory mediators.

In other embodiments, compositions contemplated herein can be used to treat a subject having type 2 diabetes. For example, a subject may be treated with periodic application of the composition such as monthly or weekly administrations of compositions disclosed herein.

In some embodiments, AAT having no significant serine protease inhibitor activity can be used to treat autoimmune diseases. Lowering a dose of an immunosuppressive agent may be performed during treatments with compositions contemplated herein. Other autoimmune diseases that are treated with immunosuppressive regimens may also be treated with AAT-mutant compositions having no significant serine protease inhibitor activity while lowering the dose of immunosuppressive agents include, but are not limited to, lupus erythematosus, Crohn's disease, ulcerative colitis, psoriasis, biliary cirrhrosis, and thrombocytopenia.

Any of the embodiments detailed herein may further include one or more a therapeutically effective amount of anti-microbial drugs anti-inflammatory agent, immunomodulatory agent, or immunosuppressive agent or combination thereof.

Non-limiting examples of anti-rejection agents/drugs may include for example cyclosporine, azathioprine, corticosteroids, FK506 (tacrolimus), RS61443, mycophenolate mofetil, rapamycin (sirolimus); mizoribine, 15-deoxyspergualin, and/or leflunomide or any combination thereof.

In addition, other combination compositions of methods disclosed in the present invention include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. Antibody-based therapies may be used as induction therapy and/or anti-rejection drugs in combination with the compositions and methods of the present invention.

In one embodiment, the reduction, prevention or inhibition of rejection of transplantation or increased transplant survival thereof associated with one or more of each of the above-recited conditions may be about 10-20%, 30-40%, 50-60%, or more due to administration of disclosed compositions herein.

In one embodiment of the present invention a composition may include compounds that engage molecules for the SEC receptor to treat a subject undergoing a transplantation and/or in need of immunotolerance therapy. In each of the recited methods, an AAT-mutant or AAT derived peptide (e.g. mammalian derived) having no significant derine protease inhibitor activity contemplated for use within the methods of the present invention can include a series of peptides including carboxyterminal amino acid peptides corresponding to AAT. Among this series of peptides, some include, but are not limited to pentamers or pentameric derivatives of an AAT region, including, but not limited to, FVFLM (SEQ ID NO. 1), FVFAM (SEQ. ID NO. 2), FVALM (SEQ. ID NO. 3), FVFLA (SEQ. ID NO. 4), FLVFI (SEQ. ID NO. 5), FLMII (SEQ. ID NO. 6), FLFVL (SEQ. ID NO. 7), FLFVV (SEQ. ID NO. 8), FLFLI (SEQ. ID NO. 9), FLFFI (SEQ. ID NO. 10), FLMFI (SEQ. ID NO. 11), FMLLI (SEQ. ID NO. 12), FIIMI (SEQ. ID NO. 13), FLFCI (SEQ. ID NO. 14), FLFAV (SEQ. ID NO. 15), FVYLI (SEQ. ID NO. 16), FAFLM (SEQ. ID NO. 17), AVFLM (SEQ. ID NO. 18), and any combination thereof.

In several embodiments herein, AAT peptides contemplated for use in the compositions and methods of the present invention are also intended to include any and all of those specific AAT peptides of SEQ ID NO. 61 depicted supra. Any combination of consecutive amino acids simulating AAT having no significant serine protease activity or AAT-mutant having no significant serine protease activity or AAT-peptide having no significant serine protease activity may be used, such as amino acids 2-12, amino acids 3-14, 4-16, etc. In addition, combinations of amino acid 5-mers or 10-mers or 20-mers or 30-mers or more can also be used. For example any combinations of 5-mers or 10-mers from SEQ ID NO. 61 AA from 315 to 394 can be used in compositions contemplated herein. Another example is SEQ ID NOs 45 through 60 below may be combined in a composition contemplated herein or made into concatamers and provided in a composition having no significant serine protease inhibitor activity.

As contemplated herein, the last amino acid is the carboxyl terminus. In certain embodiments, the carboxyl domain of AAT going backwards from the carboxyl terminus is defined as those amino acids most conserved among the difference species and do not participate in the protease binding domain of AAT. In addition, in other embodiments, AAT protease binding domain can be mutated in order to reduce or eliminate the protease function of the molecule (see for example pEF-hAAT) and not inhibit elastase activity and this molecule can be used in any composition contemplated herein. In certain embodiments, the mutated AAT or AAT derived peptides can be used to protect islet cells before, after, and/or during transplantation either supplied directly to the islets and/or administered to a subject in need of islet cell infusion. In other embodiments, the mutated molecule retains its an anti-inflammatory effects and can be used as an anti-inflammatory molecule in a subject having an autoimmune condition or undergoing a transplant. It is also contemplated herein that the carboxyl domain is the non-protease binding domain. One skilled in the art would understand a non-protease binding domain of AAT.

In each of the above-recited methods, AAT or analogs thereof are contemplated for use in a composition herein. These analogs may include peptides. The peptides may include but are not limited to amino acid peptides of 10-mers containing one or more of MPSSVSWGIL (SEQ. ID NO. 19); LAGLCCLVPV (SEQ. ID NO. 20) SLAEDPQGDA (SEQ. ID NO. 21); AQKTDTSHHD (SEQ. ID NO. 22) QDHPTFNKIT (SEQ. ID NO. 23); PNLAEFAFSL (SEQ. ID NO. 24); YRQLAHQSNS (SEQ. ID NO. 25); TNIFFSPVSI (SEQ. ID NO. 26); ATAFAMLSLG (SEQ. ID NO. 27); TKADTHDEIL (SEQ. ID NO. 28); EGLNFNLTEI (SEQ. ID NO. 29); PEAQIHEGFQ (SEQ. ID) NO. 30); ELLRTLNQPD (SEQ. ID NO. 31); SQLQLTTGNG (SEQ. ID NO. 32); LFLSEGLKLV (SEQ. ID NO. 33); DKFLEDVKKL (SEQ. ID NO. 34); YHSEAFTVNF (SEQ. ID NO. 35); GDHEEAKKQI (SEQ. ID NO. 36); NDYVEKGTQG (SEQ. ID NO. 37); KIVDLVKELD (SEQ. ID NO. 38); RDTVFALVNY (SEQ. ID NO. 39); IFFKGKWERP (SEQ. ID NO. 40); FEVKDTEDED (SEQ. ID NO. 41); FHVDQVTTVK (SEQ. ID NO. 42); VPMMKRLGMF (SEQ. ID NO. 43); NIQHCKKLSS (SEQ. ID NO. 44); WVLLMKYLGN (SEQ. ID NO. 45); ATAIFFLPDE (SEQ. ID NO. 46); GKLQHLENEL (SEQ. ID NO. 47); THDIITKFLE (SEQ. ED NO. 48); NEDRRSASLH (SEQ. ID NO. 49); LPKLSITGTY (SEQ. ID NO. 50); DLKSVLGQLG (SEQ. ID NO. 51); ITKVFSNGAD (SEQ. ID NO. 52); LSGVTEEAPL (SEQ. ID NO. 53); KLSKAVHKAV (SEQ. ID NO. 54); LTIDEKGTEA (SEQ. ID NO. 55); AGAMFLEAIP (SEQ. ID NO. 56); MSIPPEVKFN (SEQ. ID NO. 57); KPFVFLMIEQ (SEQ. ID NO. 58); NTKSPLFMGK (SEQ. ID NO. 59); VVNPTQK (SEQ. ID NO. 60), or any combination thereof.

In accordance with embodiments of the present invention, the peptide can be protected or derivatized in by any means known in the art for example, N-terminal acylation, C-terminal amidation, cyclization, etc. In a specific embodiment, the N-terminus of the peptide is acetylated.

Other embodiments concern mutants of human. AAT where the mutant is generated to have no significant serine protease inhibitor activity. Any method known in the art for generating mutants is contemplated. Some embodiments include using site-directed mutageneis to generate an hATT having no significant serine protease inhibitor activity (see Examples section and pEF-hAAT). Other methods include disrupting the serine protease inhibiting region of hAAT by other disruption methods such as heating hAAT or chemically modifying hAAT to eliminate or dramatically reduce serine potease inhibitor activity or the molecule.

Pharmaceutical Compositions

Embodiments herein provide for administration of compositions to subjects in a biologically compatible form suitable for pharmaceutical administration in vivo. By "biologically compatible form suitable for administration in vivo" is meant a form of the active agent (i.e. pharmaceutical chemical, protein, gene, antibody etc of the embodiments) to be administered in which any toxic effects are outweighed by the therapeutic effects of the active agent. Administration of a therapeutically active amount of the therapeutic compositions is defined as an amount effective, at dosages and for periods of time necessary to achieve the desired result. For example, a therapeutically active amount of a compound may vary according to factors such as the disease state, age, sex, and weight of the individual, and the ability of antibody to elicit a desired response in the individual. Dosage regima may be adjusted to provide the optimum therapeutic response.

In one embodiment, the compound (i.e. pharmaceutical chemical, protein, peptide etc. of the embodiments) may be administered in a convenient manner such as subcutaneous, intravenous, by oral administration, inhalation, transdermal application, intravaginal application, topical application, intranasal or rectal administration. Depending on the route of administration, the active compound may be coated in a material to protect the compound from the degradation by enzymes, acids and other natural conditions that may inactivate the compound. In a preferred embodiment, the compound may be orally administered. In another preferred embodiment, the compound may be administered intravenously. In one particular embodiment, the compound may be administered intranasally, such as inhalation.

A compound may be administered to a subject in an appropriate carrier or diluent, co-administered with enzyme inhibitors or in an appropriate carrier such as liposomes. The term "pharmaceutically acceptable carrier" as used herein is intended to include diluents such as saline and aqueous buffer solutions. It may be necessary to coat the compound with, or co-administer the compound with, a material to prevent its inactivation. The active agent may also be administered parenterally or intraperitoneally. Dispersions can also be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use may be administered by means known in the art. For example, sterile aqueous solutions (where water soluble) or dispersions and sterile powders for the extemporaneous preparation of sterile injectable solutions or dispersion may be used. In all cases, the composition cant be sterile and can be fluid to the extent that easy syringability exists. It might be stable under the conditions of manufacture and storage and may be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that reduces serine protease activity) in the required amount in an appropriate solvent with one or a combination of ingredients enumerated above, as required, followed by filtered sterilization.

Aqueous compositions can include an effective amount of a therapeutic compound, peptide, epitopic core region, stimulator, inhibitor, and the like, dissolved or dispersed in a pharmaceutically acceptable carrier or aqueous medium. Compounds and biological materials disclosed herein can be purified by means known in the art.

Solutions of the active compounds as free-base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. Prolonged absorption of the injectable compositions can be brought about by the use in the compositions of agents delaying absorption, for example, aluminum monostearate and gelatin.

Upon formulation, solutions will be administered in a manner compatible with the dosage formulation and in such amount as is therapeutically effective. The formulations are easily administered in a variety of dosage forms, such as the type of injectable solutions described above. It is contemplated that slow release capsules, timed-release microparticles, and the like can also be employed. These particular aqueous solutions are especially suitable for intravenous, intramuscular, subcutaneous and intraperitoneal administration.

The active therapeutic agents may be formulated within a mixture to comprise about 0.0001 to 1.0 milligrams, or about 0.001 to 0.1 milligrams, or about 0.1 to 1.0 or even about 1 to 10 gram per dose. Single dose or multiple doses can also be administered on an appropriate schedule for a predetermined condition.

In another embodiment, nasal solutions or sprays, aerosols or inhalants may be used to deliver the compound of interest. Additional formulations that are suitable for other modes of administration include suppositories and pessaries. A rectal pessary or suppository may also be used. In general, for suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and the like. In certain defined embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such therapeutically useful compositions is such that a suitable dosage will be obtained.

A pharmaceutical composition may be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

Pharmaceutical compositions are administered in an amount, and with a frequency, that is effective to inhibit or alleviate side effects of a transplant and/or to reduce or prevent rejection. The precise dosage and duration of treatment may be determined empirically using known testing protocols or by testing the compositions in model systems known in the art and extrapolating therefrom. Dosages may also vary with the severity of the condition. A pharmaceutical composition is generally formulated and administered to exert a therapeutically useful effect while minimizing undesirable side effects. In general, an oral dose ranges from about 200 mg to about 1000 mg, which may be administered for example 1 to 3 times per day.

It will be apparent that, for any particular subject, specific dosage regimens may be adjusted over time according to the individual need. The preferred doses for administration can be anywhere in a range between about 0.01 mg and about 100 mg per ml of biologic fluid of treated patient. In one particular embodiment, the range can be between 1 and 100 mg/kg which can be administered daily, every other day, biweekly, weekly, monthly etc. In another particular embodiment, the range can be between 10 and 75 mg/kg introduced weekly to a subject. The therapeutically effective amount of α1-antitrypsin, peptides, or drugs that have similar activities as α1-antitrypsin or peptides can be also measured in molar concentrations and can range between about 1 nM to about 2 mM.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent.

Liposomes can be used as a therapeutic delivery system and can be prepared in accordance with known laboratory techniques. In addition, dried lipids or lyophilized liposomes prepared as previously described may be reconstituted in a solution of active agent (e.g. nucleic acid, peptide, protein or chemical agent), and the solution diluted to an appropriate concentration with a suitable solvent known to those skilled in the art. The amount of active agent encapsulated can be determined in accordance with standard methods.

In a one embodiment, a nucleic acid (e.g. α1-antitrypsin or analogs thereof) and the lipid dioleoylphosphatidylcholine may be employed. For example, nuclease-resistant oligonucleotides may be mixed with lipids in the presence of excess t-butanol to generate liposomal-oligonucleotides for administration.

Pharmaceutical compositions containing AAT having no significant serine protease inhibitor activity, analog thereof, or a functional derivative thereof may be administered to individuals, particularly humans, for example by subcutaneously, intramuscularly, intranasally, orally, topically, transdermally, parenterally, gastrointestinally, transbronchially and transalveolarly. Topical administration is accomplished via a topically applied cream, gel, rinse, etc. containing therapeutically effective amounts of inhibitors of serine proteases. Transdermal administration is accomplished by application of a cream, rinse, gel, etc. capable of allowing the inhibitors of serine proteases to penetrate the skin and enter the blood stream. In addition, osmotic pumps may be used for administration. The necessary dosage will vary with the particular condition being treated, method of administration and rate of clearance of the molecule from the body.

In each of the aforementioned compositions and methods, a compound having no significant serine protease inhibitor activity but having other α1-antitrypsin activity or analog thereof may be used in a single therapeutic dose, acute manner or a chronic manner to treat episodes or prolonged bouts, respectively, in reducing or eliminating a medical disorder contemplated herein.

In certain embodiments of the methods of the present invention, the subject may be a mammal such as a human or a veterinary and/or a domesticated animal.

Therapeutic Methods

In one embodiment of the present invention, methods provide for treating a subject in need of or undergoing a transplant. For example, treatments for reducing graft rejection, promoting graft survival, and promoting prolonged graft function by administering to a subject in need thereof a therapeutically effective amount of a composition.

Preserving the Graft During Transplant Before Engraftment

According to the methods of the present invention, transplantation complications can be reduced or inhibited to obtain important therapeutic benefits. Therefore, administration of a therapeutic composition contemplated by embodiments of the present invention, e.g., AAT having no significant serine protease inhibitor activity, derivative or peptide or mutant or analog having no significant serine protease inhibitor activity thereof, can be beneficial for the treatment of transplantation complications or conditions.

Another beneficial effect of use of the compositions and methods disclosed include reducing negative effects on an organ or non-organ during explant, isolation, transport and/or prior to implantation. For example, the composition can reduce apoptosis, reduce production of cytokines, reduce production of NO, or combination thereof in an organ for transplant. In one particular embodiment, a composition can include a compound that includes alpha-1-antitrypsin, an analog thereof, a serine protease inhibitor, serine protease inhibitor-like activity, analog thereof or a combination thereof. The transplant organ or non-organ can include but is not limited to, lung, kidney, heart, liver, soft tissue, skin, pancreas, intestine, soft tissue cornea, bone marrow, stem cell, pancreatic islet, and combination thereof.

In a further embodiment, the methods and compositions are useful in the therapeutic treatment of graft rejection associated side effects. In a yet further embodiment, graft rejection associated side effects can be prevented by the timely administration of the agent of the invention as a prophylactic, prior to onset of one or more symptoms, or one or more signs, or prior to onset of one or more severe symptoms or one or more signs of a graft rejection associated disease. Thus, a patient at risk for a particular graft rejection or graft rejection-associated disease or clinical indication can be treated with serine protease inhibitors, for example, (Benzyloxycarbonyl)-L-Valyl-N-[1-(3-(5-(3-Trifluoromethylbenzyl)-1,2,4-oxadiazolyl)carbonyl)-2-(S)-Methylpropyl]-L-Prolinamide; as a prophylactic measure.

It is contemplated herein that compositions and methods can be used to treat patients with one or more grafts who require chronic therapy to maintain graft integrity, and such patients will therefore benefit from indefinite or chronic use of the rejection repressive therapy of the methods of the present invention. Yet another embodiment can be used to treat flairs of acute rejection so as to minimize the effects of acute clinical rejection, organ failure, and/or eventual destruction of the graft.

Desirable blood levels may be maintained by continuous infusion to provide about 0.01-5.0 mg/kg/hr or by intermittent infusions containing about 0.4-20 mg/kg of the active ingredient(s). Buffers, preservatives, antioxidants and the like can be incorporated as required. It is intended herein that the ranges recited also include all those specific percentage amounts between the recited range. For example, the range of about 0.4 to 20 mg/kg also encompasses 0.5 to 19.9%, 0.6 to 19.8%, etc, without actually reciting each specific range therewith.

Management of Graft Rejection

By preventing or reducing the side effects or conditions associated with graft survival or graft rejection using this novel approach, several advantages are obtained compared to alternative approaches, for example, and not by way of limitation:

Reduced infiltration of graft with cells or serum factors (for example, and not by way of limitation, complement, anti graft antibody that generate inflammation and graft rejection); reduced production of cytokines or nitric oxide (NO) that can induce inflammation or apoptosis; inhibits apoptosis; inhibits immune activation, inhibits CMV or any combination thereof.

Commercially available agents already approved for different use in humans will work as a treatment for graft rejection and/or promote graft survival. These agents are currently used for indications other than graft rejection and/or to promote graft survival, and include injectable AAT, plasma preparations, aprotinin and others (American J. of Resp Critical Care Med 1998, VII 158: 49-59, incorporated herein by reference in its entirety). In one embodiment, compositions contemplated herein may be delivered by inhalation. This mode of focused drug delivery may augment serine protease inhibitor activity within the lung tissues and associated lymphatics, which are two of the principal sites where diseases and/or clinical conditions associated with graft rejection and/or promotion of graft survival develop.

Isolated Proteins

One aspect of the invention pertains to proteins, and portions thereof, as well as polypeptide fragments suitable for use as immunogens to raise antibodies directed against a polypeptide of the invention. In one embodiment, the native polypeptide can be isolated from cells or tissue sources by an appropriate purification scheme using standard protein purification techniques and then the serine protease inhibitor activity can be dramatically reduced or eliminated. In another embodiment, polypeptides can be produced by recombinant DNA techniques. Alternative to recombinant expression, a polypeptides can be synthesized chemically using standard peptide synthesis techniques.

One embodiment pertains to isolated proteins, and biologically active portions thereof, as well as polypeptide fragments. In one embodiment, the native polypeptide can be isolated from cells or tissue sources by an appropriate purification scheme using standard protein purification techniques. In certain embodiments, the native polypeptide may be heated or otherwise treated to reduce or eliminate serine protease inhibitor activity. In certain particular embodiments, serine protease inhibitor activity is reduced where no significant activity remains. In another embodiment, polypeptides contemplated herein are produced by recombinant DNA techniques. Alternative to recombinant expression, a polypeptide can be synthesized chemically using standard peptide synthesis techniques. Any of the peptide or protein molecules contemplated of use in compositions disclosed herein can be compositions having no significant serine protease inhibitor activity. For example, AAT compositions may be treated in order to reduce or eliminate serine protease inhibitor activity or an AAT polypeptide may be isolated wherein the polypeptide has reduced or no significant serine protease inhibitor activity.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium. When the protein is produced by chemical synthesis, it is preferably substantially free of chemical precursors or other chemicals. For example, such preparations of the protein have less than about 30%, 20%, 10%, 5% (by dry weight) of chemical precursors or compounds other than the polypeptide of interest.

In certain embodiments, polypeptides can include a polypeptide having an amino acid sequence corresponding to the carboxy terminus of AAT or AAT allele. Other useful proteins are substantially identical (e.g., at least about 45%, preferably 55%, 65%, 75%, 85%, 95%, or 99%) to any portion of the carboxy terminus, and retain the functional activity of the protein of the corresponding naturally-occurring protein other than serine protease inhibitor activity yet differ in amino acid sequence due to natural allelic variation or mutagenesis.

Compounds herein can be used as therapeutic agents in the treatment of a physiological (especially pathological) condition caused in whole or part, by excessive serine protease activity. In addition, a physiological (especially pathological) condition can be inhibited in whole or part. Peptides contemplated herein may be administered as free peptides or pharmaceutically acceptable salts thereof. Peptides may be administered to a subject as a pharmaceutical composition, which, in most cases, will include the peptide and/or pharmaceutical salts thereof with a pharmaceutically acceptable carrier.

When utilizing BLAST, Gapped BLAST, and PSI-Blast programs, the default parameters of the respective programs (e.g., XBLAST and NBLAST) can be used.

Variants of the polypeptides are contemplated herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein may inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein contemplated herein which function as either agonists (mimetics) or as antagonists can be identified by screening combinatorial libraries of mutants, e.g., truncation mutants, of the protein of the invention for agonist or antagonist activity.

Biologically active portions of a polypeptide of the invention include polypeptides including amino acid sequences sufficiently identical to or derived from the amino acid sequence of the protein (e.g., the amino acid sequence shown in any of SEQ ID Nos: 1 to 61, which exhibit at least one activity of the corresponding full-length protein). A biologically active portion of a protein of the invention can be a polypeptide, which is, for example, 5, 10, 25, 50, 100 or more amino acids in length. Moreover, other biologically active portions having no significant serine protease inhibitor activity, in which other regions of the protein are deleted, can be prepared by recombinant techniques and evaluated for one or more of the functional activities of the native form of a polypeptide of the invention.

Preferred polypeptides have the amino acid sequence of SEQ ID Nos: 1 to 61. Other useful proteins are substantially identical (e.g., at least about 45%, preferably 55%, 65%, 75%, 85%, 95%, or 99%) to any of SEQ ID NOs: 1 to 61.

Variants of AAT molecules having no significant serine protease activity can be generated by mutagenesis, e.g., discrete point mutation or truncation. An agonist can retain substantially the same, or a subset, of the biological activities of the naturally occurring form of the protein except no significant serine protease activity remains. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a protein of the invention which function as either agonists (mimetics) or as antagonists can be identified by screening combinatorial libraries of mutants, e.g., truncation mutants, of the protein of the invention for agonist or antagonist activity.

Fusion Polypeptides

In other embodiments, compounds having AAT activity other than serine protease inhibitor activity, such as AAT and/or analog thereof, may be part of a fusion polypeptide. In one example, a fusion polypeptide may include AAT (e.g. mammalian α1-antitrypsin) or an analog thereof and a different amino acid sequence that may be heterologous to AAT or analog substance, having no significant serine protease inhibitor activity.

In yet other embodiments, a fusion polypeptide (e.g., IgG or fragment thereof) contemplated of use in methods herein can additionally include an amino acid sequence that is useful for identifying, tracking or purifying the fusion polypeptide, e.g., a FLAG or HIS tag sequence. The fusion polypeptide can include a proteolytic cleavage site that can remove the heterologous amino acid sequence from the compound capable of serine protease inhibition, such as mammalian AAT or analog thereof.

In one embodiment, fusion polypeptides can be produced by recombinant DNA techniques. Alternative to recombinant expression, a fusion polypeptide of the invention can be synthesized chemically using standard peptide synthesis techniques. In addition, a fusion polypeptide disclosed herein can include a pharmaceutically acceptable carrier, excipient or diluent.

In certain embodiments, a fusion protein can include a heterologous sequence derived from a member of the immunoglobulin protein family, for example, an immunoglobulin constant region, e.g., a human immunoglobulin constant region such as a human IgG1 constant region. A fusion protein can, for example, include a portion of AAT, analog thereof fused with the amino-terminus or the carboxyl-terminus of an immunoglobulin constant region, by methods known in the art. In accordance with these embodiments, the FcR region of the immunoglobulin may be either wild-type or mutated. In certain embodiments, it may be desirable to utilize an immunoglobulin fusion protein that does not interact with an Fc receptor and does not initiate ADCC reactions. In such instances, the immunoglobulin heterologous sequence of the fusion protein can be mutated to inhibit such reactions. See for example, U.S. Pat. No. 5,985,279 and WO 98/06248.

In yet another embodiment, AAT, analog thereof, polypeptide fusion protein can be a GST fusion protein in which is fused to the C-terminus of GST sequences. Fusion expression vectors and purification and detection means are known in the art.

Expression vectors can routinely be designed for expression of a fusion polypeptide of the invention in prokaryotic (e.g., E. coli) or eukaryotic cells (e.g., insect cells (using baculovirus expression vectors), yeast cells or mammalian cells) by means known in the art.

Expression of proteins in prokaryotes may be carried out by means known in the art. Such fusion vectors typically serve three purposes: 1) to increase expression of recombinant protein; 2) to increase the solubility of the recombinant protein; and 3) to aid in the purification of the recombinant protein by acting as a ligand in affinity purification.

In yet another embodiment, a nucleic acid of the invention is expressed in mammalian cells using a mammalian expression vector as described in the art. In another embodiment, a recombinant mammalian expression vector is capable of directing expression of the nucleic acid in a particular cell type (e.g., tissue-specific regulatory elements are used to express the nucleic acid) such as pancreas-specific promoters and mammary gland-specific promoters. A host cell can be any prokaryotic (e.g., E. coli) or eukaryotic cell (e.g., insect cells, yeast or mammalian cells). Vector DNA can be introduced into prokaryotic or eukaryotic cells via conventional transformation or transfection techniques.

Some embodiments contemplated herein include adding and/or deleting groups from alpha-1 antitrypsin, a fragment thereof, an analog thereof, or fusion molecule thereof. In accordance with these embodiments, these molecules may be deglycoslyated prior to use in methods disclosed herein. In other embodiments stabilizing compounds may be linked to the molecules to increase stability when used in methods disclosed herein. For example, PEG (polyethylene glycol) may be added to increase stabilization of compositions contemplated herein.

Combination Therapies

Any of the embodiments detailed herein may further include one or more a therapeutically effective amount of anti-microbial drugs, anti-inflammatory agent, immunomodulatory agent, or immunosuppressive agent or combination thereof.

Examples of anti-bacterial agents include, but are not limited to, penicillins, quinolonses, aminoglycosides, vancomycin, monobactams, cephalosporins, carbacephems, cephamycins, carbapenems, and monobactams and their various salts, acids, bases, and other derivatives.

Anti-fungal agents contemplated of use herein can include, but are not limited to, caspofungin, terbinafine hydrochloride, nystatin, amphotericin B, griseofulvin, ketoconazole, miconazole nitrate, flucytosine, fluconazole, itraconazole, clotrimazole, benzoic acid, salicylic acid, and selenium sulfide.

Anti-viral agents contemplated of use herein can include, but are not limited to, valgancyclovir, amantadine hydrochloride, rimantadin, acyclovir, famciclovir, foscamet, ganciclovir sodium, idoxuridine, ribavirin, sorivudine, trifluridine, valacyclovir, vidarabin, didanosine, stavudine, zalcitabine, zidovudine, interferon alpha, and edoxudine.

Anti-parasitic agents contemplated of use herein can include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole, (sulfamethoxazole/trimethoprim), and pentamidine isethionate.

Immunomodulatory agents can include for example, agents which act on the immune system, directly or indirectly, by stimulating or suppressing a cellular activity of a cell in the immune system, (e.g., T-cells, B-cells, macrophages, or antigen presenting cells (APC)), or by acting upon components outside the immune system which, in turn, stimulate, suppress, or modulate the immune system (e.g., hormones, receptor agonists or antagonists, and neurotransmitters); other immunomodulatory agents can include immunosuppressants or immunostimulants. Anti-inflammatory agents can include, for example, agents which treat inflammatory responses, tissue reaction to injury, agents which treat the immune, vascular, or lymphatic systems or any combination thereof.

Anti-inflammatory or immunomodulatory drugs or agents contemplated of use herein can include, but are not limited to, interferon derivatives, e.g., betaseron, β-interferon; prostane derivatives, iloprost, cicaprost; glucocorticoids such as cortisol, prednisolone, methylprednisolone, dexamethasone; immunsuppressive agents such as cyclosporine A, FK-506, methoxsalene, thalidomide, sulfasalazine, azathioprine, methotrexate; lipoxygenase inhibitors, e.g., zileuton, MK-886, WY-50295, SC-45662, SC-41661A, BI-L-357; leukotriene antagonists; peptide derivatives for example ACTH and analogs; soluble TNF (tumor necrosis factor)-receptors; TNF-antibodies; soluble receptors of interleukines, other cytokines, T-cell-proteins; antibodies against receptors of interleukins, other cytokines, and T-cell-proteins.

Other agents of use in combination with compositions herein can be molecules having serine protease inhibitor activity. For example serine protease inhibitors contemplated of use herein can include, but are not limited to, leukocyte elastase, thrombin, cathepsin G, chymotrypsin, plasminogen activators, and plasmin.

In certain embodiments, a composition may include one or more peptides of an AAT or AAT analog where the peptide(s) have similar activity to an AAT or AAT analog having no significant serine protease inhibitor activity. In each of the recited methods, an α1-antitrypsin (e.g. mammalian derived) substance having no significant serine protease inhibitor activity contemplated for use within methods disclosed herein can include a series of peptides including carboxyterminal or amino terminal amino acid peptides corresponding to or derived from any AAT molecule contemplated herein. In certain embodiments, the peptides can be 5 or 10 or 20 or 30 or 40 or more amino acids in length.

In other particular embodiments herein, AAT peptides contemplated for use in the compositions and methods of the present invention are also intended to include any and all of those specific AAT peptides depicted supra. Any combination of consecutive amino acids simulating AAT having no significant serine protease inhibitor activity may be used, such as amino acids 2-12, amino acids 3-14, 4-16, 5-20, 10-30, etc.

In addition, other combination compositions of methods disclosed herein can include certain antibody-based therapies. Non-limiting examples include, polyclonal anti-lymphocyte antibodies, monoclonal antibodies directed at the T-cell antigen receptor complex (OKT3, TIOB9), monoclonal antibodies directed at additional cell surface antigens, including interleukin-2 receptor alpha. In certain embodiments, antibody-based therapies may be used as induction therapy in combination with the compositions and methods disclosed herein.

Subjects contemplated herein can include human subjects, or other subjects such as non-human subjects, including but not limited to, primates, dogs, cats, horses, cows, pigs, guinea pigs, birds and rodents.

AAT

Human AAT is a single polypeptide chain with no internal disulfide bonds and only a single cysteine residue normally intermolecularly disulfide-linked to either cysteine or glutathione. One reactive site of AAT contains a methionine residue, which is labile to oxidation upon exposure to tobacco smoke or other oxidizing pollutants. Such oxidation reduces the elastase-inhibiting activity of AAT; therefore substitution of another amino acid at that position, e.g., alanine, valine, glycine, phenylalanine, arginine or lysine, produces a form of AAT which is more stable. Native AAT can be represented by the following formula:

```
EDPQGDAAQKTDTSHHDQDHPTFNKITPNLAEFAFSLYRQLAHQSNSTNIFFSPVS    (SEQ ID NO: 61)

IATAFAMLSLGTKADTHDEILEGLNFNLTEIPEAQIHEGFQELLRTLNQPDSQLQLTTGN

GLFLSEGLKLVDKFLEDVKKLYHSEAFTVNFGDTEEAKKQINDYVEKGTQ

GKIVDLVKELDRDTVFALVNYIFFKGKWERPFEVKDTEEEDFHVDQVTTVKVPMMKRLGM

FNIQHCKKLSSWVLLMKYLGNATAIFFLPDEGKLQHLENELTHDIITKFLENEDRRSASL

HLPKLSITGTYDLKSVLGQLGITKVFSNGADLSGVTEEAPLKLSKAVHKAVLTIDEKGTE

AAGAMFLEAIPMSIPPEVKFNKPFVFLMIEQNTKSPLFMGKVVNPTQK.
```

Extra hepatic sites of AAT production include neutrophils, monocytes and macrophages, and the expression of AAT is inducible in response to LPS, TNFα, IL-1 and IL-6 in various cell types. Deficiency in AAT is associated with immune dysfunctional conditions such as rheumatoid arthritis and systemic lupus erythematosus.

In one embodiment, with respect to the use of the compositions and methods of the present invention to prevent or reduce graft rejection or transplant rejection specifically excluded within the scope of the present invention are those furin endoprotease inhibitors comprising an AAT variant having an amino acid sequence comprising the amino acids of the native AAT molecule, except that the sequence at position 355-358 of the native protein (-Ala-Ile-Pro-Met-) is changed to the novel sequence -Arg-X-X-Arg-, wherein X is any amino acid, at positions 355-358 of the native .alpha.sub.1-antitrypsin amino acid sequence as disclosed in U.S. Pat. Nos. 5,604,201 and 6,022,855.

Also specifically excluded within the scope of the compositions and methods with respect to the use of the compositions and methods of the present invention to prevent or reduce graft rejection or transplant rejection specifically are AAT Portland variants wherein the amino acid sequence at positions 355-358 of the AAT Portland sequence is -Arg-Ile-Pro-Arg- as disclosed in U.S. Pat. Nos. 5,604,201 and 6,022,855.

Also specifically excluded within the scope of the compositions and methods with respect to the use of the compositions and methods of the present invention to prevent or reduce graft rejection or transplant rejection specifically are AAT are peptides having amino acid sequences comprising the amino acid sequence -Arg-Xaa-Xaa-Arg- at positions 355-358, wherein each Xaa is any amino acid as is disclosed in U.S. Pat. Nos. 5,604,201 and 6,022,855.

Kits

In still further embodiments, kits for use with the methods described above are contemplated. Kits may include a mutant AAT composition, a mutant AAT molecule associated with a gene therapy delivery system or other combinations. Small molecules, proteins or peptides may be employed for use in any of the disclosed methods. In addition, other agents such as anti-bacterial agents, immunosuppressive agents, anti-inflammatory agents may be provided in the kit. The kits will thus can include, in suitable container means, a protein or a peptide or analog agent, and optionally one or more additional agents.

The kits may further include a suitably aliquoted composition of the encoded protein or polypeptide antigen, whether labeled or unlabeled, as may be used to prepare a standard curve for a detection assay.

The container means of the kits will generally include at least one vial, test tube, flask, bottle, syringe or other container means. A kit will also generally contain a second, third or other additional container into which other combination agents may be placed. Such containers may include injection or blow-molded plastic containers into which the desired vials are retained.

In certain embodiments, a kit can include a composition including, but not limited to, AAT, AAT fragment, or an AAT analog or polypeptide, having no significant serine protease inhibitor activity. In accordance with these embodiments, a kit can contain AAT or an analog thereof having no significant serine protease inhibitor activity.

EXAMPLES

The following examples are included to illustrate various embodiments. It should be appreciated by those of skill in the art that the techniques disclosed in the examples which follow represent techniques discovered to function well in the practice of the claimed methods, compositions and apparatus. However, those of skill in the art should, in light of the present disclosure, appreciate that changes may be made in the specific embodiments which are disclosed and still obtain a like or similar result without departing from the spirit and scope of the invention.

Example 1

Alpha-1-Antitrypsin Prolongs Graft Islet Graft Survival in Mice

FIG. 1A-1D. Islets from DBA/2 mice (H-2d) were transplanted under the renal capsule of streptozotocin-induced hyperglycemic C57BL/6 mice (H-2b). (A) Glucose levels from days 6-18. Control consists of mice that were untreated (n=3) or treated from day −1 every 3 days with human albumin (ALB, 6 mg, n=3). Prolonged islet graft survival is observed in mice treated from day −1 every 3 days with human AAT (2 mg, n=10). *P<0.05, P<0.01, *P<0.001 between glucose levels on same day. (B) Treatment protocols. Control and full AAT treatment are described in panel A. Early AAT treatment consists of treatment on days −1, 1 and 3 (2 mg, n=3). Late AAT treatment consists of treatment from day 2 and on every 2 days (2 mg, n=3). Rejection indicates the day that glucose levels exceed 300 mg/dl. (C) Effect of mouse anti-human-AAT antibodies. Dashed line indicates post transplantation glucose levels of a mouse under full AAT treatment protocol (see A, B) that was immunized by multiple administrations of human AAT prior to transplantation (1 representative, n=3). Solid line indicates glucose levels of a non-immunized mouse treated under full AAT treatment protocol (1 representative, n=10). Arrow indicates detection of treatment-induced, anti-human-AAT antibodies in the non-immunized representative mouse. (D) Comparison of day 15 post-transplantation glucose levels in mice that were under full treatment protocol with ALB (n=3) or AAT (non-immunized n=10, immunized n=3). Of the AAT-treated group, antibodies were detected on day 15 in 3/3 immunized mice and in 6/10 non-immunized mice. **P=0.005 between mice that produced antibodies (n=6) and mice that did not produce antibodies (n=4).

Figure 1B:
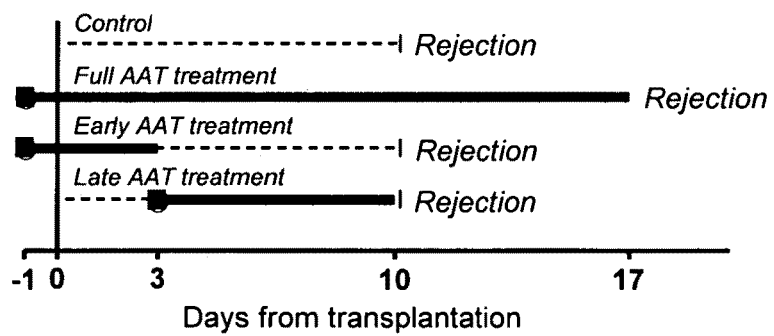

Treatment with human albumin (6 mg) resulted in graft rejection comparable to that of untreated recipient mice. In contrast, recipient mice that received AAT (2 mg) exhibited prolonged graft function. As depicted in FIG. 1b, neither of the partial treatment protocols, i.e., days −1, 1 and 3 ('early treatment') or days 2 and beyond ('late treatment') prolonged allograft survival.

Figure 1C:
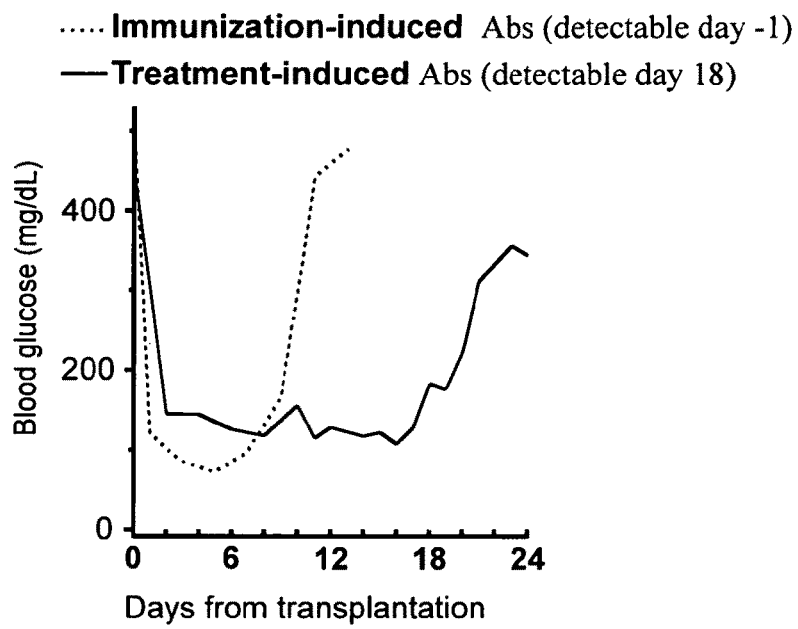
Figure 1D:
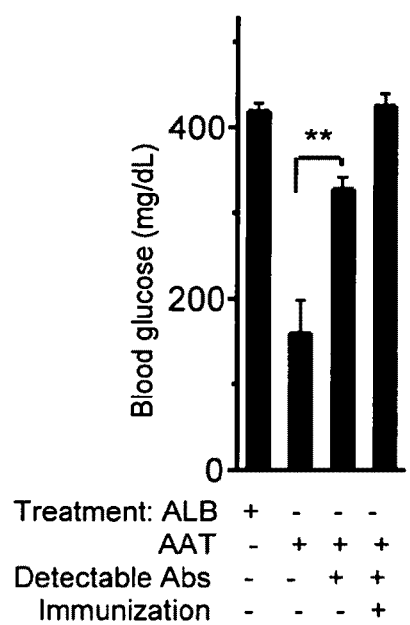

AAT-treated mice developed anti-human-AAT antibodies (FIGS. 1C and D). Individual mice exhibited anti-human-AAT antibodies at various time points (data not shown). To ascertain that the antibodies reduce the protective effect of AAT, a group of mice was pre-exposed ("immunized") to human AAT two months before being rendered hyperglycemic and transplanted with allogeneic islets. These graft recipients were treated with the full AAT protocol, despite exhibiting high titers of specific antibodies before engraftment, and displayed rapid graft rejection (FIG. 1C). Day 15 was chosen to depict an association between antibody formation and loss of AAT protective activity; at this time point AAT-treated mice were divided into positive and negative producers of anti-human-AAT antibodies. As shown in FIG. 1D, on day 15 all antibody-positive mice were hyperglycemic and all antibody-negative mice were normoglycemic.

Example 2

Figures 2A, 2B, 2C, 2D:
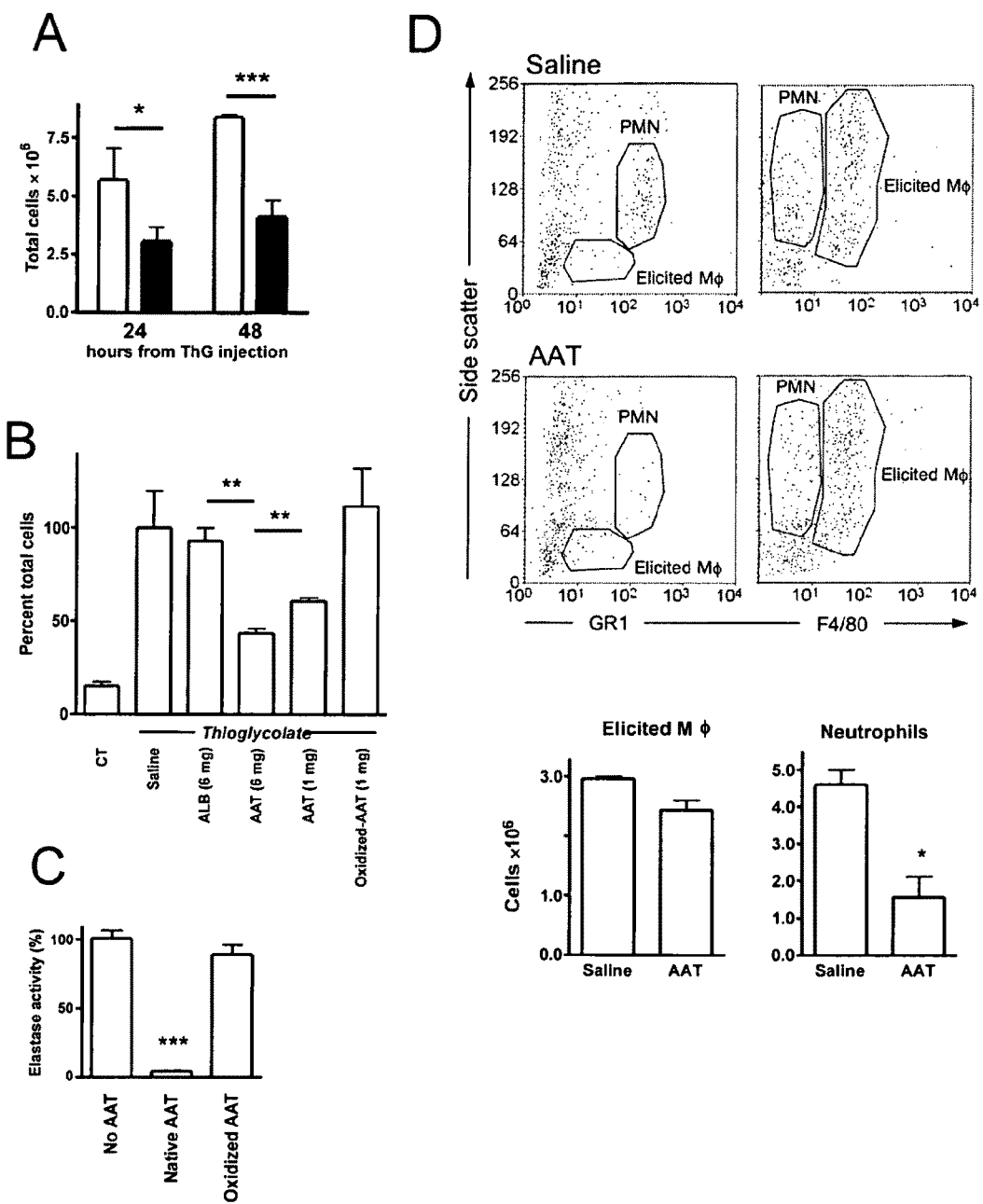
FIGS. 2A-2D illustrates an exemplary method of the effect of AAT on thioglycolate-elicited peritoneal cellular infiltrates. (A) Total cell population of lavaged cells of (O) saline or ( ) AA$^A$-treated (5 mg) thioglycolate-injected mice. (B) Percent cell population from saline-treated mice at 48 hours. (C) Oxidation of AAT. (D) Identification of elicited macrophages and neutrophils.

FIG. 2A-2D illustrates an exemplary method of the effect of AAT on thioglycolate-elicited peritoneal cellular infiltrates. Mice were administered intraperitoneal 0.1 ml saline, ALB, AAT or oxidized-AAT followed by 1 ml of saline or thioglycolate (ThG, 3% w/v, n=3 per group). Peritoneal lavage was performed on separate groups after 24 and 48 hours. (A) Total cell population of lavaged cells of (open bars) saline or (closed bars) AAT-treated (5 mg) thioglycolate-injected mice. P<0.05. (B) Percent cell population from saline-treated mice at 48 hours. P<0.05. (C) Oxidation of AAT. AAT was subjected to oxidative radicals (see Methods). Loss of serine protease activity of oxidized AAT was assessed in an elastase assay. Activity of elastase in the absence of native AAT was set at 100% and the percentage of activity in the presence of native and oxidized AAT was calculated (n=3). ***P<0.001. In FIG. 2D, elicited macrophages and neutrophils are identified. Peritoneal infiltrates from 48 hour lavages of ALB (6 mg) and AAT-treated (6 mg), thioglycolate-injected mice were stained for FACS analysis by specific antibodies. Macrophages and neutrophils were identified on the basis of F4/80 and GR1 versus side scatter flow cytometry profiles. Top, FACS analysis representative graphs (n=3). Quantified FACS results (n=3) are depicted in the bottom.

AAT Inhibits Cellular Infiltration

To address the possibility that AAT affects effector cell infiltration, two models of cell emigration were examined:

thioglycolate (ThG)-elicited peritoneal infiltration, and cellular infiltration due to intraperitoneal injection of MHC-incompatible fibroblasts.

As shown in FIG. 2A, there was a progressive increase in total cell count at 24 and 48 hours in mice injected with ThG, whereas no significant increase was observed in mice injected with AAT and ThG. At 48 hours, total cell count in peritoneal lavage of AAT-treated mice was 50% of that of control (FIG. 2B). Total cell count in mice that received albumin control was similar to that of saline-treated mice. There was a dose-dependent effect of AAT in that one-sixth the dose was found to reduce cell count to a lesser extent in a significant manner. Oxidized AAT, which had lost its in vitro anti-elastase activity (FIG. 2C), did not affect cellular infiltrate at 1 mg (FIG. 2B).

The decrease in total cell count is primarily attributed to a decrease in the number of neutrophils (FIG. 2D), identified by their GR-1 high/intermediate side-scatter (SSC) profile. No major difference was observed with the infiltration of macrophages, identified by their F4/80int, GR-1int, intermediate SSC profile[12], which is distinct from the F4/80very high, GR-1low, high SSC profile of resident macrophages[12] (data not shown).

Example 3

Figure 3A:
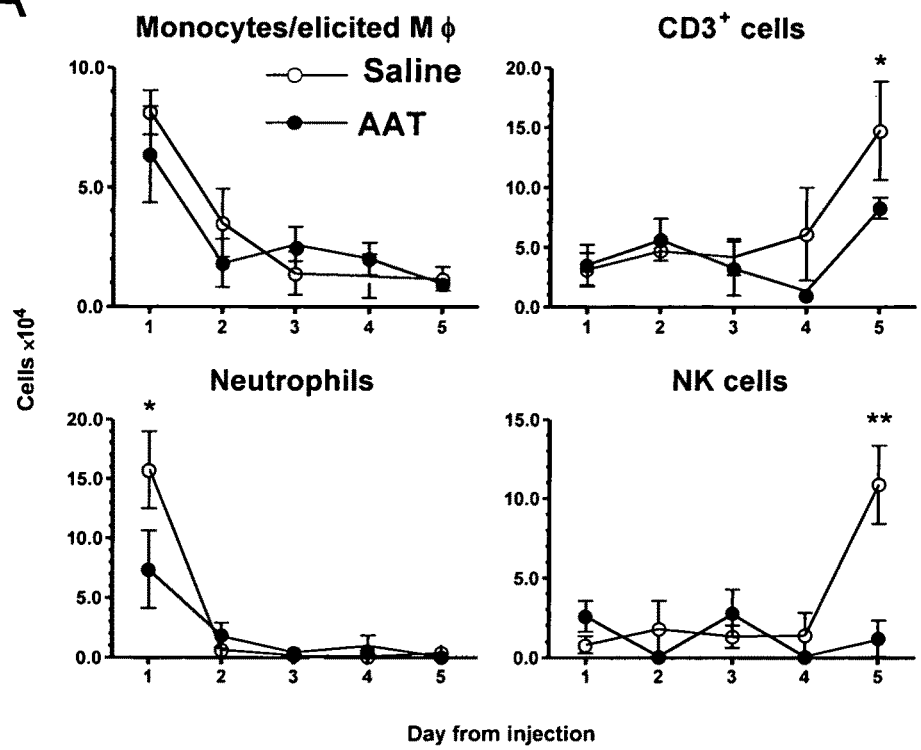
FIGS. 3A-3C illustrates an exemplary method of the effect of AAT on MHC-incompatible, NIH-3T3-fibroblast-elicited peritoneal cellular infiltrates. (A) Cell numbers. The number of cells in each subpopulation was calculated from the percentages obtained by FACS analysis, and total number of cells in the infiltrate. (B) Representative FACS analysis. (C) Effect of AAT on intensity and function of infiltrate elicited by islet allograft. Left, Hematoxilyn and Eosin (H&E) staining of day 7 islet allografts. Right, Immunohistochemistry (IHC) with anti-insulin antibodies of day 15 islet grafts. R, renal parenchyma, G, graft, C, renal capsule.
Figure 3B:
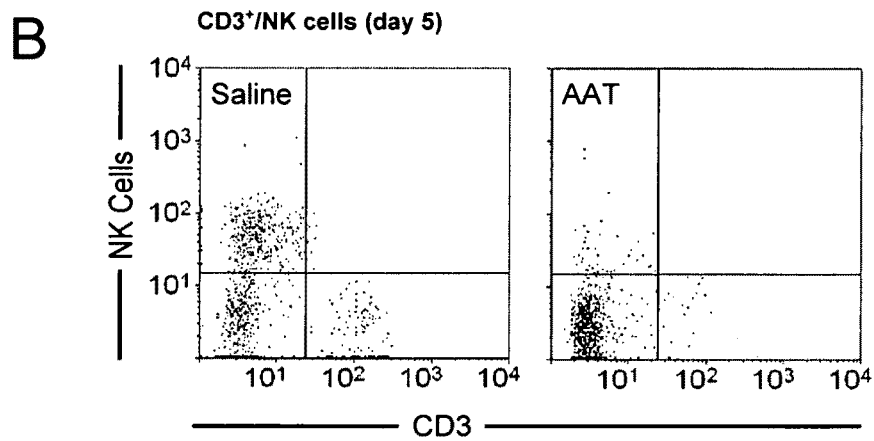
Figure 3C:
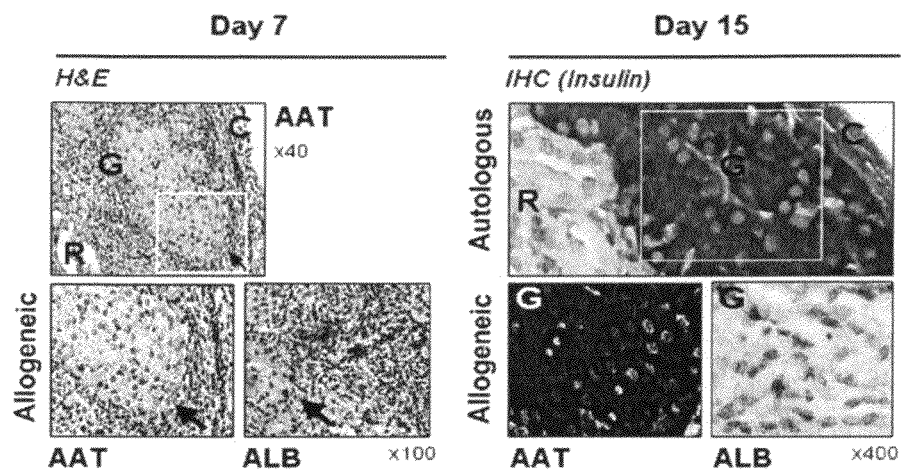

FIG. 3A-3C illustrates an exemplary method of the effect of AAT on MHC-incompatible, NIH-3T3-fibroblast-elicited peritoneal cellular infiltrates. Mice (C57BL/6; H-2b) were injected i.p. 0.1 ml saline or AAT (0.1 mg) followed by 1 ml NIH-3T3 cells (1'107 cells in saline; H-2d). Peritoneal lavage was performed daily on days 1-5 and cell subpopulations were identified by FACS analysis. (n=3 per treatment). (A) Cell numbers. The number of cells in each subpopulation was calculated from the percentages obtained by FACS analysis, and total number of cells in the infiltrate. $*P<0.05$, $**P<0.01$ between cell numbers on the same day. (B) Representative FACS analysis. (C) Effect of AAT on intensity and function of infiltrate elicited by islet allograft. Left, Hematoxilyn and Eosin (H&E) staining of day 7 islet allografts. A section of AAT-treated islet graft (white frame) is compared to a similar section of ALB-treated diabetic recipient mouse (full treatment protocol, see FIG. 1A). Arrow points at border between islet and surrounding infiltrate. Right, Immunohistochemistry (IHC) with anti-insulin antibodies of day 15 islet grafts. A section of autologous islet graft (white frame) is compared to similar sections of allografts of AAT- and ALB-treated recipient mice. R, renal parenchyma, G, graft, C, renal capsule.

As illustrated in FIG. 3A, introduction of allogeneic cells evoked a cellular infiltrate that consisted of early appearing neutrophils and activated macrophages, and late appearing CD3+ and NK cells (FIG. 3B). AAT-treated mice exhibited a reduction in neutrophils, CD3+ and NK cells, dark color is insulin staining.

To evaluate the level of cellular infiltration into grafted islets, grafts from AAT- and ALB-treated recipient mice were removed on day 7, fixed in paraformaldehyde and stained with Hematoxilin and Eosin. As depicted in FIG. 3C (left), a cellular infiltrate is demonstrable regardless of AAT treatment, and includes neutrophils and lymphocytes. However, the infiltrates evoked by grafts of ALB-treated recipient mice were more massive and cause the disruption of islet borders, compared to intact islets of AAT-treated recipient mice. To evaluate islet function, grafts from AAT- and ALB-treated recipient mice were removed on day 15, and immunohistochemistry was performed with anti-insulin antibodies, dark color is insulin staining. As depicted in FIG. 3C (right), insulin production is preserved on day 15 in islets of AAT-treated recipients.

Example 4

FIG. 4A-4H illustrates an exemplary method of the effect of AAT on islet responses. (A-D) Islets from C57BL/6 mice were cultured at 100 islets/well, in duplicate. AAT was incubated at the indicated concentrations for 1 hour before the addition of IFNγ (5 ng/ml) plus IL-1β (10 ng/ml). 72 hours later, supernatants were collected and islet viability was assessed. Islet cells responses in the absence of AAT were set at 100%. Data are combined from 3 individual experiments, in duplicate. $P<0.01$, $*P<0.001$ between AAT-treated and untreated islets. Mean±SEM of a. nitrite levels, b. Cell viability and c. MIP-1α levels. Dashed line represents islets incubated at one-30th the concentration of IFNγ/IL-1β. d. TNFα levels. (E) Insulin induction assay. Islets were incubated in triplicate (20 islets/well) in the presence of AAT (0.5 mg/ml) or ALB (0.5 mg/ml) 1 hour before addition of IFNγ (5 ng/ml) plus IL-1β (10 ng/ml). 24 hours later, islets were transferred to a 3 mM or 20 mM glucose solution for 30 minutes and insulin levels were measured. Vertical axis depicts the ratio between insulin levels at both glucose concentrations. $*P<0.05$ between AAT-treated and ALB-treated islets. (F) Streptozotocin toxicity. C57BL/6 mice were injected i.p. with AAT (5 mg) or saline, one day before, on same day and one day after injection of streptozotocin (225 mg/kg) or saline (n=3 per group). 48 hours later, pancreata were removed and insulin-containing cells were identified by immunohistochemistry. Each image depicts a representative islet form one pancreas. Graph, mean±SEM percent change of insulin-containing cells as determined manually from images of 2 islets per pancreas (n=6 per treatment group). $*P<0.05$. (G) Cellular content of islets. Freshly isolated islets (100 islets in triplicate) and residual non-islet pancreatic debris were dissociated into single cell suspensions and stained for FACS analysis with anti-CD45-APC or isotype control antibody. Shaded area, islets. Open area, debris. (H) MHC class II expression. Islets from C57BL/6 mice were cultured (100 islets/well in duplicate) in the presence of AAT (0.5 mg/ml) 1 hour before the addition of IFNγ (5 ng/ml) plus IL-1β (10 ng/ml). 24 hours later, islets were dissociated into single cell suspensions and double-stained for FACS analysis with anti-CD45-APC and anti-MHCII-PE, or isotype control antibodies. Left, Mean±SEM percent change from control (CT) unstimulated islets. $*P<0.05$ between AAT-treated and untreated islets. Right, Representative FACS analysis; Shaded area, AAT-treated islets. Open area, stimulated islets. Events are gated for CD45+.

AAT Modifies Islet Response to Proinflammatory Mediators

Figure 4A:
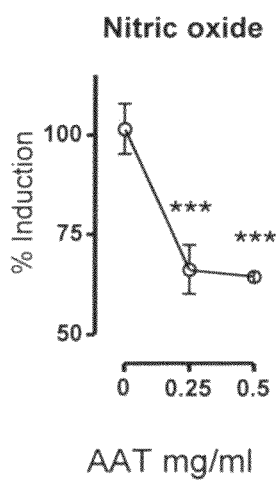
FIGS. 4A-4H illustrates an exemplary method of the effect of AAT on islet responses. (A-D) Mean±SEM of A. nitric levels, B. Cell viability and C. MIP-1α levels. Dashed line represents islets incubated at one-30th the concentration of IFNγ/IL-1β. D. TNFα levels. (E) Insulin induction assay. (F) Streptozotocin toxicity. Each image depicts a representative islet from one pancreas. (G) Cellular content of islets. (H) MHC class II expression.
Figure 4B:
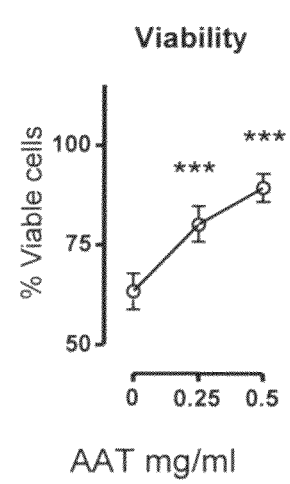
Figure 4C:
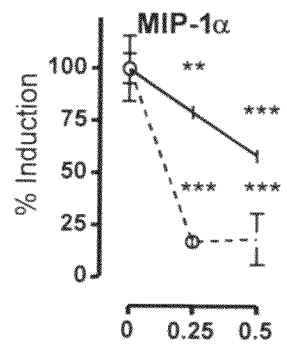
Figure 4D:
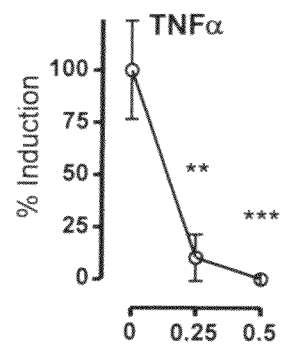
Figure 4E:
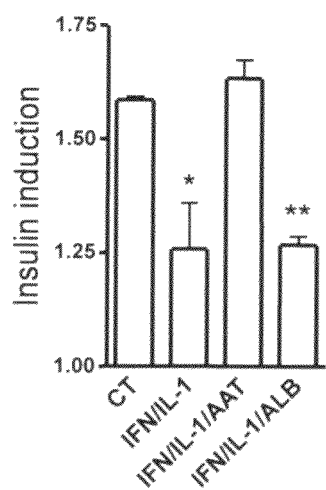
Figure 4F:
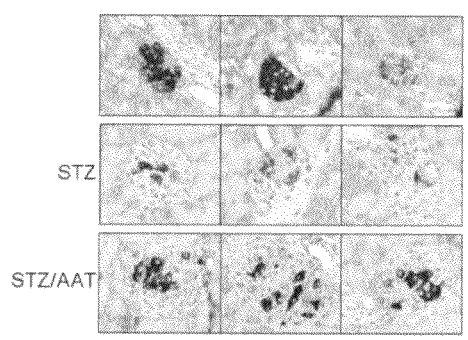
Figure 4G:
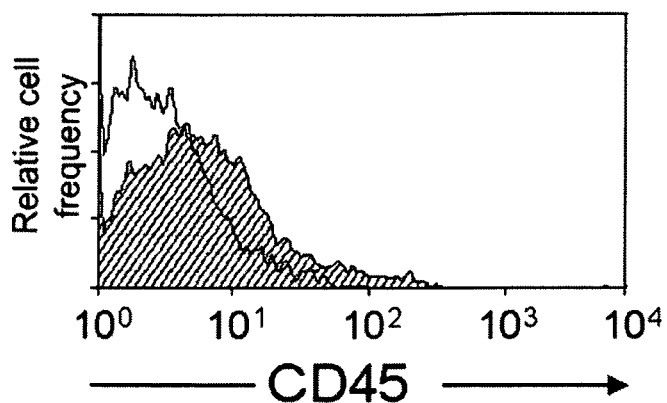
Figure 4H:
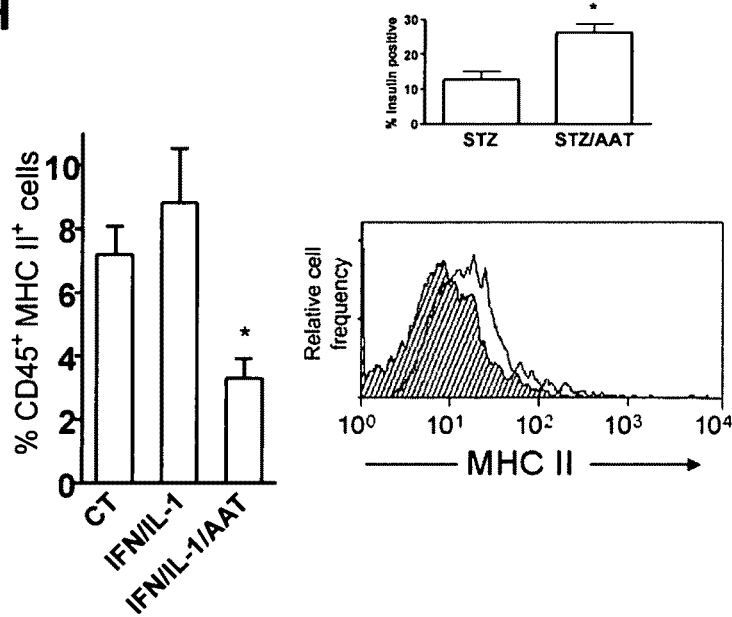

Various islet responses to IL-1β/IFNγ were examined in vitro. Islets exposed to IL-IL-1β/IFNγ for 72 hours produce nitric oxide (NO) in a concentration-dependent manner and exhibit NO-dependent loss of viability. As shown in FIGS. 4A and B, in the presence of AAT, less NO was produced and greater islet viability was obtained. The production of MIP-1α was decreased in the presence of AAT, particularly when stimulated by low concentrations of IL-1β/IFNγ (FIG. 4C). Notably, TNFα level in supernatants was markedly diminished by AAT (FIG. 4D). Insulin induction was inhibited by IL-1β/IFNγ, but was intact in the presence of IL-1β/IFNγ plus AAT (FIG. 4E). To test the effect of AAT on islets in vivo, STZ toxicity was evaluated. AAT (2 mg) was administered one day before, on the same day and a day after STZ injection. Immunohistochemistry of pancreata with anti-insulin antibodies at 48 hours after STZ injection reveals more insulin-producing cells in islets of AAT- than ALB-treated mice (26.3%±2.6 and 12.8%±2.3 insulin-producing cells per islet, respectively, FIG. 4/). White cell content of freshly isolated islets was evaluated by FACS analysis. Islets contain CD45+ cells (FIG. 4G) that are also positive for the monocytic/granulocytic markers GR1 and F4/80 (data not shown). This cell population responded to AAT with decreased surface MHC class II (FIG. 4H).

Example 5

FIG. 5A-5D illustrates the effect of AAT on TNF-α. (A) Islets from C57BL/6 mice were cultured (100 islets/well in triplicate) in the presence of AAT (0.5 mg/ml) or TACE inhibitor (10 mM) 1 hour before stimulation by IFNγ (5 ng/ml) plus IL-1β (10 ng/ml). Left, mean±SEM change in TNFα in supernatants after 72 hours of incubation. Right, mean±SEM fold change in membrane TNFα on islet cells after 5 hours of incubation, according to FACS analysis. ***P<0.001 compared control (CT) levels in the absence of AAT. (B) Representative FACS analysis of membrane TNFα on stimulated islet cells in the absence (open area) or presence (shaded area) of AAT. Events are gated for CD45+. (C) Streptozotocin-induced hyperglycemia. C57BL/6 mice were injected i.p. with saline (n=3), AAT (5 mg, n=3) or TNFα (1 mg/kg, n=3) or administered p.o. with TACE inhibitor (TACEi, 60 mg/kg, n=6) one day before injection of STZ (225 mg/kg, i.p.). Subsequently, AAT and TNFα were injected daily; TACE inhibitor was administered twice a day. At 48 hours, mean±SEM glucose levels are compared to those of normal littermates (n=3). *P<0.05, **P<0.01 compared to saline-treated, STZ-injected mice.

AAT Inhibits Release of Membrane TNFα

Figure 5A:
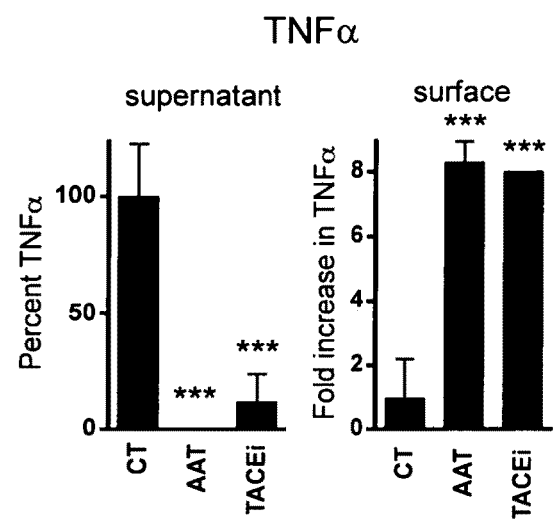
FIGS. 5A-5D illustrates the effect of AAT on TNFα. (A) Islets from C57BL/6 mice were cultured (100 islets/well in triplicate) in the presence of AAT (0.5 mg/ml) or TACE inhibitor (10 mM) 1 hour before stimulation by IFNγ (5 ng/ml) plus IL-1β (10 ng/ml). Left, mean±SEM change in TNFα in supernatants after 72 hours of incubation. Right, mean±SEM fold change in membrane TNFα on islet cells after 5 hours of incubation, according to FACS analysis. (B) Representative FACS analysis of membrane TNFα on stimulated islet cells in the absence (open area) or presence (shaded area) of AAT. (C) Streptozotocin-induced hyperglycemia.
Figure 5B:
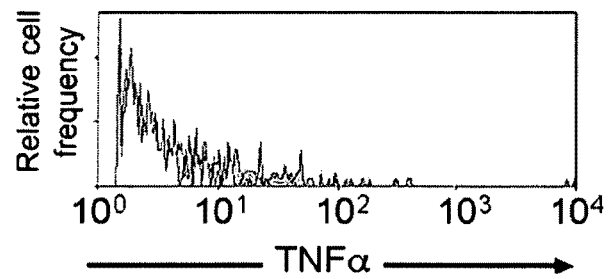

Proteolytic cleavage of membrane TNFα releases soluble TNFα from activated cells by the action of TNFα-converting-enzyme (TACE). The inventors examined the levels of membrane TNFα on stimulated islets in the presence of AAT. The effect of AAT was compared to that of a TACE inhibitor. Both AAT and TACE inhibitor decreased TNFα levels in supernatants of islets exposed to IL-1β/IFNγ (FIG. 5A, left). Under these conditions, membrane TNFα accumulated on the cell surface of CD45+ islet cells (FIG. 5A, right).

Figure 5C:
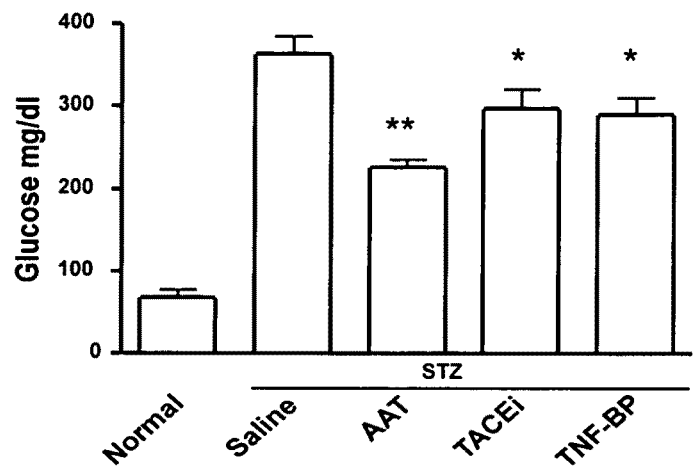

To assess the possibility that islet protection occurs via inhibition of release of membrane TNFα in vivo, TACE inhibitor, p75 TNF receptor (TNF BP) or AAT were introduced to mice prior to STZ injection. Although all mice developed hyperglycemia after day 4, the progression of β-cell toxicity was significantly affected by treatments. As shown in FIG. 5C, the effect of STZ at 48 hours was decreased in the presence of AAT (a decrease of 23.2%+2.3 in fasting glucose levels compared to STZ/saline injected mice). The effect of TACE inhibitor and p75 TNF receptor was not as profound. Similarly, TACE inhibitor prolonged islet graft survival to a lesser extent than AAT (preliminary data not shown).

Figure 5D:
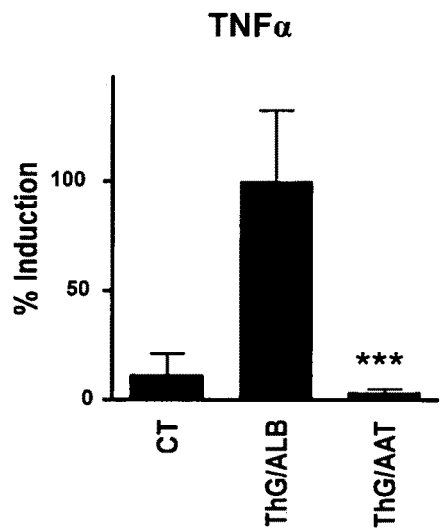
Figure 6D:
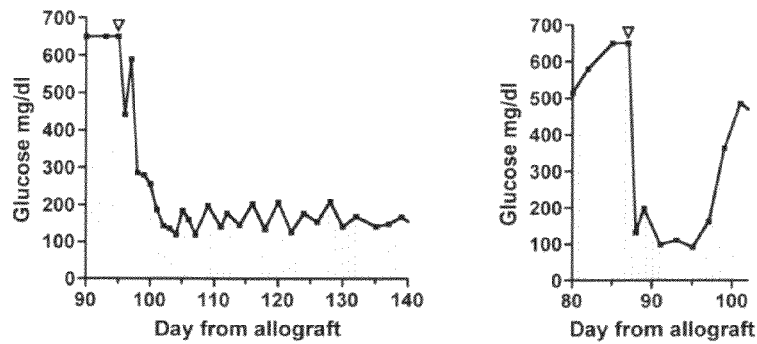
Figure 7A:
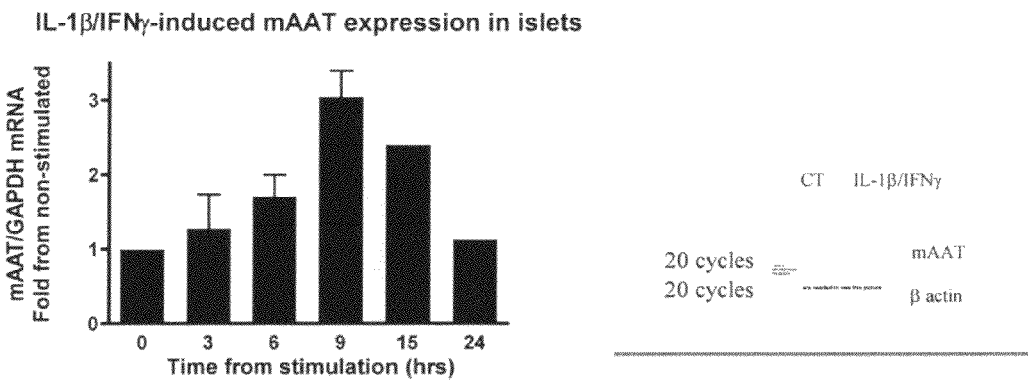
FIGS. 7A-7E illustrates the production of AAT by islet cell and reflection of islet graft survival. 7A illustrates a time course expression of mouse AAT mRNA after cytokine production (IL-1β and IFNγ) (left) and at 8 hours (right). 7B illustrates an example of islet injury during pancreatitis; the histology of normal islets (top left), the histology of islets of an inflamed pancreas (top right) and expression of mouse AAT in islets obtained from the pancreata in an acute pancreatitis model (bottom). 7C illustrates an example of samples of islet allografts taken post grafting and the percent change in AAT mRNA levels were assessed. 7D illustrates an example of islet protection from cytokine injury with endogenous AAT by introducing oncostatin M (an interleukin 6 (IL-6) family member) that induces AAT expression in islets, oncostatin M and AAT levels (top left); nitric oxide and viability levels assessed (top right) and nitric oxide production representing islet viability after 4 day exposure to oncostatin M and AAT production decreasing cytokine effects on the islets (bottom).
Figure 7B:
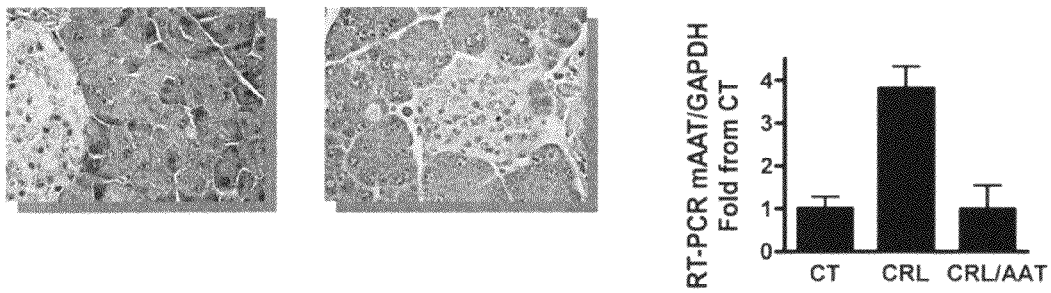
Figure 7C:
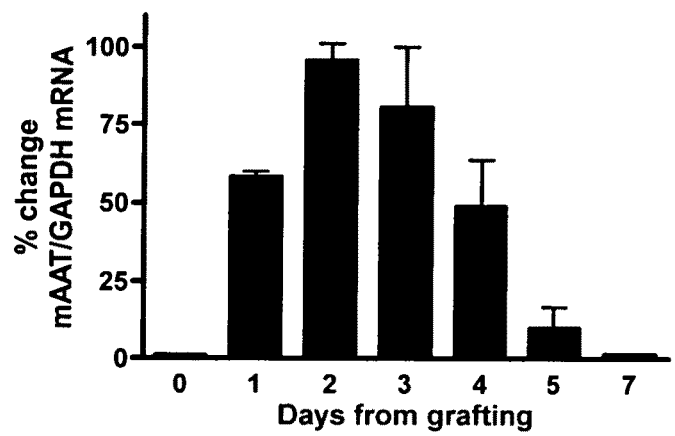
Figure 7D:
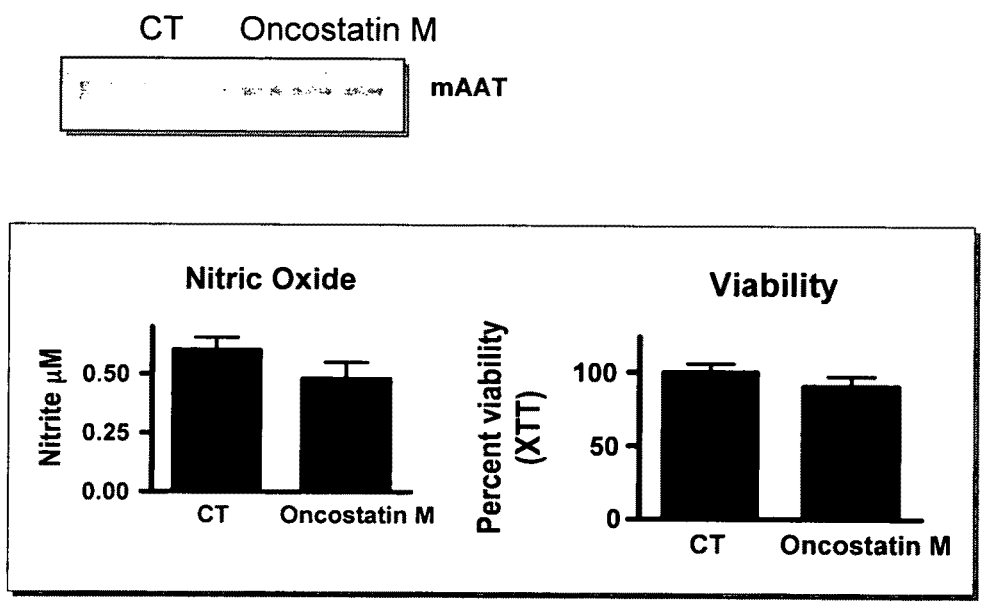
Figure 7E:
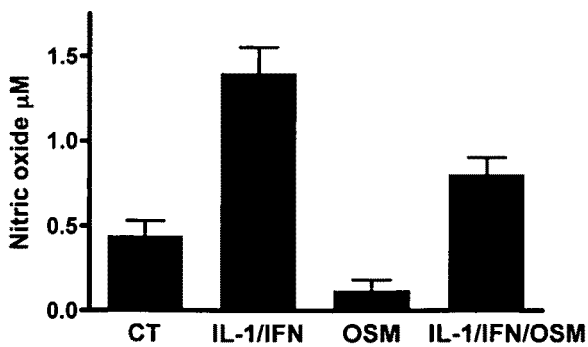
Figure 8A:
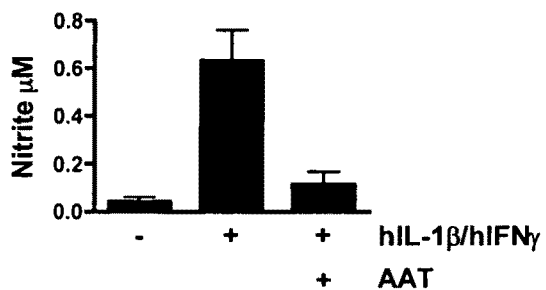
FIGS. 8A-8D illustrates the effect of AAT on human islets and the production of nitric oxide (8A), TNF-α production (8B) IL-6 (8C) and IL-8 (8D).
Figure 8B:
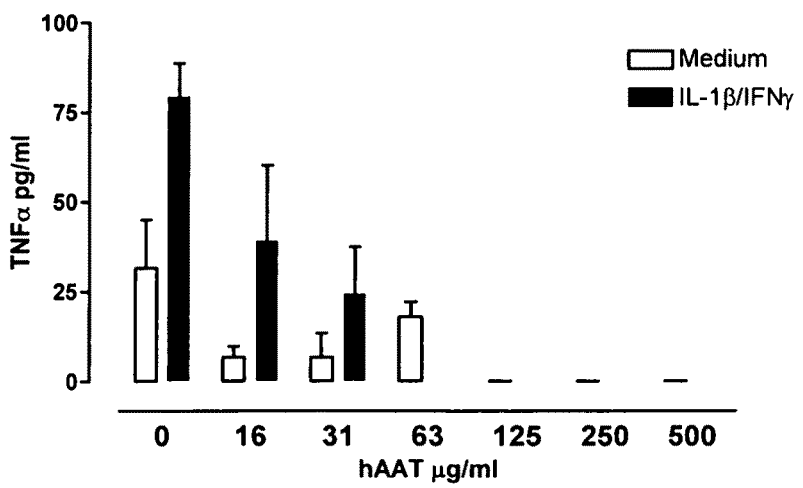
Figure 8C:
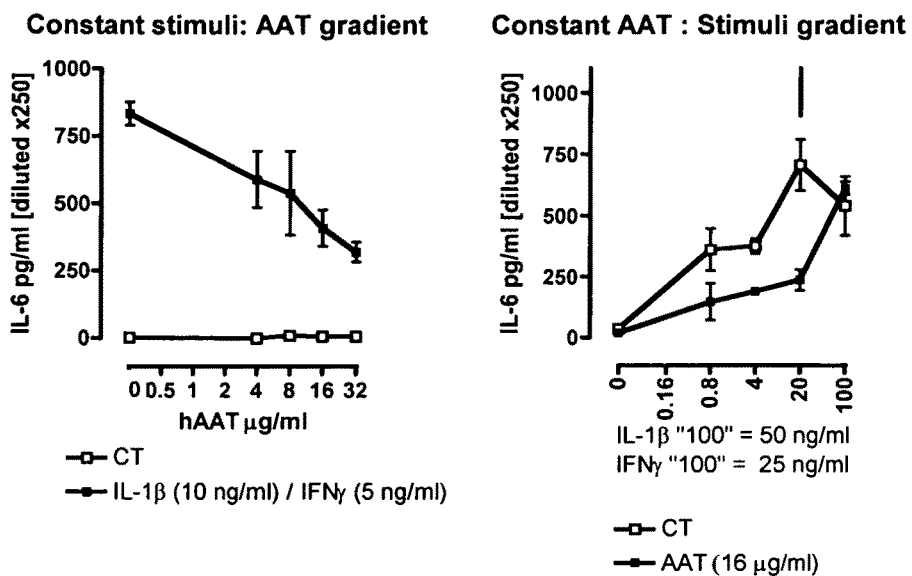
Figure 8D:
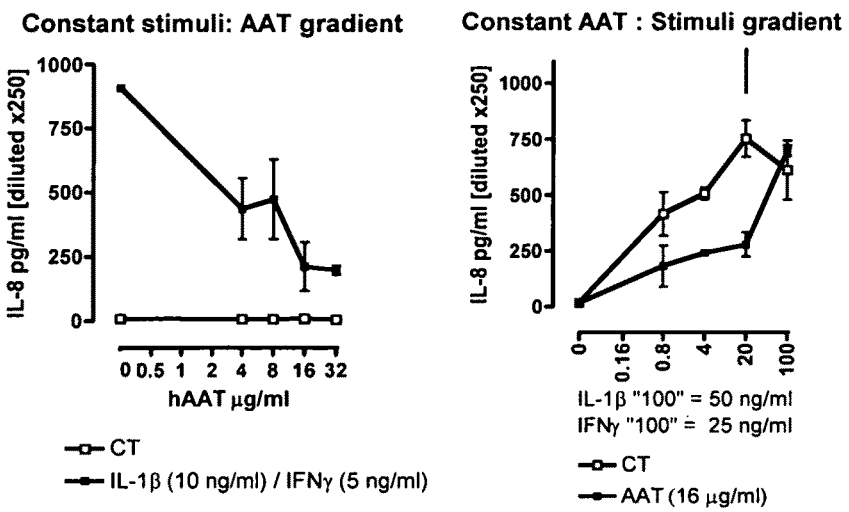

Splenocytes that were harvested 48 hours after ThG injection produced TNFα in culture (FIG. 5D). AAT administered prior to thioglycolate decreased TNFα release from cultured splenocytes. A similar trend was found with IFNγ (data not shown), signifying that the response to ThG had effects that extend beyond the peritoneal compartment and that pretreatment with AAT reduced these effects.

Example 6

FIG. 6A-6D illustrates the effect of AAT on Islet allograft transplantation. 6A illustrates the time course study after transplantation of islet cells. This example indicates that treated mice maintain normoglycemia over a 60 day period (n=4), after the AAT therapy was withdrawn. After withdraw of the therapy, the normoglycemia lasted another 20 days. 6A illustrates the glucose follow-up. Positive insulin staining in a day-85 treated islet graft was also demonstrated (data not shown). 6B illustrates an immune infiltrate found outside the graft area. 6C illustrates an increase in the presence of CD4+ and a comparative decrease in monocytes and neutrophils. It was also shown that massive vascularization was evident inside the graft (data not shown). It has been observed that long-lasting accepted islet grafts can be spared from an immune alloresponse even after therapy removal, whether the therapy had evoked an immune tolerance specific for the strain of donor islets was evaluated. For this, grafts were explanted by nephrectomy and the now-hyperglycemic original recipients were re-transplanted with either the same strain of islets as before (n=2), or a $3^{rd}$ strain which they had never encountered before (n=2). In accordance with established strain specific immune tolerance, mice accepted grafts from original donors, but had acutely rejected $3^{rd}$-strain grafts (6D); the same donor (left) and a $3^{rd}$ donor re-graft (right).

Example 7

FIG. 7A-7E illustrates the production of AAT by islet cell and reflection of islet graft survival. 7A illustrates a time course expression of mouse AAT mRNA after cytokine production (IL-1β and IFNγ) (left) and at 8 hours (right). To demonstrate the relevance of endogenous alpha-1-antitrypsin in physiological conditions, the issue of islet injury during pancreatitis was addressed. In mouse model of acute pancreatitis, isolated islets of pancreata that are inflamed express inducible alpha-1-antitrypsin. 7B illustrates an example of islet injury during pancreatitis; the histology of normal islets (top left), the histology of islets of an inflamed pancreas (top right) and expression of mouse AAT in islets obtained from the pancreata in an acute pancreatitis model (bottom). Alpha-1-antitrypsin levels during pancreatitis (caerulein model for acute pancreatitis). Top, histology of an islet in a normal pancreas (left) and an islet in an inflamed pancreas (right), representative of n=3. Bottom, expression of mouse alpha-1-antitrypsin in islets obtained from pancreata in acute pancreatitis model. Treatment of mice with exogenous alpha-1-antitrypsin resulted in down-regulation of endogenous alpha-1-antitrypsin expression, as well as decrease in serum TNFα levels (not shown).

To demonstrate the relevance of endogenous alpha-1-antitrypsin in islet transplantation, islet allografts from untreated transplanted mice on days 1 through 7 after transplantation (n=3) were excised. These were examined for alpha-1-antitrypsin expression and reveal a pattern which may fit inflammation phase (days 1-3) followed by loss of islet mass (days 4-7). 7C illustrates an example of samples of islet allografts taken post grafting and percent change in AAT mRNA levels were also assessed. Total RNA was extracted and mRNA for alpha-1-antitrypsin evaluated by RT-PCR.

Islet protection from cytokine injury was examined using endogenous alpha-1-antitrypsin by introducing oncostatin M, a member of IL-6 family that induces alpha-1-antitrypsin expression in islets without causing islet death. After 4 days that human islets were incubated with oncostatin M, for the purpose of accumulation of sufficient alpha-1-antitrypsin, islets were added the β-cell-toxic combination of IL-1β/IFNγ. Pretreated islets that had excess alpha-1-antitrypsin were protected from injury, supporting the concept that islet-derived alpha-1-antitrypsin may participate in islet protection during inflammation. 7D illustrates an example of islet protection from cytokine injury with endogenous AAT by introducing oncostatin M (an interleukin 6 (IL-6) family member) that induces AAT expression in islets, oncostatin M and AAT levels (top left); nitric oxide and viability levels assessed (top right). Bottom, human islets exposed to oncostatin M for 4 days produce enough alpha-1-antitrypsin to diminish the effects of IL-1β/IFNγ added for an additional 48 hours.

Example 8

In one exemplary study, alpha-1-antitrypsin on human islets was examined. FIG. 8A-8D illustrates the effect of AAT on human islets. The production of nitric oxide (8A), TNF-α production (8B) IL-6 (8C) and IL-8 (8D) was examined. 100 human islets per well were seeded in triplicates and added alpha-1-antitrypsin (AAT) 2 hours before stimuli. Supernatants were assayed 72 hours later. 3A, nitric oxide; 3B, TNFα; 3C, IL-6; 3D, IL-8. Results are mean±SEM and are representative of separate islet isolations from three human donors.

Methods

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Mice.

C57BL/6 and DBA/2 females were purchased from Jackson Laboratories.

Induction of Hyperglycemia by Streptozotocin, Islet Isolation and Islet Transplantation.

In one exemplary method, 5-6 weeks old C57BL/6 mice were treated intraperitoneally (i.p.) with 225 mg/kg Streptozotocin (STZ) (Sigma). Mice with established hyperglycemia were used at least 5 days after STZ administration. Islets were isolated from DBA/2 mice on day of transplantation, or 24 hours before in vitro assays, by enzymatic digestion of pancreata, by means known in the art, with minor modifications. Briefly, mice were anesthetized with i.p. ketamine (50 mg/kg, Vedco Inc.) and xylazine (10 mg/kg, Vedco Inc.). Each pancreas was inflated with 3.5 ml cold collagenase (1 mg/ml, type XI, Sigma), excised and immersed for 40 minutes at 37° C. in water bath. Pancreata were gently vortexed and filtered through 500-micron metal sieve. The pellet was washed twice in cold HBSS containing 0.5% BSA (Sigma) and reconstituted in RPMI-1640 (Cellgro, Mediatech) supplemented with 10% FCS (Cellgro), 50 IU/ml Penicillin (Cellgro) and 50 μg/ml streptomycin (Cellgro). Islets were collected on a 100-micron nylon cell strainer (BD Falcon), released into a petri dish by rinsing with HBSS (Cellgro, Mediatech) and 0.5% BSA (Sigma) and hand picked under a stereomicroscope. For transplantation, 450 islets were thoroughly washed from residual FCS in HBSS and 0.5% BSA and mounted on 0.2 ml tip for immediate transplantation. For in vitro assays islets were left to incubate for 24 hours at 37° C. Islet transplantation was performed into the left renal subcapsular space. Recipient mice were anesthetized, as described above. An abdominal wall incision was made over the left kidney. Islets were released into the subcapsular space through a puncture and the opening was sealed by means known in the art. Blood glucose follow-up was performed 3 times a week from end-tail blood drop using glucosticks (Roche). (Nanji, S. A. & Shapiro, A. M. Islet transplantation in patients with diabetes mellitus: choice of immunosuppression. BioDrugs 18, 315-28 (2004).)

Development of Anti-Human-AAT Antibodies in Mice.

In another exemplary method, in order to evoke specific antibody production against human AAT, mice were injected i.p. with 10 mg human AAT per 20-gram mouse for four times in intervals of 1 week. Mice were used in experiments 2 months after last administration. Antibody production was evaluated before transplantation experiments were carried out.

In one example, assaying for anti-human-AAT antibody levels was performed as described in the art. Briefly, mouse sera were kept at −70° C. until assayed for anti-human-AAT levels. Plates were coated with human AAT or albumin (2 μg/ml) in PBS at 4° C. overnight, then washed and blocked for 1 hour at 25° C. as described. Negative control serum was used in addition to test serum. Bound anti-AAT antibody using standard TMB substrate solution was measured (Sigma).

Cells. NIH-3T3 cell line (e.g. ATCC) were cultured. On day of peritoneal inoculation, $1 \times 10^7$ cells were freshly collected by trypsinization and washed with cold PBS. Pellet was resuspended in 1 ml cold PBS for immediate injection.

Infiltration Experiments.

Peritoneal infiltration was elicited by i.p. injection of 1 ml autoclaved thioglycolate (3% w/v, Sigma) or allogeneic cells (NIH-3T3), together with 0.1 ml saline, human albumin, human AAT or oxidized AAT. Peritoneal lavage was performed at 24 and 48 hours (thioglycolate) or on days 1-5 (allogeneic cells). For lavage, mice were anesthetized by isoflurane inhalation and injected immediately with 5.5 ml cold PBS containing 5% FCS and 5 U/ml heparin into the peritoneal cavity. After massaging the abdomen, peritoneal fluid was recovered. Red blood cells were lysed (RBC lysing buffer, BD PharMingen) and cell counts were performed with a hemocytometer. Cells were then isolated. Cells (about $1 \times 10^6$/polypropylene vial) were incubated with FcγRIII/II receptor block antibodies (Table I) for 10 min. Cells were then divided into two groups and incubated with mAbs for leukocytes and either CD3/NK cells or neutrophil/monocytes/macrophages (Table I) for 30 min. Cells were washed and fixed. The number of cells expressing a particular marker was calculated by multiplying percentages obtained from flow-cytometry by the concentration of cells in lavage fluid.

TABLE I

Rat Anti-Mouse mAbs Used for Flow Cytometry

| Purpose | mAb | (1) Specificity | (2) Source |
|---|---|---|---|
| Blocking | 2.4G2 | FcγRIII/II | BD PharMingen |
| Leukocytes | 30-F11 (APC) | CD45 (leukocytes) | BD PharMingen |
| Macrophages and | F4/80 (PE) | F4/80 (macrophages/monocytes) | eBiosciences |
| Neutrophils | RB6-8C5 (FITC) | GR1 (neutrophils/monocytes) | BD PharMingen |

TABLE I-continued

Rat Anti-Mouse mAbs Used for Flow Cytometry

| Purpose | mAb | (1) Specificity | (2) Source |
| --- | --- | --- | --- |
| CD3 | DX5 (PE) | Pan-NK cells | Miltenyi Biotec |
| NK cells | 17A2 (FITC) | CD3 | BD PharMingen |
| TNFα | MP6-XT22 (PE) | Mouse TNFα | eBiosciences |
| MHC class II | M5/114.15.2 (PE) | I-A$^{b/d}$, I-E$^d$ | BD PharMingen |
| Isotype control | Rat IgG1 (PE) | | eBiosciences |

An insulin assay and immunohistochemistry were performed by means known in the art (Nanji, S. A. & Shapiro, A. M. Islet transplantation in patients with diabetes mellitus: choice of immunosuppression. BioDrugs 18, 315-28 (2004)).

AAT Oxidation by Myeloperoxidase (MPO) System.

In one example, AAT (4 mg/ml) was incubated at 37° C. for 45 minutes with MPO (1 U/ml, Sigma), $H_2O_2$ (80 µM, Sigma) and NaCl (2.5 mM) in PBS, pH 7.4, by means known in the art. Reaction was terminated by boiling for 1 hour followed by filter-centrifugation of the system products. In this example, boiling was needed for the inactivation of MPO but this did not inactivate AAT (data not shown). Loss of activity of oxidized AAT was confirmed by elastase activity assay.

Elastase Activity Assay.

In another exemplary method, inhibition of a the serine protease elastase was evaluated 30 minutes after co-incubation of AAT or oxidized AAT with porcine elastase (Sigma) in triplicate, by known methods. The ability of elastase to liberate 4-nitroaniline ($A_{410}$) from SucAla$_3$-PNA was determined by kinetic measurement of light absorbance at 410 nm. Activity in the absence of inhibitors was set as 100% at the linear range of the assay.

Cytokine Assays.

An electrochemiluminescence (ECL) assay as known in the art was used for the measurement of mouse TNFα and MIP-1α. Briefly, cytokine-specific goat anti-mouse affinity purified antibodies were labeled with ruthenium (e.g. BioVeris) according to manufacturer's instructions. Biotinylated polyclonal anti-mouse antibodies (e.g. R&D Systems) were used. The amount of TNFα and MIP-1α chemiluminescence was determined using an Origen Analyzer (BioVeris).

Membrane TNFα.

Membrane TNFα on islet cells was detected by modification of a method for the evaluation of membrane TNFα on human PBMC. Briefly, single-cell suspension of islets was incubated with anti-mTNFα-PE mAb (Table I). Cells were washed with FACS buffer and resuspended in 0.5 ml 2% EM-grade formaldehyde.

Nitric Oxide Assay.

Nitrite levels in supernatants were determined using Griess reagent (Promega), as previously described (Chan, E. D. & Riches, D. W. Am J Physiol Cell Physiol 280, C441-50 (2001).

Apoptosis Assay.

The protective effect of AAT on islets may address one of the major obstacles in islet transplantation today, namely the inadequacy of islet mass and post-isolation islet viability. Freshly isolated human islets activate stress signaling pathways and exhibit high rate of apoptosis due to the process of isolation, necessitating the use of more than one islet donor per diabetic patient (Nanji, (2004); Abdelli, S. et al. Intracellular stress signaling pathways activated during human islet preparation and following acute cytokine exposure. Diabetes 53, 2815-23 (2004)).

In this example, apoptosis that follows islet isolation is diminished when islets are cultured with AAT (data not shown) and demonstrate that islets that are cultured with AAT for 24 hours prior to transplantation are able to normalize serum glucose levels of diabetic mice when transplanted autologously at an otherwise sub-functional mass (data not shown).

AAT Dosage.

Normal human plasma contains 0.8-2.4 mg/ml AAT, with a half life of 5-6 days[1]. In gene transfer studies in C57BL/6 mice, plasma levels of 0.8-1.0 mg/ml were achieved and provided protection from type I diabetes in NOD mice (Song, S. et al Gene Therapy 11, 181-6 (2004)). AAT administered intraperitoneally at 0.3-1.0 mg per mouse protected from TNFα-induced lethal response, and 0.8 mg AAT protected from D-galactosamine/LPS induced hepatic injury. Libert, C., et al., J Immunol 157, 5126-9 (1996).

Since AAT levels rise 3- to 4-fold during the acute phase response1, 2 mg per mouse results in plasma levels that do not exceed physiological levels.

Statistical Analysis.

Comparisons between groups were analyzed by two-sided t-test or ANOVA for experiments with more than two subgroups. Results are presented as mean±SEM.

Prolongation of Islet Graft Survival by AAT

In the present study, administration of clinical grade AAT to mice transplanted with allogeneic islets prolonged graft survival. In addition, AAT reduced migration of neutrophils and the subsequent infiltration of lymphocytes and NK cells in models of peritonitis. AAT also decreased secretion of TNFα and MIP-1α from islets and inhibited surface MHC class II expression on CD45+ islet cells in vitro. AAT was protective in a model of streptozotocin (STZ)-induced β-cell toxicity. Thus, it appears that AAT monotherapy targets several aspects of an activated inflammatory immune system, culminating in prolongation of islet allograft survival.

Effect of AA T on Cell Infiltration.

AAT diminished neutrophil migration into the peritoneum of mice injected with either thioglycolate or MHC-incompatible fibroblast cells. Other studies demonstrate that AAT inhibits neutrophil infiltration into kidneys during ischemia/reperfusion injury and into lungs following intratracheal administration of silica. In the present study AAT decreased islet production of MIP-1α and TNFα, resulting in islets deficient in chemotactic capabilities and therefore less immunogenic. The detrimental effect of neutrophils recruited to islets has been clearly demonstrated.

The involvement of macrophages in islet destruction is critical; their presence precedes insulitis in NOD mice and in prediabetic BB rat, and their depletion is protective during islet transplantation in rats. Islets are potent recruiters of macrophages; of the 51 gene products identified in freshly isolated human islets by cDNA array, expression of MCP-1 was found to be high. In mice, blockade of MCP-1 prolongs islet allograft survival when combined with a short subtherapeutic course of rapamycin. Islet allograft rejection is associated with a steady increase in intragraft expression of MCP-2, MCP-5, CCL5, CXCL-10 and CXCL9, and the chemokine receptors CCR2, CCR5, CCR1 and CXCR337. Accordingly, CCR2−/− mice and CXCR3−/− mice exhibit prolongation of islet allograft survival. In transplant settings, cytokines that are produced locally, as TNFα and IL-1β, cause damage to proximal cells independent of antigen recognition, and complement activation is critical for graft survival independent of allospecific immunity. The relevance of macrophages during early events in islet graft rejection is strengthened by the identification of CD45, F4/80 and Gr1 positive cells that express MHC class II in freshly isolated islets. In the presence of AAT, MHC class II levels were decreased below those of IL-1β/IFNγ-stimulated and unstimulated islets, supporting the idea that the process of islet isolation is sufficient to provoke activation of inflammatory pathways in islet cells. In light of the involvement of neutrophils and macrophages in graft rejection, interference with their functions by AAT provides an unusually non-inflammatory environment for the survival and recovery of engrafted islets.

As shown in the present study and elsewhere intraperitoneal injection of allogeneic NIH-3T3 cells evokes infiltration of macrophage and neutrophil on days 1-2 and of CD3+ and NK cells on days 4-5. The intensity of the latter infiltration was decreased by administration of AAT prior to allogeneic cell-line injection, but not by administration of AAT on day 3 (data not shown). In transplant settings, early non-specific factors contribute to subsequent specific immune response. It is therefore possible that the decrease in CD3+ and NK cell infiltration in the present study is secondary to the functional failure of the early innate response. However, regardless of AAT treatment, histological examination of islet grafts demonstrated that the infiltrate evoked by allogeneic islets consists of neutrophils and lymphocytes. Nevertheless, day 7 infiltrate was diminished in AAT-treated recipients, and, according to day 15 insulin immunohistochemistry, the infiltrate caused less islet destruction.

AAT Inhibits Release of TNFα.

Supernatants of IL-1β/IFNγ-stimulated islets contained strikingly less TNFα when incubated with AAT (induction of 100.0%±22.0 mean±SEM at 0 mg/ml AAT; 10.2%±11.2 at 0.5 mg/ml and 0.8%±0.1 at 1.0 mg/ml). In stimulated human PBMC, AAT was shown to diminish TNFα release without affecting TNFα-mRNA levels. In mice, accordingly, serum TNFα levels are decreased in LPS-injected AAT-treated mice. Importantly, treatment of mice with AAT blocks TNFα-mediated LPS-induced, but not TNFα-induced lethality in mice. In the present study, cultured mouse splenocytes isolated from thioglycolate-injected mice secreted less TNFα, 48 hours after injection of AAT.

In the presence of AAT, membrane TNFα accumulated in IL-1β/IFNγ-stimulated CD45+ islet cells. TNFα is released from the cell surface of macrophages by the action of TNFα converting enzyme (TACE), a metalloproteinase that cleaves membrane TNFα into the soluble form of TNFα. Inhibitors of TACE reduce TNFα release and increase the levels of membrane TNFα, as demonstrated by FACS analysis. Although the regulation of TACE activity is unclear, there is evidence to suggest that extracellular proteases are involved: TACE does not require its cytoplasmic domain for its activation, its activity does not depend on the amount of TACE on the cell surface, co-expression of TACE and transmembrane TNFα is not sufficient for processing of TNFα and the enzyme is expressed constitutively in various cells. Serpins, such as serpin PN-152, are suggested to possess extracellular regulatory effects on various surface proteins.

TACE is likely to be relevant for graft rejection since TACE inhibitor decreased injury parameters in a rat model of post-transplant lung injury. In addition to a decrease in TNFα levels, the study shows lower expression of MCP-1 and ICAM-1, and a reduction in neutrophil infiltration. Similar findings were obtained with both AAT and a broad spectrum metalloproteinase inhibitor in a model of silica induced neutrophil influx into lungs. However, TACE inhibitor only partially reproduced the protective effect of AAT on islet graft survival (preliminary data). Similarly, AAT protection from STZ-induced hyperglycemia was only partially reproduced by TACE inhibition and by recombinant p75-TNF-receptor. Despite the fact that locally secreted TNFα is detrimental to islet graft function, there is, to our knowledge, no report that describes protection of islet grafts by neutralization of TNFα activity. This distinction between AAT and TACE inhibition supports the possibility that AAT affects multiple aspects of the immune system, including not only TNFα release but also events that are downstream to TNFα activities.

In one embodiment, it is contemplated that a composition of the present invention may include AAT, an analog thereof, a serine protease, TACE inhibitor (TACEi) or any combination thereof. These compositions may be administered to a subject having or in need of a transplant and or in need of immunotolerance therapy.

Transplanted Islets are Stimulated by the Process of Isolation.

The process of islet isolation initiates in the islets an inflammatory cascade of cytokines and chemokines. Thus, isolated islets contain an intrinsic proinflammatory potential that may affect local host immune responses. The mechanism of cytokine-induced islet toxicity is believed to involve expression of inducible nitric oxide synthase and subsequent production of nitric oxide (NO) by non-β-cells. In the present study, AAT decreased NO production in IL-1βIFNγ-treated islets. Accordingly, islet viability was increased in a low NO environment, as attained by either incubation with a low concentration of stimulators (data not shown) or by introduction of AAT. Insulin induction, which is typically incomplete in the presence of cytokines, was intact in the presence of AAT and cytokines. In vivo, AAT protected islets in mice injected with STZ, as concluded by lower serum glucose levels. The portion of viable β-cells was visually assessed by insulin immunohistochemistry and was proportional to the decrease in serum glucose levels. The protection of AAT was limited to the initial days that follow STZ administration, suggesting that AAT interferes with NO production and immune activation and not with intracellular DNA alkylation. Freshly isolated non-stimulated CD45+ islet cells expressed MHC class II, which is involved in immune responses against islets. The levels of MHC class II were elevated in the presence of IL-1β/IFNγ and decreased in the presence of AAT. Interestingly, MHCII expression was unaffected by the presence of TACE (TNF alpha converting enzyme) inhibitor (data not shown), confirming that AAT activities extend beyond those of TACE inhibition.

According to the present study, the activities of AAT are directed against multiple components of the innate immune system, culminating in a protective effect on islet graft destruction. Islets in particular exhibited a high degree of protection from inflammatory processes in the presence of AAT. Pretreatment with AAT prior to islet transplantation may reduce both islet loss and the immunological response against the graft.

The terms and expressions that have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed herein, optional features, modification and variation of the concepts herein disclosed may be resorted to by those skilled in the art, and that such modifications and variations are considered to be within the scope of this invention as defined by the appended claims. In addition, where features or aspects of the invention are described in terms of Markush groups, those skilled in the art will recognize that the invention is also thereby described in terms of any individual member or subgroup of members of the Markush group and that other members of the described groups are included but may not be listed.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

Example 9

Prolonged Administration of hAAT to Diabetic Islet Allograft Recipient Mice Results in Strain-Specific Immune Tolerance In one exemplary method, to examine the outcome of islet allograft transplantation during extended monotherapy with hAAT, mice heterozygous for tissue-specific hAAT (hAAT-Tg) that exhibit levels of circulating hAAT that are below detection were used as graft recipients. hAAT-Tg mice (H-2b) were rendered diabetic, transplanted with allogeneic islets (H-2d) and treated with serial doses of hAAT (n=24) or albumin (n=6). As shown in FIG. 9A, control albumin-treated mice rejected allografts by day 12. In contrast, all hAAT-treated mice that were treated for the various durations indicated exhibited extended normoglycemia. The shortest 14-day course of hAAT therapy resulted in delayed loss of function in 50% of the transplants and in graft acceptance in the remainder. A 21-day course resulted in a single delayed graft failure event out of the six transplanted islet grafts. All twelve mice that received hAAT treatment for 30 days or more achieved graft acceptance (treatment duration 30 days n=8, 41 days n=1, 52 days n=2, 60 days n=1).

Figure 9B:
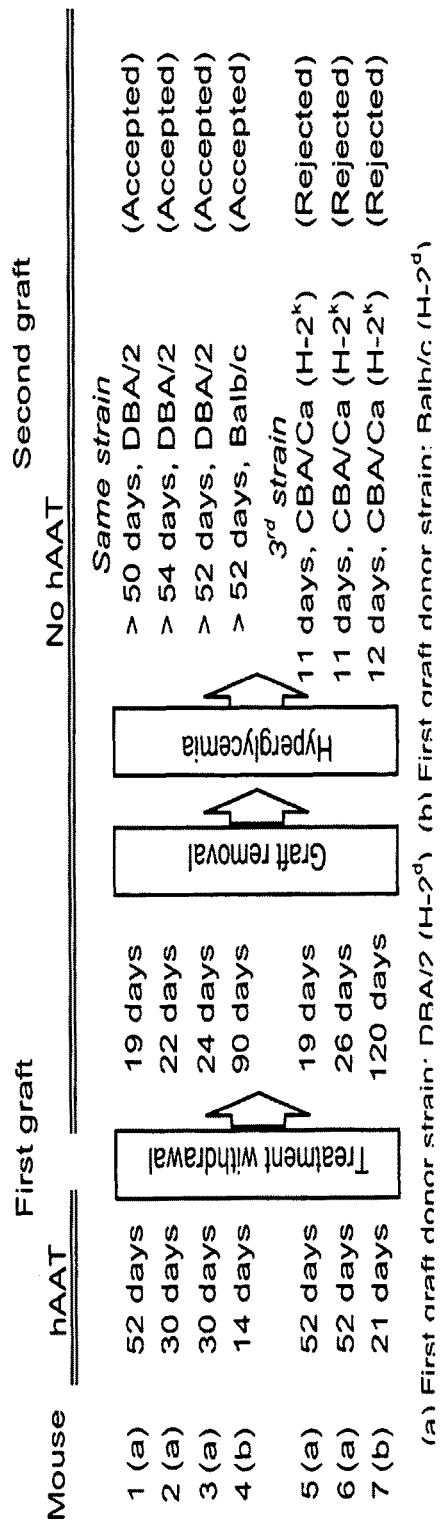
Figure 9C:
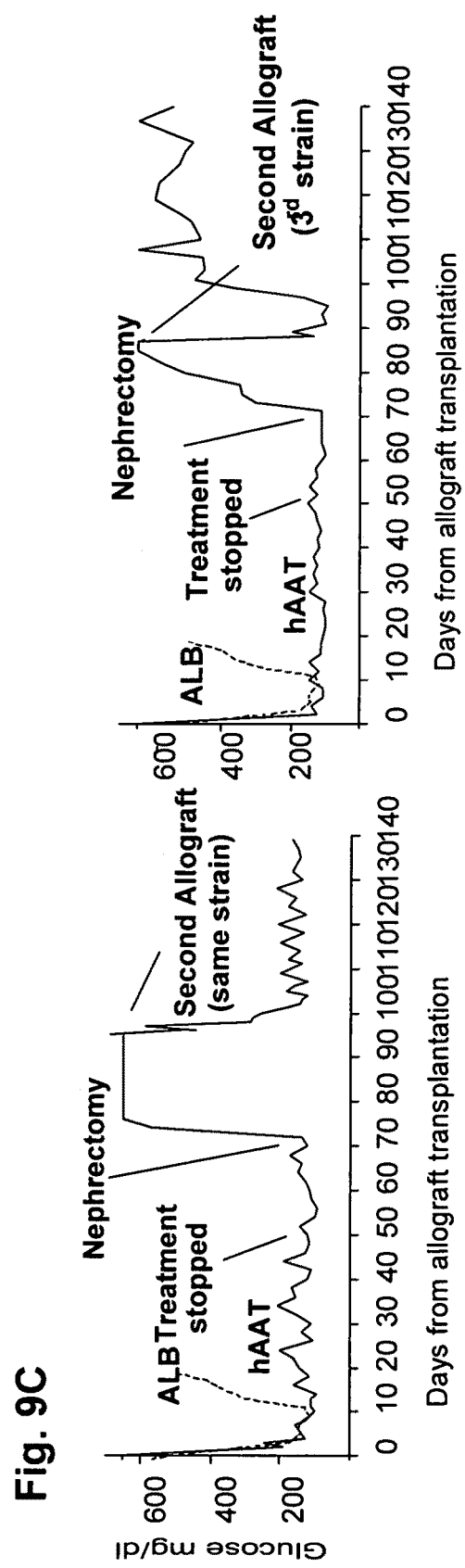

Removal of grafts by nephrectomy restored hyperglycemia. In another exemplary method, as illustrated in FIG. 9C left and right, by day 12 after transplantation the albumin-treated mouse (broken line) had mounted an acute allograft rejection response and developed overt hyperglycemia, whereas the hAAT-treated mice maintained normoglycemia for the duration of therapy. After withdrawal of hAAT, continued graft-derived insulin production was observed (FIG. 9B second column and FIG. 9C days 52-72), raising the possibility that allospecific immune tolerance was achieved. To examine this, grafts were removed and a second grafting procedure was undertaken in the subcapsular space of the remaining kidney without further treatment, using the same strain of islets that had been originally transplanted (n=4, H-2d, FIG. 9B and illustrated in an example in FIG. 9C left). In each case, following re-engraftment, recipient mice remained normoglycemic for over 50 days. To ascertain that antigen-specific immune tolerance had been induced, islets from a third strain (H-2k) were used as the source of the second graft in three hyperglycemic mice without further hAAT treatment (FIG. 9B and FIG. 9C right). As shown, all three mice exhibited acute rejection of third-strain allografts.

According to histology, a "cuff" of mononuclear cells surrounded the entire islet mass in all explanted grafts (FIG. 9D). The mononuclear cells were located at the intersection between the renal parenchyma and capsule, flanking an intact islet graft mass. By staining for several cell-specific markers we found the near absence of activated macrophages (CD11b, not shown), and a predominance of CD4 or CD8-positive cells, interspersed with CD25-positive cells (not shown).

Example 10

Inflammatory and Anti-Inflammatory Gene Expression in Islet Allografts

Figure 10:
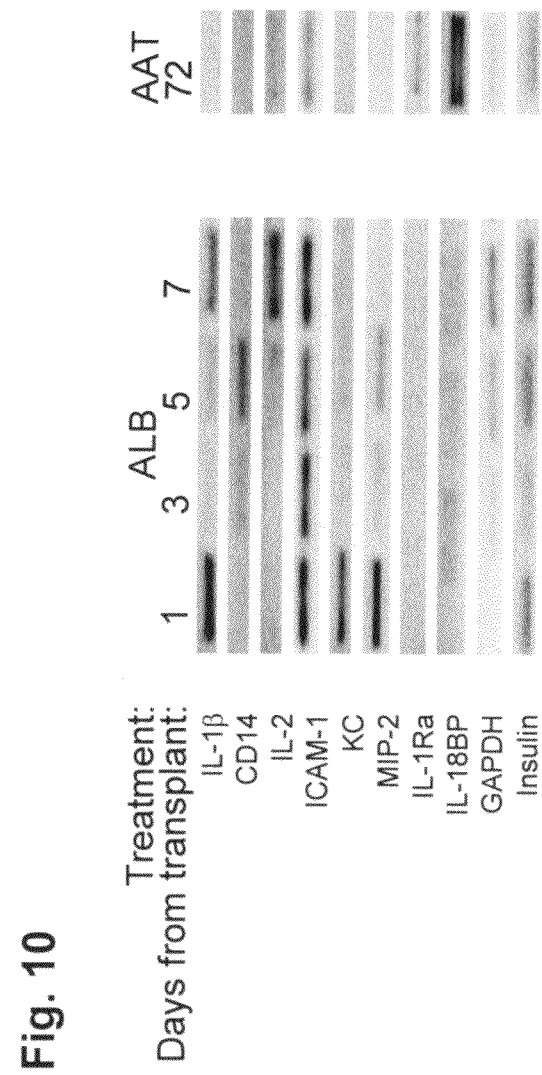
FIG. 10 represent exemplary effects of hAAT monotherapy on gene expression profile in islet allografts. RT-PCR of explanted islet allografts from albumin (ALB)-treated control and hAAT-treated mice. Left 4 columns, initial days after islet transplantation into control mice. Right column, day 72 after islet transplantation into hAAT-treated mice (see FIG. 9). Data are representative of n=6 (ALB) and n=3 (hAAT, time points between days 30 and 72 after transplantation).

In another example, in light of the sensitivity of islet beta cells to inflammatory mediators, expression of inflammation-related genes in explanted islet grafts was examined. FIG. 10 represents a comparison between steady-state mRNA patterns present early after transplantation in albumin-treated mice (days 1, 3, 5 and 7) and in long-lasting hAAT-treated islet grafts (representative day 72). As illustrated, transcripts of genes coding for islet-injurious ligands were low in grafts from hAAT-treated mice. These include the beta cell toxic IL-1β, in addition to CD14, a marker for invading macrophages, IL 2, carried by invading T cells and ICAM-1, which represents a pivotal adhesion molecule typically essential for cell migration. In addition, mRNA transcripts that encode for the pro-neutrophilic CXC chemokines, KC and macrophage inflammatory protein (MIP)-2, were undetectable in long-lasting islet allografts. Islet allograft explants from hAAT-treated mice also exhibited elevated expression of IL 1 receptor antagonist (IL 1Ra) and isoforms of IL-18 binding protein (IL 18BP), both reported to protect islet allografts. In contrast, explants of albumin-treated mice exhibited either low or undetectable expression of IL 1Ra and IL-18BP (FIG. 10, days 1, 3, 5 and 7). The intensity of the cellular infiltration can be appreciated by the progressive increase in GAPDH-mRNA levels in grafts from albumin-treated mice. The identification of insulin transcripts confirms the presence of beta cells in the explants.

Example 11

Some Cell-Specific Effects of AAT

Figure 11:
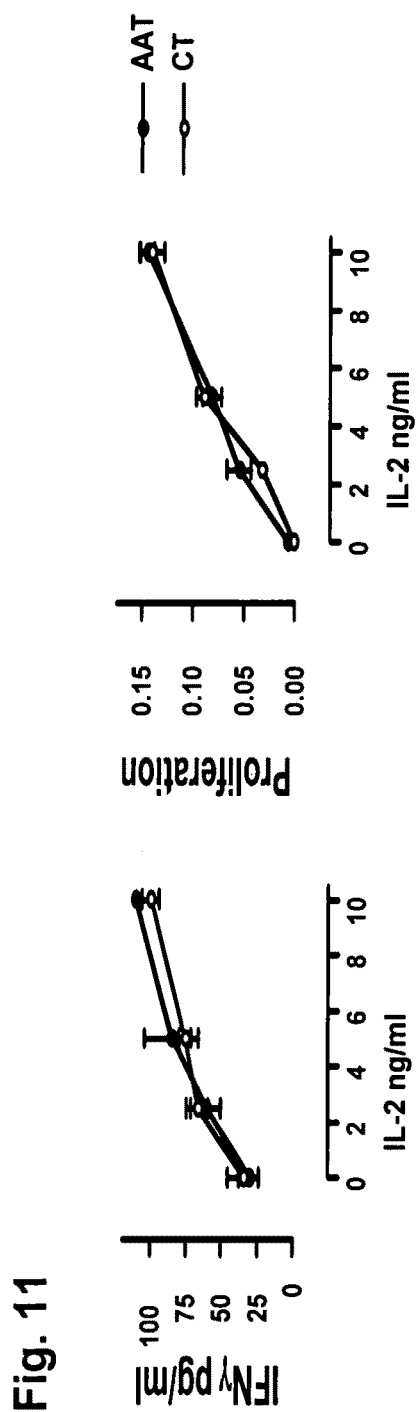
FIG. 11 represent exemplary cell-specific effects of hAAT. Inducible IFNγ levels (left) and cell proliferation (right) assessed in Con A-primed PBMC that were stimulated with increasing concentrations of IL-2 in the presence of 0.5 mg/ml hAAT or albumin (CT). Data are mean±SEM of three individual donors.
Figure 16A:
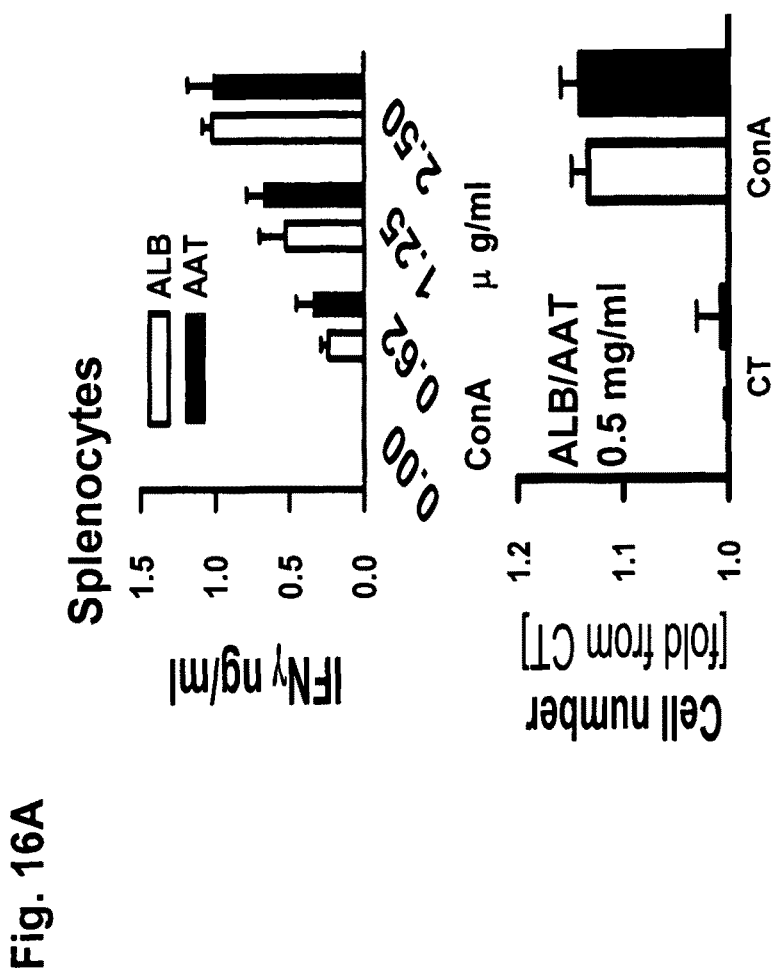
FIGS. 16A-16B represent exemplary experiments cell-specific effects of hAAT. (A) Mouse splenocytes. Inducible IFNγ levels (top), cell proliferation (bottom) and clump formation (right) in Con A-stimulated splenocytes in the presence indicated concentrations of hAAT or albumin (ALB). CT, cells with no added Con A. Photomicrographs depict an example of Con A-driven cell clumping. The data represent mean±SEM of three independent experiments. (B) Mouse peritoneal macrophages. Inducible nitric oxide production in peritoneal macrophages that were stimulated with IFNγ (5 ng/ml) in the presence of increasing concentrations of hAAT. The data are mean±SD. *p<0.05, **p<0.01.
Figure 16B:
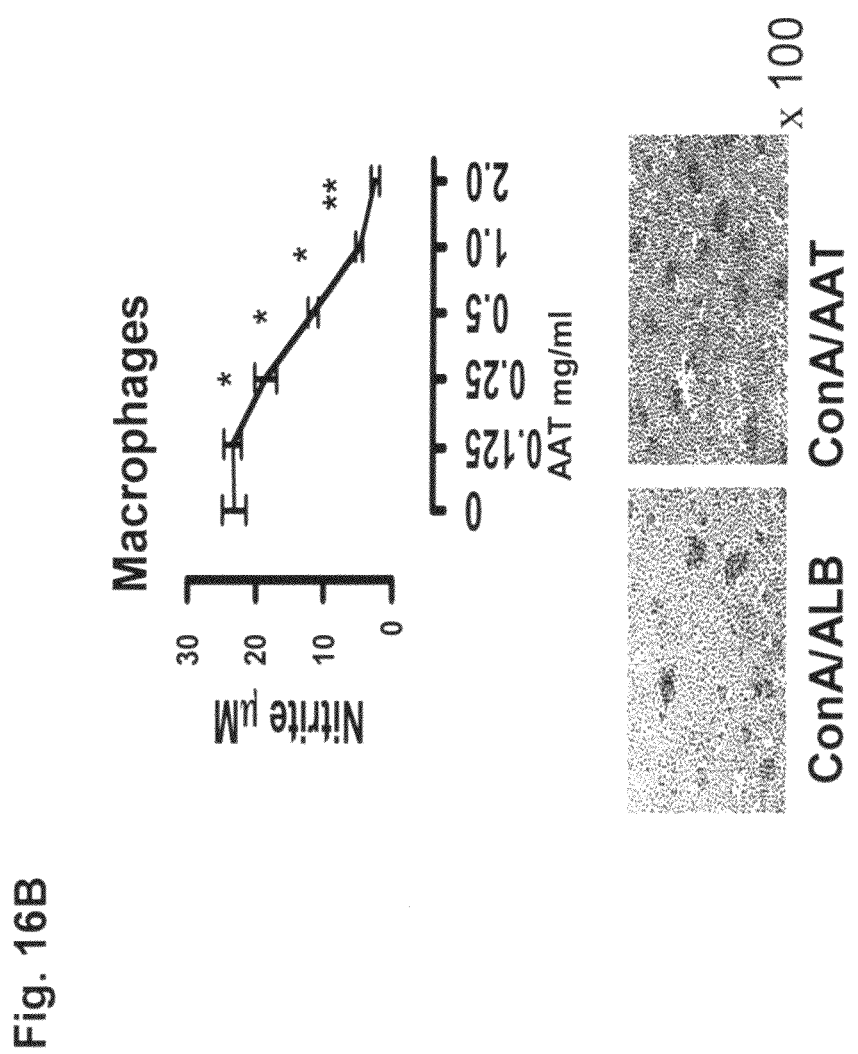

In another example, expression of anti-inflammatory molecules observed here belong to grafts that were explanted several weeks after withdrawal of hAAT treatment (see FIG. 9). It is therefore likely that the intragraft anti-inflammatory gene expression profile reflects the acquired cellular components that have progressively accumulated in the antigen-rich site. In order to examine the effects of hAAT on major cell subpopulations, in vitro assays were performed for lymphocytic and non-lymphocytic responses. As illustrated in FIG. 11, IL-2-stimulated human peripheral blood mononuclear cells (PBMC) were able to produce IFNγ and proliferate, as expected, in the presence of hAAT. Similarly, mouse splenocytes responded to Con A with secretion of IFNγ, as well as increased cell proliferation and cell clumping, each response unaffected by hAAT (FIG. 16A). In contrast to lymphocytic responses, peritoneal macrophages responded to hAAT by secreting significantly less IFNγ-induced nitric oxide in a concentration-dependent manner (FIG. 16B).

Example 12

Treg-Related Gene Expression in hAAT-Treated Islet Allografts

Figure 12A:
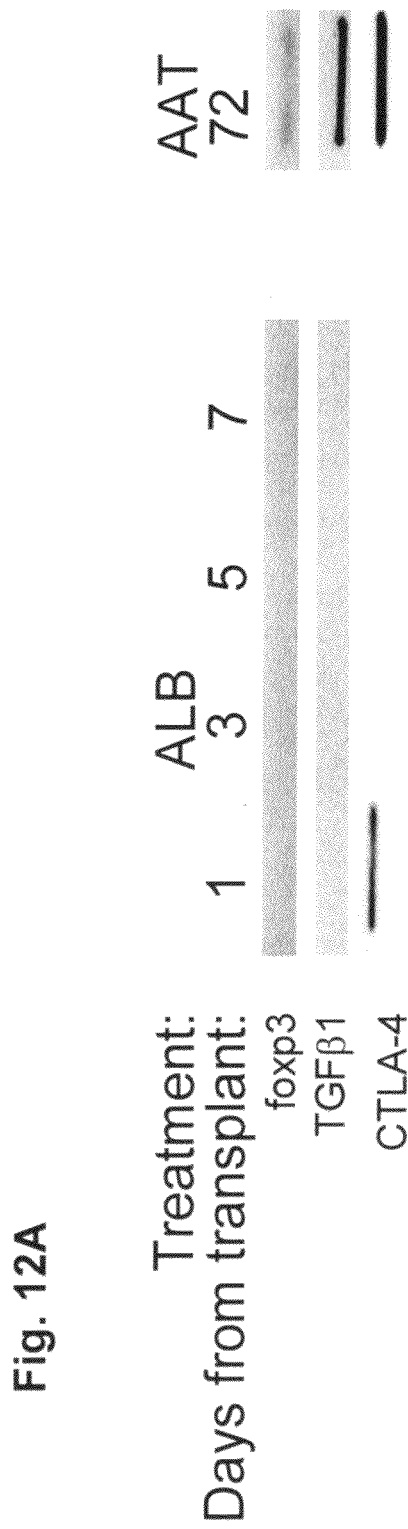
FIGS. 12A-12B Identification of hAAT-induced IL-10-expressing Treg cells in non-rejecting islet allografts. (A) RT-PCR of explanted islet allografts in albumin (ALB)-treated graft recipients during acute allorejection (Left-4 columns, days 1-7) and hAAT-treated graft recipient 20 days after withdrawal of hAAT treatment (Right column, day 72, see FIG. 12). Data are representative of n=6 (ALB) and n=3 (hAAT, representative time point between days 30 and 72 after transplantation). (B) Intragraft gene expression profile throughout hAAT therapy. RT-PCR of explanted islet allografts in hAAT-treated graft recipients during hAAT treatment. K, tissue from pole opposite to the grafting site. G; intragraft gene profile.
Figure 12B:
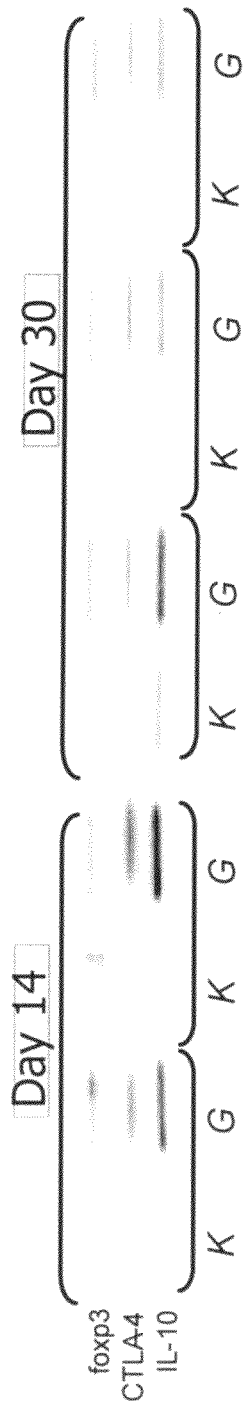

In the unique set of genes expressed within grafts of hAAT-treated recipient mice, we also observed the expression of genes indicative of Treg cells (FIG. 12). As shown, grafts from hAAT-treated mice (FIG. 12A representative day 72) exhibit a significantly elevated expression of foxp3, TGFβ and CTLA-4, representing the expected phenotype of Treg cells. In contrast, the expression of these genes was either below detection or terminated early in grafts from albumin-treated mice (days 1, 3, 5 and 7). As depicted in FIG. 4b, the presence of foxp3-positive cells was observed as early as day-14 of hAAT therapy in sections that contained the graft site (FIG. 4b, G). Notably, in renal tissue from kidney portions that did not contain the grafted islets (FIG. 12B, K), foxp3-positive cells were also observed. CTLA-4 expression was only present inside the graft (G). Of particular importance, IL-10 transcript levels were closely associated with foxp3-expression, suggesting that the identified Treg cells are also producers of IL-10.

Example 13

Figure 13B:
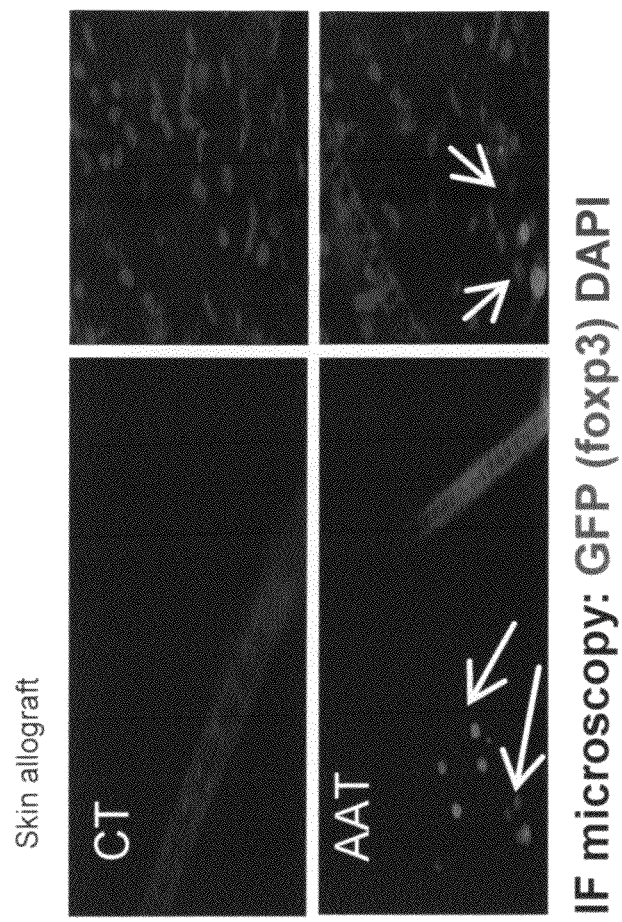
Figure 13C:
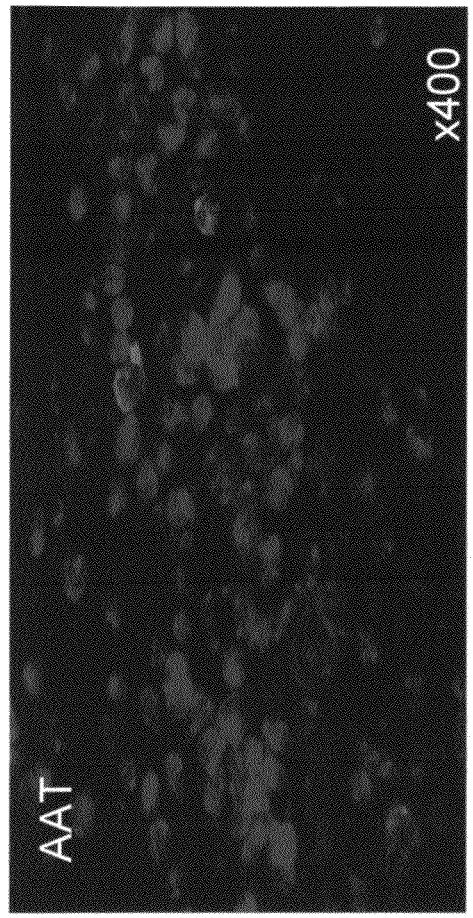

Time-Dependent Distribution of Treg Cells Between Draining Lymph Nodes (DLN) and Allograft In another example, in order to examine the effect of hAAT on Treg cell development during transplantation, foxp3-GFP knock-in mice were used as graft recipients (C57BL/6 background, H-2b). A vigorous allo-recognition response was evoked by implanting wild-type skin grafts (H-2d) under the surface of both left and right thighs. Animals were treated with hAAT (n=13) or albumin (n=13) using the same dosing schedule employed in the islet transplantation protocol (see FIG. 1). Inguinal DLN were removed on various days after grafting and CD4+-sorted cells were examined by FACS and by RT-PCR for foxp3-positive cells. As shown in FIG. 13A, between transplantation and 3 days after engraftment of islets the number of foxp3-positive cells in the DLN unvaryingly decreases in both the albumin-control and hAAT-treated graft recipient mice. However, between days 4 and 9 DLN from hAAT-treated mice had more foxp3-positive cells. In the days that followed, the gap in the size of the Treg population was restored. Gene expression analysis corroborated FACS findings (FIG. 13A inset). By using foxp3-GFP knock-in mice as matrigel-skin graft recipients, we were able to observe Treg cells infiltrating into allografts by day 10 after transplantation. This model offers a particular advantage as invading fluorescent cells can be directly identified in freshly-obtained, unstained specimens using fluorescent microscopy. As shown in FIG. 13B, invading foxp3-positive cells localized to grafts in hAAT-treated animals (bottom). In this technique, autofluorescent fur can be observed. Total intensity of infiltrating cells can be appreciated by DAPI counter-staining. Similarly, as shown in FIG. 13C, islet allografts that had been transplanted into foxp3-GFP knock-in recipient mice also contained foxp3-positive cells in the "cuff" site. The proportion of foxp3-positive cells approximated that found with CD4/CD25 co-staining (not shown). From these findings, it appears that hAAT treatment promotes early accumulation of Treg cells in the draining lymph nodes and a progressive migration into the alloantigen-rich site.

Example 14

Early Local and Systemic Effects of hAAT

Figure 14:
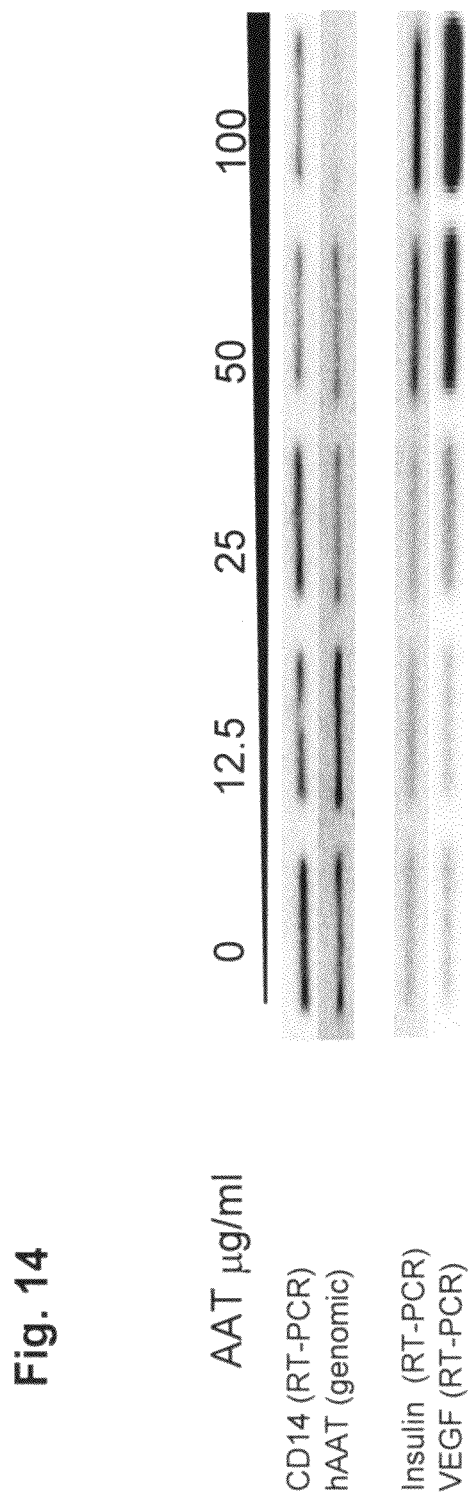
FIG. 14 represents an exemplary method illustrating of early local and systemic effects of hAAT. Wild-type islet-matrigel grafts containing increasing concentrations of hAAT (indicated, amount per matrigel) were explanted 48 hours after transplantation into hAAT-Tg recipients. Top, identification of CD14-positive cells (RT-PCR) and identification of host-cells inside the graft (genomic). Bottom, RT-PCR depiction of insulin and VEGF intragraft transcripts.

In another exemplary method, events that might precede the changes observed in the DLN were studies. Islets embedded into matrigel offer a model for examination of islet-driven cellular invasion during the first 48 hours of provocation. Allogeneic islets were introduced into hAAT-containing matrigel plugs (12.5-100 μg hAAT per graft) and implanted subcutaneously into mice. Grafts were retrieved 48 hours after transplantation and intragraft steady-state mRNA levels were assessed. As shown in FIG. 14, a dose-dependent decrease in CD14 mRNA levels had occurred, reflecting hAAT-dependent inhibition of macrophage invasion. Distinctively, the recipient mice carry the hAAT genomic insert and invading host cells can thus be identified. The amount of invading cells was decreased in the presence of hAAT, as corroborated by histological examination of the explanted matrigel at 48 hours (not shown). Copies of insulin mRNA transcripts correlated with the amount of added hAAT, representing improved hAAT-mediated beta cell viability. hAAT treatment also resulted in a dose-dependent increase in VEGF mRNA levels. VEGF mRNA in the matrigel-islet graft is likely to be of islet-cell origin since VEGF mRNA copies coincided with near absence of host genomic DNA (FIG. 14).

Figure 17:
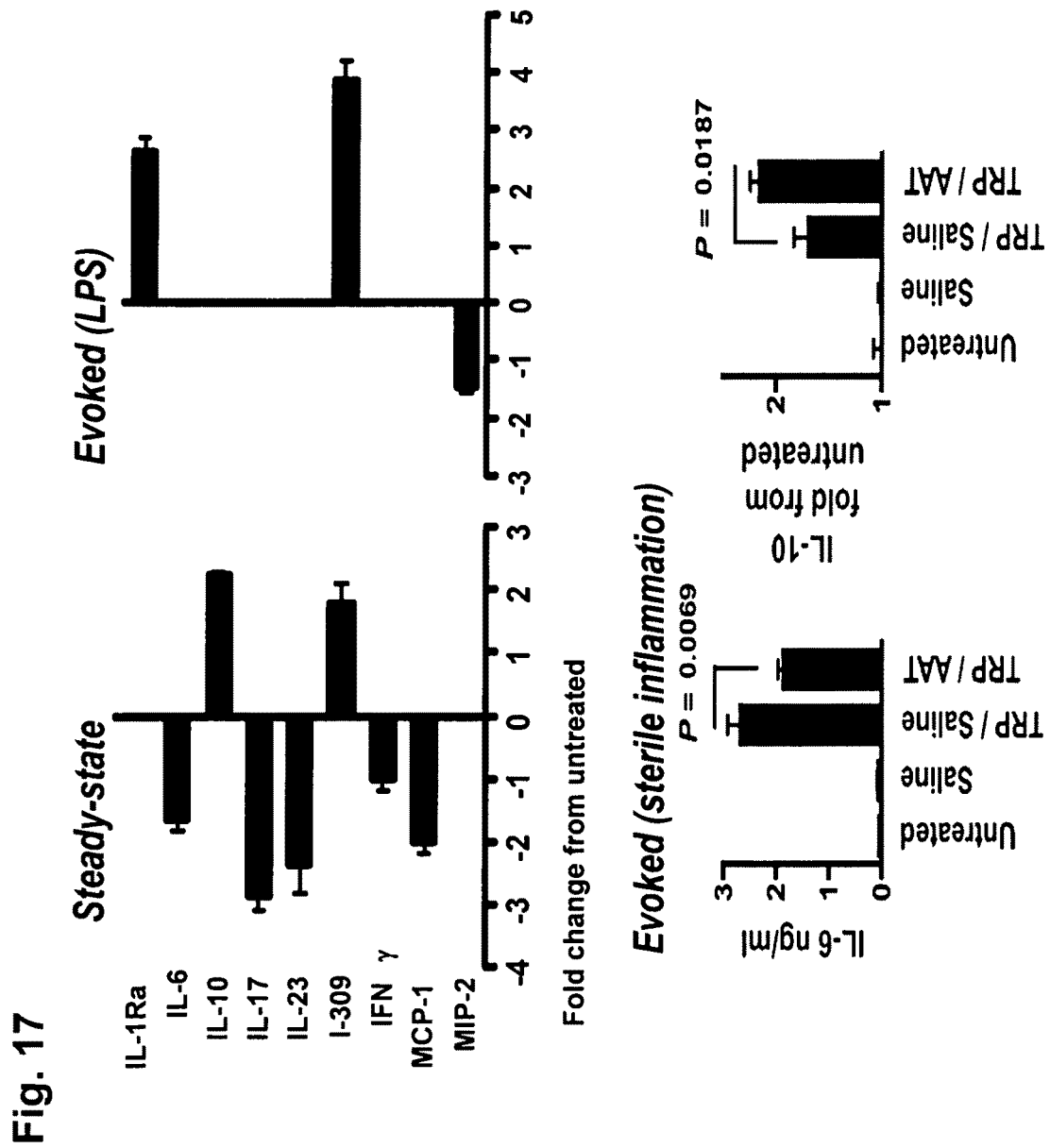
FIG. 17 represents exemplary effects of early local and systemic effects of hAAT. hAAT-induced changes in serum cytokines. Top-Left, Unprovoked serum cytokines after a 10-day schedule (see FIG. 9) of hAAT-treatment (n=3) compared to albumin treated mice (n=3). Relative cytokine levels were determined in duplicate by the Proteome Profiler (see Methods). Results are presented as mean±SEM fold-change (all $p<0.05$) in hAAT-treated mice over that observed in albumin-treated mice. Out of 36 cytokines tested, those without statistically significant changes are not shown. Top-Right, LPS-elicited cytokines. Following a 10-day schedule of hAAT (n=3) or albumin treatment (n=3), mice were injected with LPS (1 mg/kg) and after 2 hours serum was collected. Differences are shown as mean±SEM fold-change in hAAT-treated mice compared to albumin-treated mice. Bottom, sterile-inflammation-induced serum cytokines. Sera from hAAT-treated and saline-treated mice that were injected intramuscularly with either turpentine or saline 24 hours earlier. IL 10 and IL 6 levels were measured by specific ELISA. Mean±SEM from 3 experiments.

In another method, in addition to local events that reflect an inflammation-dampened antigen presentation environment, more comprehensive changes that may support the generation of Tregs were examined. Mice were subject to 10 days of hAAT treatment in order to reproduce the circulating cytokine environment of a treated islet graft recipient. Control mice received albumin. Serum levels of cytokines were then measured. As shown in FIG. 17, serum levels of Th17-related cytokines, IL-17 and IL-23, were 3-fold lower compared to levels in control mice. Serum IL-6 and MCP-1 were also decreased. On the other hand, serum IL-10 levels increased 2-fold and the levels of 1-309, a chemoattractant for Treg cells, increased 2-fold. To examine the circulating cytokines evoked during a vigorous inflammatory response, hAAT or albumin-treated mice (10 days) were challenged with LPS, and serum cytokines were assessed after 2 hours (FIG. 17). Once more, I-309 and MIP-2 levels exhibited the favorable changes observed in hAAT-treated non-challenged mice. Most strikingly, circulating IL-1Ra levels increased 3-fold. The effect of hAAT treatment on serum IL-6 and IL-10 levels were also studied during a sterile inflammatory response (FIG. 17). In this procedure the inflammatory response results in increased levels of IL 1β-dependent IL-6. However, mice treated with hAAT exhibited a 30% decrease in serum IL-6 protein levels and a 27% increase in serum IL-10 protein levels.

Effect of AAT on Dendritic Cell Migration, Maturation and Function

Figure 18A:
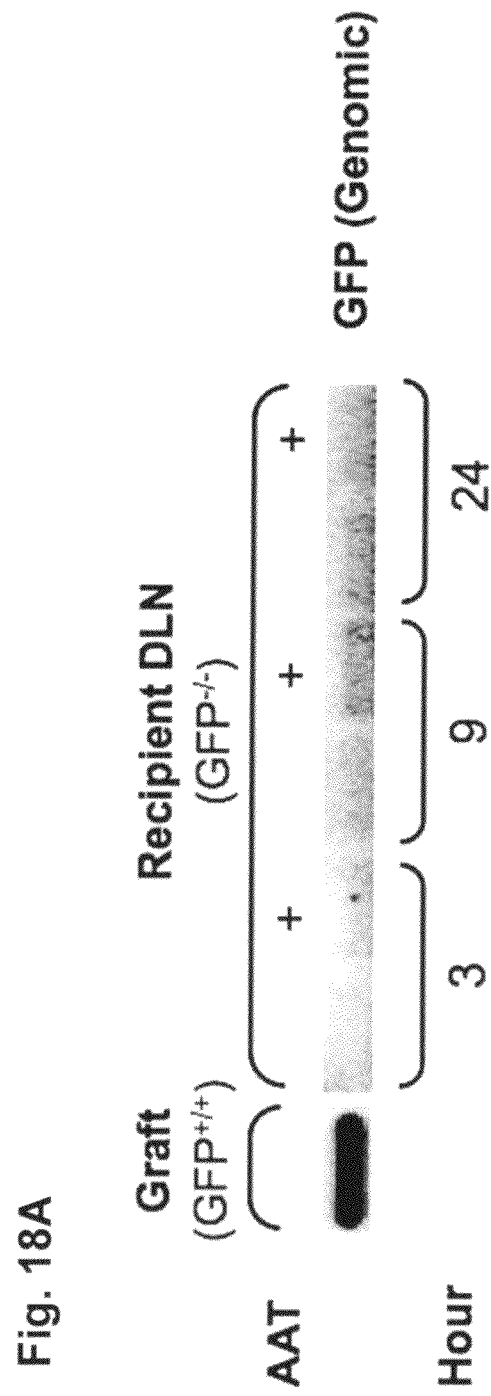
FIGS. 18A-18B represent exemplary experiment effect of AAT on dendritic cell migration and maturation. (A) Graft-derived cell migration into DLN. GFP-transgenic skin grafts were transplanted into wild-type recipient mice treated with a 10-day treatment schedule of hAAT or albumin (see FIG. 9). PCR amplification of genomic DNA extracted from the graft tissue is shown in the left lane and from the inguinal DLN in the remaining lanes. Representative data from one of three independent experiments is shown. (B) In vitro dendritic cell maturation. Bone-marrow-derived GM-CSF-differentiated dendritic cell were cultured with no stimulant (CT) or LPS (100 ng/ml) in the absence or presence of hAAT (0.5 mg/ml) for 24 hours. FACS analysis of CD11c-positive cells for surface levels of MHCII (top) and CD86 (bottom). Proportion of the double-positive population is depicted as percent from total cells. Representative panels from three experiments performed in 6-plicate.

To investigate the implications of a dampened antigen presentation process during transplantation, we studied dendritic cell activation in vitro and in vivo. Using transgenic GFP-positive donor skin grafts and subsequent PCR amplification of DNA isolated from DLN, we evaluate the migration of graft-derived cells towards DLN in-vivo (FIG. 18A). Mice received hAAT one day before grafting, as during islet allograft transplantation. Graft-derived DNA was present in DLN after transplantation in both control and hAAT-treated mice.

Example 15

Figure 15:
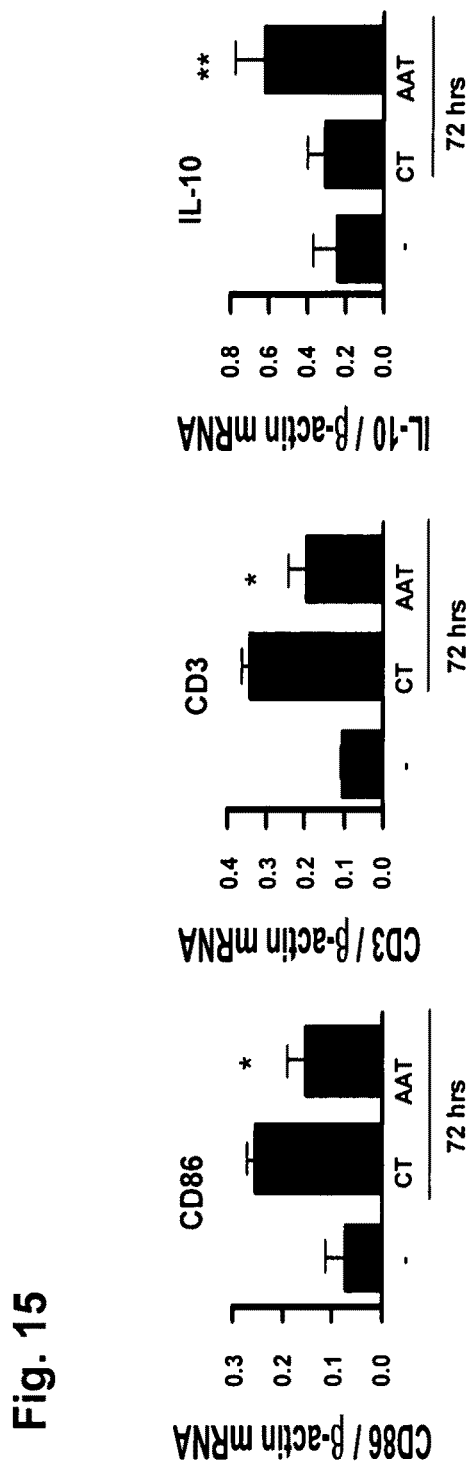
FIG. 15. represents an exemplary effect of AAT on dendritic cell migration and maturation. CD86, MHC class II and IL 10 expression in renal DLN. 72 hours after allogeneic skin grafting under the renal capsule DLN were harvested and examined by RT-PCR. DLN from non-grafted mice (first bar on left) is compared to 72-hour DLN gene expression from untreated (CT) and hAAT-treated (AAT) mice. Mean±SEM from three experiments. *p<0.05, **p<0.01 between CT and AAT.

Effects of hAAT on the transcript levels of CD86, CD3 and IL-10 in renal DLN of mice receiving skin grafts into the renal subcapsular space were examined (FIG. 15). For background gene expression, DLN from non-transplanted mice were examined. Seventy-two hours after transplantation, CD86 mRNA transcript levels were reduced by hAAT treatment 2-fold. At the same time point, DLN contained 2-fold less total CD3 mRNA transcripts. Notably, a 2.5-fold rise in IL-10 gene expression was observed in DLN from hAAT-treated grafted mice.

Figure 18B:
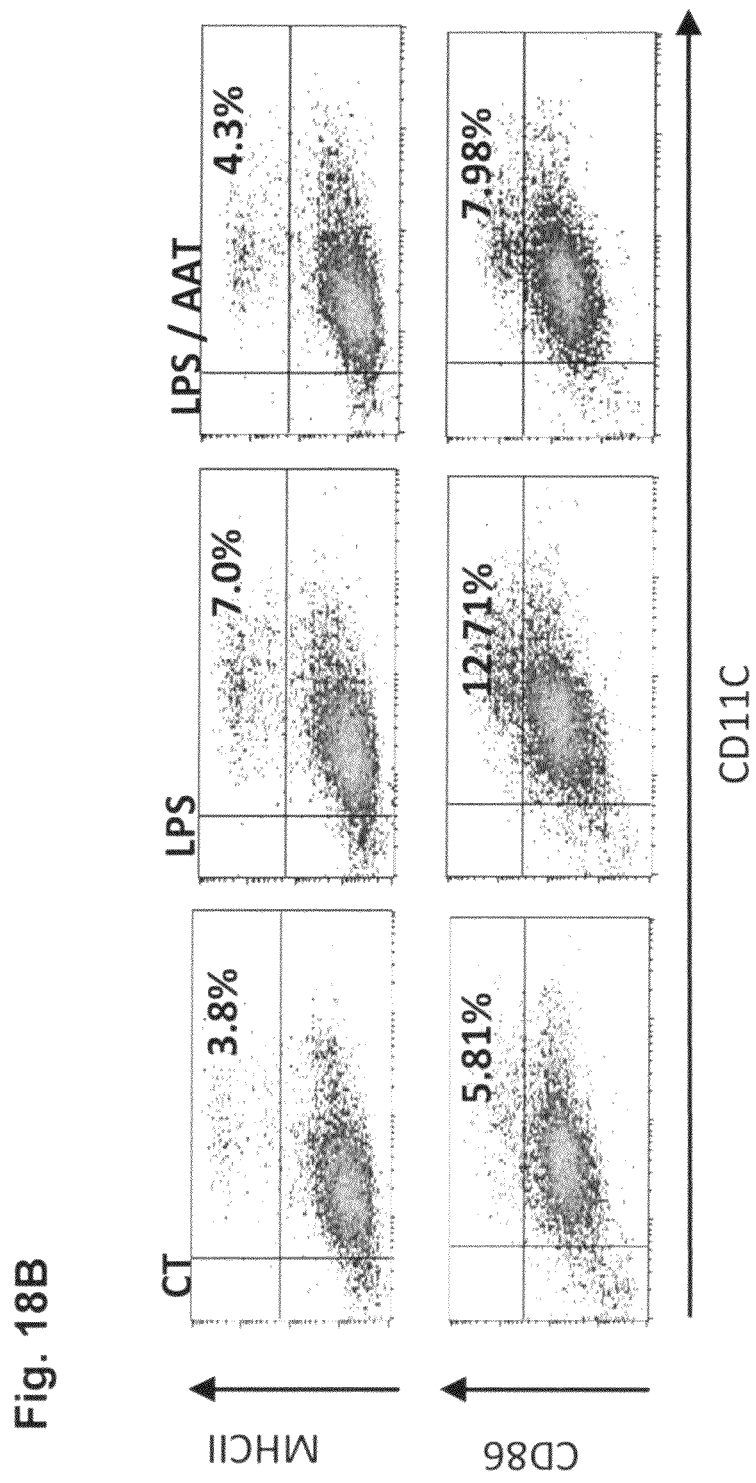

In another example, to examine the direct effect of hAAT on dendritic cell activation and maturation, dendritic cells were cultured in vitro with LPS in the absence and presence of hAAT (FIG. 18B). According to FACS analysis, LPS stimulation in the presence of hAAT resulted in a marked decrease in the levels of inducible surface MHC class II and CD86.

To address the possibility that hAAT treatment had specifically induced IL-10 production in Treg cells in vivo, hAAT or albumin were administered 3 days before LPS challenge to foxp3-GFP knock-in mice. 16 hours later spleens were harvested and splenocytes were isolated to examine IL-10 release in a cytometric secretion assay. LPS administration alone resulted in foxp3-positive cells that released IL-10 (6.1±0.1%, compared to 0.2±0.1% without LPS). The number of IL-10-secreting Treg cells increased in hAAT-treated mice to 10.6±1.2% (mean±SEM, p=0.0167).

These data support the possibility that hAAT monotherapy modifies the antigen presentation process towards the generation of a migrating, yet immature and tolerogenic dendritic cell phenotype, culminating in the expansion of functioning, IL-10-producing Tregs.

Methods

Mice.

hAAT-Tg mice, background strain C57BL/6, were engineered as described previously and studied as detailed in Supplementary Methods. Circulating levels of hAAT in heterozygote hAAT-Tg mice were determined by a specific ELISA for human AAT, as described previously. Serum levels were below the limit of detection (10 ng/ml). Wild-type Balb/c, CBA/Ca and DBA/2 mice were purchased from Jackson Laboratories.

Islet Allograft Transplantation.

Renal subcapsular islet transplantation was performed as described previously. Briefly, hAAT-Tg heterozygote mice weighing 25-30 g were rendered diabetic by a single i.p. streptozotocin injection (225 mg/kg, Sigma). Donor islets were isolated and collected on 100-micron cell strainer (BD Falcon, Franklin Lakes, N.J.), as described previously. 450 hand-picked isolated islets from DBA/2, Balb/c, C57BL/6 or CBA/Ca donor mice were grafted under the renal subcapsular space. hAAT treatment was initiated one day before transplantation and every third day (2 mg per mouse, Aralast, Baxter, Westlake Village, Calif.). Control hAAT-Tg mice received the same amount of human serum albumin (Abbott, North Chicago, Ill.). In the experiments in which monotherapy exceeded 14 days the amount of hAAT was increased by 0.5 mg every third day until a 6 mg maintenance dose was reached. Islet allograft rejection was defined as the day blood glucose exceeded 300 mg/dl after a period of at least 3 days of normoglycemia.

Skin Allografts.

1 mm³ freshly-prepared skin derived from shaved avascular portion of the abdominal midline was used as donor tissue. A graft was inserted into the subcutaneous space of each thigh in foxp3-GFP knock-in mice through a 1 mm-long incision. Incision site was sealed with a 3-0 suture.

Immunocyte Responses In Vitro.

Peripheral blood mononuclear cells (PBMC) were isolated from healthy individuals, as described previously. Studies of human blood were approved by the Colorado Multiple Institutional Review Board. Splenocytes and resident peritoneal macrophages were obtained from C57BL/6 mice, as described previously. Response assays, see Supplementary Methods.

Statistical Analysis.

Comparisons between groups were performed by two-sided t-test.

hAAT Transgenic Mice.

Experiments were performed with heterozygote hAAT-Tg mice, obtained by mating of hAAT-Tg mice with wild-type C57BL/6 mice (Jackson Laboratories, Bar Harbor, Me.). Litters were screened for the presence of the human AAT gene by standard tail DNA extraction (XNAT2 Extraction Kit, Sigma, St. Louis, Mo.) followed by two-step nested PCR amplification using the following primers:

```
outer sequence (450 bp):
forward
5'- ACTCCTCCGTACCCTCAACC-3'      (SEQ. ID NO. 62)
and reverse
5'- GCATTGCCCAGGTATTTCAT-3',     (SEQ. ID NO. 63)

and inner sequence (249 bp):
forward
5'- ACTGTCAACTTCGGGGACAC-3'      (SEQ. ID NO. 64)
and reverse
5'- CATGCCTAAACGCTTCATCA-3'.     (SEQ. ID NO. 65)
```

Assessment of Explanted Renal Allografts.

Subcapsular renal grafts were removed by nephrectomy between first and second grafting procedures under anesthesia by ligation of renal vessels and severing of the kidney together with the islet graft. Incision site was sealed with a 3-0 suture and mice were allowed to recover. Upon graft explanation, tissue was maintained on ice and islet graft sites were identified macroscopically on the surface of the kidneys. For RT-PCR, the region containing the graft was removed with a number 11 blade and immediately transferred to liquid nitrogen. An equivalent size of tissue was removed from the opposite renal pole to control for background gene expression of non-graft tissue. For histology, samples were fixed in 10% formalin.

Histology.

Kidneys or matrigel explants were fixed in buffered formalin and 24 hours later cut into two equal portions through the center of the graft for embodiment in paraffin. Blocks were sliced serially for multiple staining with either H&E, DAPI or with the following antibodies: Insulin (as previously described), VWF, CD4, CD8, CD11b and GFP (eBiosciences, San Diego, Calif.). Immunostaining methods previously described.

RT-PCR.

Total RNA was extracted (Qiagen) and reverse transcription followed (Invitrogen, Carlsbad, Calif.). Primers:

```
mouse IL-1β
                                 (SEQ. ID NO. 66)
forward      '5-CTCCATGAGCTTTGTACAAGG-3'
and (SEQ. ID NO. 67)
reverse      '5-TGCTGATGTACCAGTTGGGG-3',
```

CD14
forward    (SEQ. ID NO. 68)
and        '5-CATTTGCATCCTCCTGGTTTCTGA-3' reverse    (SEQ. ID NO. 69)
           '5-GAGTGAGTTTTCCCCTTCCGTGTG-3',

IL-2
forward    (SEQ. ID NO. 70)
and        '5-TTCAAGCTCCACTTCAAGCTCTACAGCGGAAG-3' reverse    (SEQ. ID NO. 71)
           '5-GACAGAAGGCTATCCATCTCCTCAGAAAGTCC-3',

IL-10
forward    (SEQ. ID NO. 72)
and        '5-TGTGAAAATAAGAGCAAGGCAGTG-3' reverse    (SEQ. ID NO. 73)
           '5-CATTCATGGCCTTGTAGACACC-3',

CD3ε
forward    (SEQ. ID NO. 74)
and        '5-GCCTCAGAAGCATGATAAGC-3' reverse    (SEQ. ID NO. 75)
           '5-CCCAGAGTGATACAGATGTC-3',

CD86
forward    (SEQ. ID NO. 76)
and        '5-TCCAGAACTTACGGAAGCACCCACG-3' reverse    (SEQ. ID NO. 77)
           '5-CAGGTTCACTGAAGTTGGCGATCAC-3',

ICAM-1
forward    (SEQ. ID NO. 78)
and        '5-AGGGCTGGCATTGTTCTCTA-3' reverse    (SEQ. ID NO. 79)
           '5-CTTCAGAGGCAGGAAACAGG-3',

KC
forward    (SEQ. ID NO. 80)
and        '5-CGCTCGCTTCTCTGTGCA-3' reverse    (SEQ. ID NO. 81)
           '5-ATTTTCTGAACCAAGGGAGCT-3',

MIP-2
forward    (SEQ. ID NO. 82)
and        '5-TGCCGGCTCCTCAGTGCTG-3' reverse    (SEQ. ID NO. 83)
           '5-AAACTTTTTGACCGCCCTTGA-3',

GAPDH
forward    (SEQ. ID NO. 84)
and        '5-ATTGACCACTACCTGGGCAA-3' reverse    (SEQ. ID NO. 85)
           '5-GAGATACACTTCAACACTTTGACCT-3', insulin
forward    (SEQ. ID NO. 86)
and        '5-CAGAAACCATCAGCAAGCAGG-3' reverse    (SEQ. ID NO. 87)
           '5-TTGACAAAAGCCTGGGTGGG-3',

IL-1Ra
forward    (SEQ. ID NO. 88)
and        '5-GACCCTGCAAGATGCAAGCC-3' reverse    (SEQ. ID NO. 89)
           '5-GAGCGGATGAAGGTAAAGCG-3',

IL-18BP
forward    (SEQ. ID NO. 90)
and        '5-CCCACCCTACGAAGTACCAA-3' reverse    (SEQ. ID NO. 91)
           '5-CTGGTCAAGGTCATGGTGTG-3', foxp3
forward    (SEQ. ID NO. 92)
and        '5-CCCACCTACAGGCCCTTCTC-3' reverse    (SEQ. ID NO. 93)
           '5-GGCATGGGCATCCACAGT-3',

TGFβ1
forward    (SEQ. ID NO. 94)
and        '5-GAACAAAAAGGTACATGGCCCCTGA-3' reverse    (SEQ. ID NO. 95)
           '5-CCTTCTGTTCCCTCTTCAGTGAGGTA-3',

TGFβ2
forward    (SEQ. ID NO. 96)
and        '5-ATGCCCATCGTGCACAGGGACCTCA-3' reverse    (SEQ. ID NO. 97)
           '5-CGTTCTGCCACACTGGGCTGTGA-3',

CTLA-4
forward    (SEQ. ID NO. 98)
and        '5-GTAGCCCTGCTCACTCTTCTT-3' reverse    (SEQ. ID NO. 99)
           '5-AGGTACAGTCCCGTGTCAAC-3',

VEGF
forward    (SEQ. ID NO. 100)
and        '5-GGAGATCCTTCGAGGAGCAGCACTT-3' reverse    (SEQ. ID NO. 101)
           '5-GGCGATTTAGCAGCAGATATAAGAA-3'.

FACS Analysis.

Analyses were conducted using a flow cytometer (FACS Calibur, Becton Dickinson, Mountain View, Calif.). Fluorescence data were analyzed by the Cell Quest program. At least 50,000 cells were analyzed per sample. Foxp3-GFP-positive cell analysis was performed on unstained CD4+-sorted lymphocytes ($1\times10^6$ per sample, see 'DLN analysis'). Dendritic cells ($1\times10^6$ per sample) were double-stained with CD11c-APC and anti-CD86-PE, or anti-CD11c-APC and anti-MHCII-PE (all antibodies obtained from eBioscience). Antibodies were diluted to recommended concentrations according to the manufacturer's instructions. Nonspecific binding of antibodies was assessed with cells labeled with matching isotype control antibodies. Nonspecific Fc staining was excluded by the addition of Fc-blocking antibodies (eBioscience).

IL-10 Cytometric Secretion Assay.

The assay was performed according to manufacturer's instructions (Miltenyi Biotech, Bergisch Gladbach, Germany). Briefly, an anti-CD45-pan-leukocytic chimeric antibody that also specifically binds to IL-10 was added to the freshly isolated spleen cells. During a short incubation, IL-10 that is released from activated cells is captured by the chimeric antibody and is bound to the surface of the secreting cell. Culture conditions preclude cell-to-cell association. The assay was performed on cells from foxp3-GFP knock-in mice. As such, the foxp3-positive cell subpopulation was identified by GFP and surface bound IL-10 was identified by using anti-IL-10-PE in the same cell preparation (Miltenyi Biotech).

Lymphocytic response assays.

PBMC were cultured in RPMI supplemented with 10% FCS, 50 U/ml penicillin and 50 µg/ml streptomycin (Cellgro, Herndon, Va.). Cells ($5\times10^5$ per well) were primed for 72 hours with concanavalin A (Con A, 1 µg/ml, Sigma). PBMC were then washed, resuspended ($5\times10^5$ per well) and activated with human IL-2 (Peprotech, Rocky Hill, N.J.) in the presence of hAAT or human serum albumin. Splenocytes ($5\times10^5$ per well) were stimulated with Con A (1 µg/ml) for 24 hours in the presence of hAAT or albumin. Clumping was examined microscopically. Peritoneal macrophages Cells ($5\times10^5$ per well) were stimulated for 24 hours with murine IFNγ (Peprotech) in the presence of hAAT or human serum albumin. Bone-marrow derived dendritic cells were obtained by growing bone marrow stem cells from wild-type mouse femurs in Dulbecco's Modified Eagle's Medium (DMEM) (Biological Industries, Bet Haemek, Israel) supplemented with 10% FCS, 50 µM β-mercaptoethanol (Sigma), 100 U/ml penicillin and 100 µg/ml streptomycin (Biological Industries). Cells were cultured in the presence of 10 ng/ml granulocyte-macrophage colony-stimulating factor (Biological Industries) both in the initial seeding step and again after 5 days of culture. For stimulation with LPS, the dendritic cells from 10-day cultures were mechanically removed from the culture wells with a rubber spatula, washed, and then $3\times10^6$ cells were incubated for 18 h with 100 ng/ml LPS (Sigma).

DLN Analysis.

Depending on the graft site, renal or inguinal DLN were harvested on indicated days. To examine gene expression, the lymphoid tissue was snap-frozen, total RNA extracted, quantified and normalized, and RT-PCR performed as described below. To examine the proportion of foxp3-positive Treg cells in DLN by FACS analysis, lymphoid tissue from foxp3-GFP knock-in mice was mechanically dissociated immediately after lymph node removal and CD4-positive cells sorted by magnetic-bead enrichment, according to manufacturer's instructions (EasySep MuCD4, Stem Cell Technologies, Vancouver, Canada). FACS analysis was carried out to measure percent of GFP-positive cells in the population. In migration experiments, DLN were harvested from mice that were grafted with GFP-positive allogeneic skin and the specific presence of graft-derived cells was assessed by DNA isolation and PCR amplification of the transgenic sequence as described.

Matrigel-islet Grafts.

Growth factor reduced matrigel (BD Pharmingen, Erembodegen, Belgium) remains at a liquid state at 4° C. and at a semi-solid state when introduced to mice subcutaneously. Fluid phase matrigel (0.3 ml) was mixed with 100 freshly isolated allogeneic islets from wild-type mice together with albumin or hAAT. Immediately after mixing, the matrigel-islet allografts were injected subcutaneously into the scruff region of the neck of anesthesized hAAT-Tg mice through a 21 G needle. Explanation of matrigel plugs was performed under anesthesia. One section was fixed in 10% formalin and processed for histology, the other section was immersed at 37° C. in constant stirring with dispase (BD Pharmingen) for 2 hours for gentle digestion of the matrigel and release of inhabitant and invading cells. The cells recovered from the digested matrigel were washed three times with PBS and divided into two equal parts: one part was processed for RNA extraction (Qiagen, Inc., Valencia, Calif.) followed by RT-PCR (see below). The second part was processed for genomic DNA extraction (GenScript, Piscataway, N.J.) followed by PCR for hAAT (see 'Mice').

Matrigel-skin Grafts.

A single 1 mm³ freshly-prepared skin section (see 'Skin allograft' above) was mixed with matrigel and grafted subcutaneously into the scruff region of the neck of foxp3-GFP knock-in mice. Upon matrigel harvest, one section was placed immediately on a cover slip and analyzed by fluorescent microscopy for GFP-positive cells. DAPI mounting medium was added in order to evaluate total cell content. An equal size portion of the matrigel was processed for RT-PCR analysis (see 'Matrigel-islet grafts').

Cytokine Measurements.

Murine IFNγ was measured by ELISA (BD Pharmingen) and human IFNγ was measured by electrochemiluminescence (ECL) assay using the Origen Analyzer (BioVeris, Gaithersburg, Md.), as previously described. Murine IL-6 and IL-10 levels were determined by specific ELISA (eBioscience). Murine serum cytokine levels were also measured using cytokine Proteome Profiler™ blotting according to manufacturer's instructions (R&D Systems, Minneapolis, Minn.) Nitric oxide levels were determined by Griess reaction (Promega, Madison, Wis.).

TABLE 2

Normoglycemia after islet transplantation in diabetic recipient mice during and after hAAT treatment, after graft removal and following second allografting.

| | First graft[1] | | Second graft[2] |
|---|---|---|---|
| Mouse # | hAAT treatment Days between transplant and withdrawal of hAAT | No hAAT treatment Days between withdrawal of hAAT and nephrectomy | No hAAT treatment Days from second allograft, donor strain |
| 8 | 52 | 19 | >50, DBA/2 |
| 1368 | 30 | 22 | >54, DBA/2 |
| 1439 | 30 | 24 | >52, DBA/2 |
| 1350 | 50 | 22 | Died during surgery |
| 959 | 52 | 19 | 11, CBA/Ca, H-$2^k$ |
| 981 | 52 | 26 | 11, CBA/Ca, H-$2^k$ |

[1]Donor strain: DBA/2, H-$2^d$, recipient strain: hAAT-Tg, H-$2^b$
[2]Nephrectomized hyperglycemic mice grafted with islets in contralateral renal subcapsular space Example 16

Figure 19:
FIG. 19 represents exemplary effects of AAT on stimulated human islets. Human islets were cultured in the presence of IL-1β plus IFNγ for 72 hours with indicated concentrations of AAT. (A) Morphology, (B) levels of IL-6, IL-8 and TNFα (percent from stimulated islets) and nitric oxide in supernatant.

Human islets, as well as mouse islets, are extremely sensitive to inflammatory mediators. In the presence of certain cytokines, islets will loose their rounded dense morphology and become injured; critical islet mass will be lost in the first 48 hours after transplantation, requiring more than one donor per diabetic human recipient of an islet graft. In one exemplary method, FIG. 19 represents the effects of AAT on stimulated human islets. Human islets were cultured in the presence of IL-1β plus IFNγ for 72 hours with indicated concentrations of AAT. As illustrated in FIG. 19, there are morphological indications in islets incubated with AAT compared to control islets from the same donor without AAT.

Figure 20:
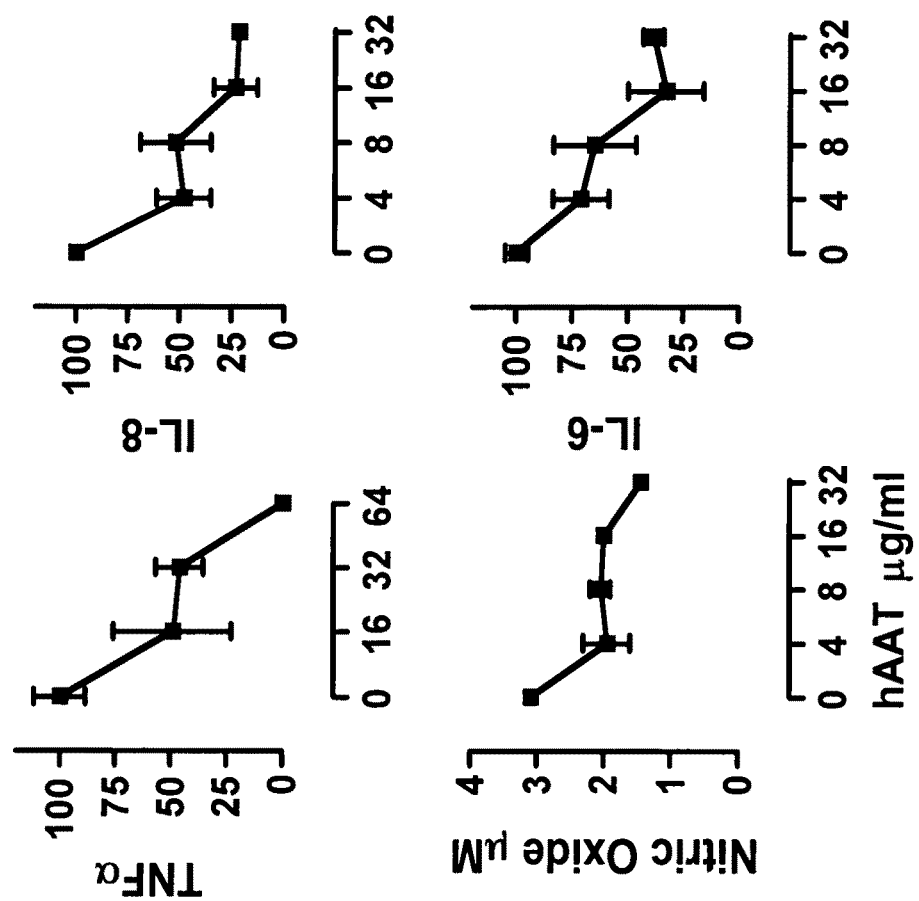
FIG. 20 represents exemplary graphs of effects of AAT on stimulated human islets. Human islets were cultured in the presence of IL-1β plus IFNγ for 72 hours with indicated concentrations of AAT, levels of IL-6, IL-8 and TNFα (percent from stimulated islets) and nitric oxide in supernatant were examined.

The multicellular islet contains cells capable of secreting important inflammatory agents. Upon transplantation, these contribute to loss of graft. AAT reduced the amounts of critical cytokines secreted by islets in response to inflammation, and lowered nitric oxide levels. Islets were cultured in the presence of IL-1β plus IFNγ for 72 hours with indicated concentrations of AAT (micrograms/mL)) As shown in FIG. 20, levels of IL-6, IL-8 and TNFα (percent from stimulated islets) and nitric oxide were determined in supernatants. Data are mean levels 5 islet donors.

Figure 21:
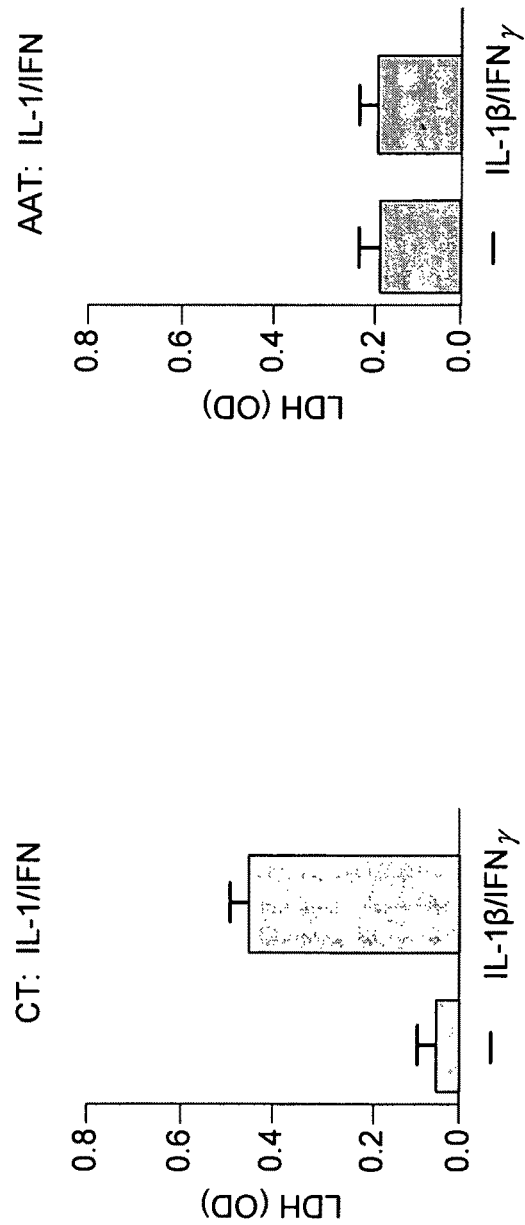
FIG. 21 represents exemplary experiments where right after isolation, islet cells were supplemented with AAT (or left untreated, CT) for 24 hrs. The cells were then washed and incubated for 72 hours with IL-1β and IFNγ, without AAT. LDH was measured in supernatants.

When added immediately after isolation, a procedure possible only in a center where human islet cells are isolated, islet cell death driven by exogenous cytokines (as would occur during transplantation) is abolished. The effect of AAT inhibition in the experiment is represented in FIG. 21. As shown, CT (control) are islets incubated without AAT and the LDH levels (indicator of cell death) are elevated when exposed to the combination of IL-1β plus IFNγ. On the right, islets were exposed to the combination of IL-1β plus IFNγ in the presence of AAT (0.5 mg/mL) and LDH levels were the same as in islets without IL-1β plus IFNγ.

Example 17

In another exemplary method, a subject scheduled for a transplant is treated with an AAT composition intravenously. In this example, a patient is identified in need of transplant surgery. The patient is administered an infusion via iv of an AAT composition (e.g. 60 mg/kg of Aralast AAT). Then the patient is sent to the fluoroscopy room where a catheter is implanted in a portal vein under fluoroscopy and islet cells are infused directly into the subject (e.g. where the cells then lodge in the liver). Later, for example 2 days after transplant of the islet cells, a patient is treated with another iv infusion of an AAT composition (e.g. 60 mg/kg of Aralast AAT). In addition, the patient may be treated in another several days, for example, about 5 days later with another iv infusion of an AAT composition (e.g. 60 mg/kg of Aralast AAT). In order to assess whether periodic administration of an AAT composition is needed, blood glucose levels of the patient can be measured to assess immune tolerance of the transplanted cells and administration of additional AAT composition infusions can be determined and delivered as needed. In addition, the patient can be monitored for anti-inflammatory levels using for example drawing one or more blood samples from a patient and assessing the level of anti-inflammatory compounds in the blood (e.g. cytokine levels in the blood). In this example, depending on patient need, AAT compositions can be administered, before, during and/or after islet cell transplantation.

Additional Methods

In one exemplary method, AAT used in these studies is purified from the blood of healthy volunteers. AAT is purified to single-band homogeneity. The AAT protein is diafiltered into a diluent consisting of NaCl, sodium phosphate, pH 7.05. The AAT preparations are maintained at stock concentrations of 14-50 mg/ml and stored at −70.degree. C. until added to cultures. As a control AAT preparation that is different from the composition of the invention a commercially available Prolastin (Bayer's AAT) is used. Recombinant human interleukin 18 (IL-18) is obtained from Vertex Pharmaceuticals Inc., (Cambridge, Mass.). IL-6 and tumor necrosis factor (TNF) are obtained from R & D Systems, Minneapolis, Minn., endotoxin-free NaCl, and endotoxin (lipopolysaccharide, LPS) is obtained from Sigma (St. Louis, Mo.). Here is the heat inactivation graph.

U1 Cells

Medium for monocytic U1 cell and MAGI-CCR5 cell cultures consists of RPMI 1640 medium purchased from Mediatech (Hermdon, Va.) containing 2.5 mM L-glutamine, 25 mM Hepes, 100 units/ml penicillin and streptomycin (GIBCO/BRL, Rockville, Md.) with 10% or 7.5% (vol/vol) heat-inactivated fetal bovine serum (FBS, GIBCO) for U1 cell and MAGI-CCR5 cell cultures, respectively. PBMC are cultured in R3 medium consisting of RPMI 1640 medium (Mediatech), 20% FBS (GIBCO), 100 units/ml penicillin and streptomycin (GIBCO) and 5% (vol/vol) IL-2 (Hemagen, Waltham, Mass.).

U1 monocytic cell assay. U1 cells can be obtained from the AIDS Research and Reference Reagent Program, National Institute of Allergy and Infectious Diseases, NIH. U1 cells are maintained in T-175 polystyrene flasks (Falcon, Becton Dickinson, Franklin Lakes, N.J.) in medium and used when in log phase growth. Cells are counted in a hemacytometer, examined for viability by Trypan blue exclusion (>95% for all experiments) and resuspended in fresh medium at $2 \times 10^6$ per ml. Two-hundred fifty ml of cell suspension are added to wells of 24-well polystyrene tissue culture plates (Falcon), followed by the addition of medium or AAT to produce the final concentration to be tested in a volume of 450 ml. After 1.0 hr of incubation (37° C., 5% $CO_2$), 50 ml of medium (control) or stimulus diluted in medium are added to wells to produce the final concentration of stimulus to be tested. The final culture volumes are 500 ml and contained $1 \times 10^6$ cells per ml. After 48 hr of incubation (37° C., 5% $CO_2$) 50 ml of 10% (vol/vol) Triton-X-100 is added to each culture (final concentration of 1% vol/vol), and cultures are frozen and thawed once. This is followed by assay for HIV p24 antigen by ELISA with a lower limit of detection of 31 pg/ml (NCI-Frederick Cancer Research and Development Center, Frederick, Md.). The disruption of cells due to the addition of Triton-X-100 and the freeze-thaw cycle produced cell lysates and enabled assessment of total (secreted and cell-associated) production of p24 antigen.

Example 18

Blood Draw: In certain exemplary methods, first blood was drawn into syringes containing heparin (10 20 U/mL, or use commercial heparinized sterile tubes) and second, cells were separated. In one particular example, 1.0 mL blood provides $1 \times 10^6$ PBMC and about $2.5 \times 10^6$ PBMC per tube were used for these experimental examples.

Cell Separation can include for example:
a) 20 mL sterile saline is added to 50 ml polypropylene tubes.
b) Put 10 mL whole blood into each 50 mL polypropylene tube.
c) Underlay each tube with 10 mL ficoll hypaque using a pipette or a spinal needle, proceed at a rate of about 1 minute per underlay.
d) Centrifuge the tubes at 1,250 rpm (=400 g)×40 minutes at room temperature.
e) Harvest PBMC layers from 2 tubes using a 10 ml pipette and place into a fresh 50 ml polypropylene tube.
f) Fill tubes to 50 mL with saline.
g) Centrifuge tubes at 1,000 rpm×10 minutes at room temperature.
h) Decant supernatant.
i) Resuspend cells in 10 mL saline and combine all tubes into as few tubes as possible.
j) Fill tube(s) to 50 mL with saline.
k) Centrifuge tube(s) at 1,000 rpm×10 minutes at room temperature.
l) Decant supernatant.
m) Resuspend the cells with a pipette in EXACTLY 10 mL of saline.
n) Count cells in a hemacytometer (total #).

o) Add an additional 40 mL of saline to the tube(s); each now contains 50 mL liquid.
p) Centrifuge the tubes at 1,000 rpm×10 minutes at room temperature.
q) Decant supernatant.
r) Resuspend cells at $1\times10^6$/mL in sterile R3 tissue culture medium (RPMI 1640 medium with 20% [vol/vol] heat-inactivated fetal bovine serum, 5% [vol/vol] Interleukin (IL)-2 and penicillin 100 units/ml+streptomycin 100 µg/ml) supplemented 3.3 µg/ml PHA.

Third, cells were induced into blast phase by culture by incubation for 2 days (37° C., 5% CO2) in sterile tissue culture flasks.

Fourth, PBMC were then infected with HIV: After the 2 days of blasting/incubation, the cells were counted and the number of PBMC was determined for infecting with HIV. A cell suspension was aliquoted into a polypropylene tube, then centrifuged into a pellet. Then, the tubes are inverted right away, preserving the cell pellet: approximately 300 µl of liquid remains with the cell pellet. The virus of choice was added. For the X4/T tropic A018A strain, the PBMC was infected with 200 TCID50 per 1 million PBMC. For the R5/M tropic virus strain, 300 TCID50 per 1 million PBMC was used for infection. After adding the virus, the virus was resuspended vigorously with a pipetter and vortex as well. Then the cells were incubated in the 50 ml polypropylene tube (loose cap) for 3 hrs in an incubator. c) After 3 hrs of incubation, the infected PBMC were washed with RPMI or with PBS (resuspend with a vacuum pipetter), then centrifuge. No significant amount of virus remains after this step. d) The infected PBMC was resuspended at $2\times10^6$ per ml in non-blasting R3 medium=R3 medium as above but without PHA. (=RPMI+ 10% FCS+5% IL 2).

Fifth, the cell suspension was aliquoted into 24-well polystyrene plates at a final concentration of $1\times10^6$ per ml. Sixth, a time zero sample was created by taking a 250 µl aliquot of cell suspension at $2\times10^6$ cells per ml and add this into a 1.5 ml Eppendorf tube. Add to this 250 µl of medium and 50 µl of (10% vol/vol) Triton X 100. The sample is froze immediately at −70° C. and assay later for p24 antigen as the time 0 specimen. Seventh, 250 µl of cell suspension was added to each well with an additional 250 µl of R3 medium alone (Spontaneous, or AAT=0), or R3 that contains AAT (either Aralast® or Zemaira®) at twice the final desired concentrations. The final volume of each culture is 500 µl. Eighth, the tissue culture plates were incubated with cell cultures in an incubator (37° C., 5% CO2), for 4 days, then add 50 µl of 10% (vol/vol) Triton X 100 to make a final Triton X 100 concentration of 1% vol/vol. Finally HIV p24 antigen was quantified using an ELISA assay.

Figure 22:
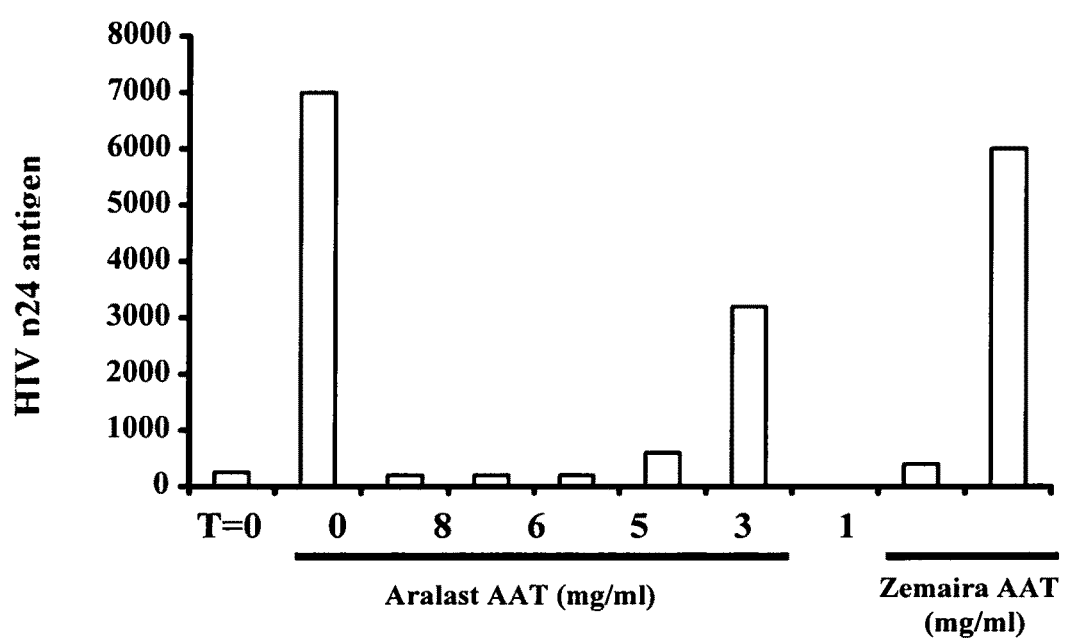
FIG. 22 represents an exemplary comparison of AAT (Aralast™ or Zemaira™) and their respective effects on HIV production in infected peripheral blood mononuclear cells (PBMC).

As demonstrated in exemplary FIG. 22, Aralast substantially induced HIV inhibition at all concentrations tested (compared to AAT=0 cultures), with nearly 100% suppression observed using Aralast at 3.0 8.0 mg/ml, and about 50% HIV suppression using Aralast at 1.0 mg/ml. In contrast, Zemaira AAT demonstrated minimal HIV suppression at 7.0 mg/ml, and near complete suppression was obtained at 15.0 mg/ml. In this exemplary method, there was a large difference in dose response demonstrating that Aralast is more potent than Zemaira as an inhibitor of HIV infection in primary PBMC. Since Aralast and Zemaira are quantified by biological activity (1.0 mg Aralast=1.0 mg Zemaira=1.0 mg of serine protease inhibitor activity), this experiment indicates that the ability of AAT to suppress HIV is independent of serine protease inhibition. If the serine protease inhibitor function of AAT accounts for the HIV suppression, Aralast and Zemaira would inhibit HIV production equivalently.

Exemplary Procedures for Heat Inactivation (HI) of AAT

In another exemplary method, a predetermined volume (e.g. 2 mls) of a stock solution such as 20 mg/ml of AAT (e.g. Aralast) was placed in a test tube. The stock sample was heat treated in boiling water (95° C.) for 30 min. The solution was allowed to cool. Then the heated solution was transferred back to eppendorf tube(s). If any volume has boiled off (usually about 10%), the volume is replaced with a solution to near original volume using for example, PBS. Then the solution is tested for remaining serine protease activity using a serine protease inhibitor assay. It was demonstrated that no significant serine protease inhibitor activity could be detected for up to 3 days later (data not shown).

Example 19

Elastase assay: In one example, an enzymatic assay of elastase biological activity (Bieth J, et. al 1974) was used to compare AAT and heat-inactivated (HI) AAT.

Elastase-induced hydrolysis of the N-Succinyl-Ala-Ala-Ala-p-nitroanalide serine protease substrate (e.g., Sigma, St. Louis, Mo.) liberates p-nitroanaline, which can be measured at an absorbance of 410 nm. Elastase (e.g., Sigma) is diluted to 20 µg/ml in 100 mM tris-HCl, pH 8.0. Ten microliters AAT (at 20 mg/ml) or PBS (Control without AAT, set at 100% elastase activity) is mixed with 50 µl of diluted elastase and incubated for 20 mins at 25° C. Ten microliters of the alpha-1-antitrypsin/elastase or PBS/elastase solutions are added to 180 µl of substrate (alpha-1-antitrypsin, which was diluted to 135 µg/ml with 100 nM Tris HCl. pH 8.0) and transferred into wells of a 96 well flat bottom plate. An increase in absorbance (A) 410 nm (which indicated elastase-induced generation of p-nitroanaline) was measured serially over a 5 minute time period. Elastase alone was used as a Control (set at 100% elastase activity). The presence of a serine protease inhibitor (e.g., AAT) blocks elastase activity and suppresses liberation of p-nitroanaline (quantified as A410).

Figure 24:
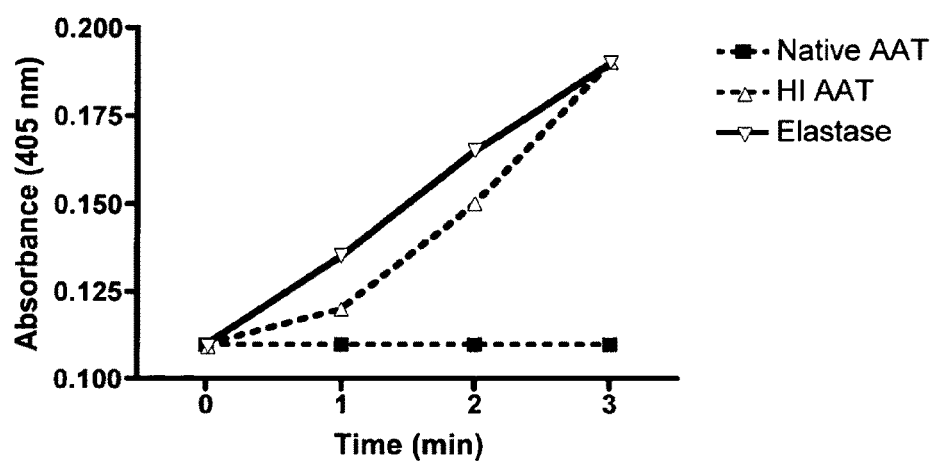
FIG. 24 represents an exemplary graph demonstrating HI AAT and AAT Elastase binding activity. Elastase alone is a control.

As represented in FIG. 24, elastase alone (no AAT) processed the N-Succinyl-Ala-Ala-Ala-p-nitroanalide substrate, which generated a step increase in absorbance (A410, curve labeled Elastase). Combining native (NOT heat-inactivated) AAT ablated elastase processing of the N-Succinyl-Ala-Ala-Ala-p-nitroanalide substrate and blocked the increase in A410 nm (curve labeled AAT+Elastase). In marked contrast, combining HIAAT with elastase produced a curve similar to that of elastase alone. This demonstrated that HIAAT possessed no detectable elastase neutralizing activity, since the elastase-induce generation of p-nitroanaline due to processing of the substrate N-Succinyl-Ala-Ala-Ala-p-nitroanalide was unaffected (see curve labeled HIAAT+Elastase and compare to curve labeled Elastase).

Example 20

Heat-Inactivated AAT (ΔAAT) Retains Biological Activity in Human Primary Fibroblasts In another exemplary method, human fetal foreskin fibroblasts were obtained. Fibroblasts were grown in culture medium (e.g. RPMI 1640 medium with 10% [vol/vol] heat inactivated fetal bovine serum) in 150 mL polystyrene tissue culture flasks (Falcon, Lincoln Park, N.J.) and incubated at 37° C. and 5% $CO_2$ until confluent. The cells were detached using trypsin and split into 24-well polystyrene cell culture plates. The cells were then allowed to grow to confluence in these plates for 3-5 days before the actual experiments were performed. Cells were incubated (37° C., 5% CO2) in culture medium alone (Control), AAT alone, or with heat inactivated AAT (ΔAAT). After 24 hours of incubation (37° C., 5% CO2) supernatants were removed and frozen (−70° C.) until assay for IL-6 (Interleukin 6 FIG. 23A) and IL-8 (Interleukin 8 FIG. 23B).

Figures 23A, 23B:
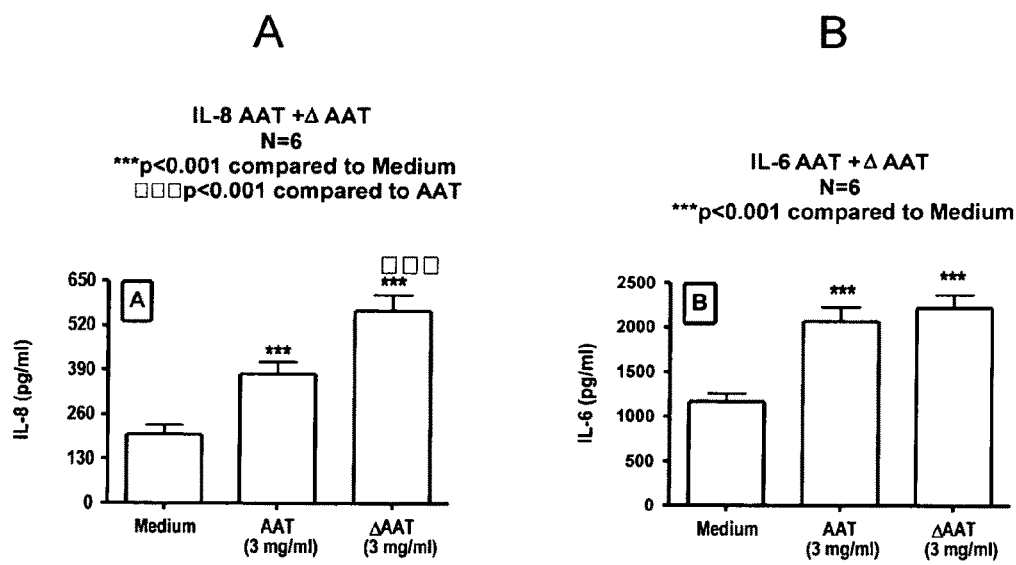
FIGS. 23A and 23B represents an exemplary histogram of Heat-inactivated AAT (ΔAAT/HI AAT) or native AAT on interleukin 8 (IL-8, 23A) or (IL-6, 23B) induction in human primary fibroblasts.

FIGS. 23A and 23B represents an exemplary experiment where ΔAAT was shown to be devoid of serine protease inhibitor function by in vitro assay. As shown in FIGS. 23A and 23B the presence of 3.0 mg/ml Aralast AAT significantly increased the synthesis of (23A) IL 8 and (23B) IL 6 production in 24-hour fibroblast cultures (compared to control cells in medium alone, labeled Medium). Interestingly, parallel cultures conducted using 3.0 mg/ml Aralast ΔAAT resulted in similar production of (2A) of IL-8 and enhanced production (2B) of IL-6 in the fibroblasts compared to control (medium alone) cultures. These data demonstrate that heat inactivation of the serine protease inhibitor function of AAT does not abrogate this AAT biological activity (e.g. cytokine production). Thus, these AAT functions are separate from serine protease inhibition which accounts for certain AAT biological activities. The data illustrated in FIGS. 22, 23A and 23B demonstrate that AAT suppression of HIV in primary infected PBMC in vitro, and AAT induction of cytokines in human primary fibroblasts in vitro are both independent of AAT induced serine protease inhibition.

Example 21

Anti-HIV Effect of AAT

Figure 25A:
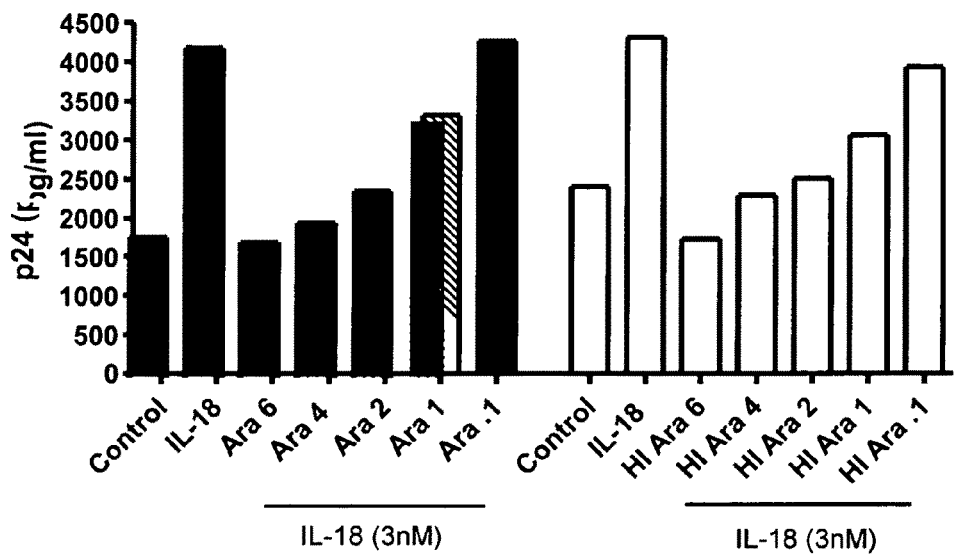
FIGS. 25A and 25B represents an exemplary histogram of the effects of AAT (4A left panel, solid bars) or HI AAT (25A right panel, open bars) at 0, 6, 4, 2 and 1 mg/ml on HIV production represented by p24 production (pg/ml) in stimulated U1 cells.
Figure 25B:
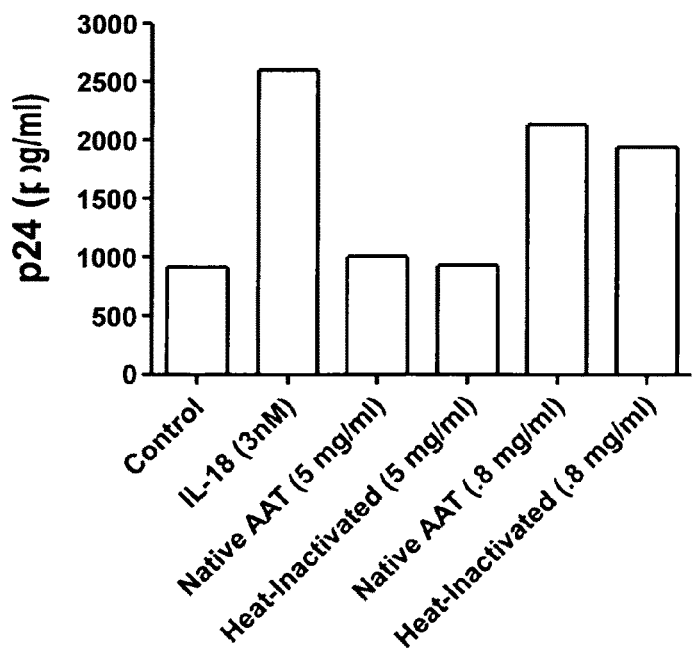

In one exemplary method it was demonstrated that AAT and HIAAT (ΔAAT) inhibit HIV production in chronically infected U1 cells. U1 cells are derived from the U937 human monocytic cell line by the stable incorporation of 2 copies of HIV provirus into the cell genome. These cells generate increased HIV following exposure to any of several stimuli. In these exemplary experiments, U1 cells were cultured at a density of $1\times10^6$ cells per ml in 500 μl of medium consisting of RPMI 1640 medium with 10% [vol/vol] heat inactivated fetal calf serum, with penicillin 100 units/ml+streptomycin 100 μg/ml. Cells were cultured in wells of a polystyrene tissue culture plate with medium alone (control), with medium containing stimulus alone (3 nM IL 18), or with stimulus in the presence of AAT (FIG. 25A, left panel) or heat inactivated AAT (FIG. 25A, right panel). AAT was added to cultures 1.0 hr prior to the addition of IL-18 (interleukin 18) stimulus. Cultures were incubated for 24 hrs (37° C., 5% $CO_2$), and then lysed with 1% (vol/vol) triton X 100 and then the lysates were assayed for HIV p24 antigen using an ELISA. As shown in FIGS. 25A and 25B, IL-18 stimulated an increase in HIV production compared to medium alone (control) cultures. Stimulating U1 cell cultures with IL-18 in the presence of either unaltered (FIG. 25A, left panel) AAT or with heat inactivated AAT (FIG. 25A, right panel) resulted in dose dependent inhibition of stimulated HIV production. Comparing native with heat inactivated AAT showed very similar inhibition of p24 production. For both native and heat inactivated AAT, nearly complete HIV suppression induced by IL 18 was observed using AAT concentrations of 4 and 6 mg/ml. These results suggest very similar HIV suppression in this chronic infection model using native or heat inactivated AAT. Another experiment was performed using 0.8 or 5 mg/ml of AAT or HI AAT (FIG. 25B). For both native and heat inactivated AAT, nearly complete HIV suppression induced by IL 18 was observed using AAT of HI AAT concentrations of 5 mg/ml but not at 0.8 mg/ml. Since heat inactivation of AAT using our protocol ablates AAT serine protease inhibitory function (as documented in by an in vitro serine protease neutralization assay, data not shown), these results suggest that AAT suppression of HIV in these studies does not depend on the serine protease inhibitor function of AAT.

Example 22

In another exemplary method, AAT (Native AAT) and HI AAT activity were analyzed for their effects on lethal toxin-induced cytotoxicity in RAW 264.7 cells (N=5). In this example, all cultures received a lethal toxin (100 ng/ml protective antigen+40 ng/ml lethal factor); p<0.001 compared to Control. This exemplary study was used to demonstrate HI AAT versus native AAT treatments on cells exposed to anthrax.

Figure 26:
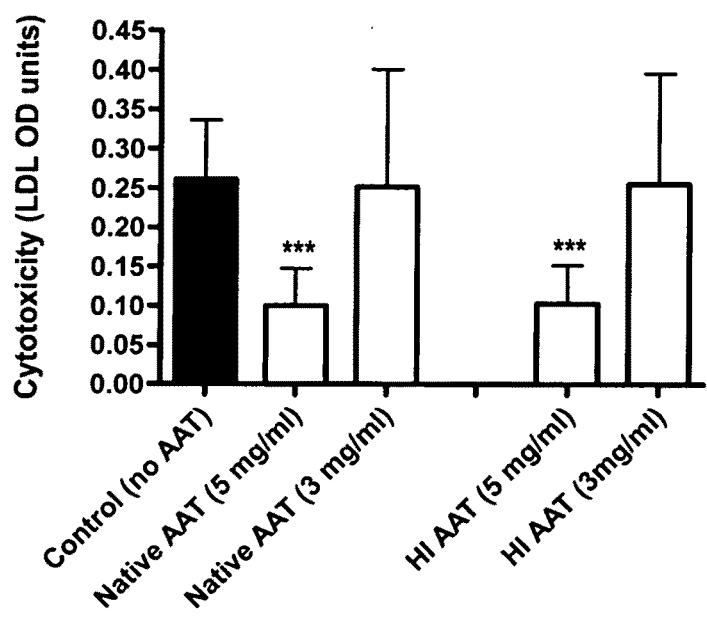
FIG. 26 represents an exemplary histogram of AAT (open bars, left) and HI AAT (open bars, right) on lethal toxin-induced cytotoxicity (LDL OD units) in Raw 264.7 cells. A control is represented by a solid bar.

RAW 264.7 cells were cultured in medium (RPMI 1640 medium+10 heat-inactivated FBS with 100 units/ml penicillin and 100 μg/ml streptomycin) containing lethal toxin (LT) alone (control), or in medium containing LT and AAT. AAT was added 1 hr prior to addition of LT. Three hrs after addition of LT, cell culture supernatant was assayed for cytotoxicity using an LDH release assay (Promega, Madison, Wis.). As shown in FIG. 26, cells cultured in LT alone (Control, closed bar) demonstrated cytotoxicity that produced a mean of approximately 0.25 OD units (LDL OD units on the vertical axis represents increasing amounts of cytotoxicity. Five mg/ml native (not heat-inactivated) AAT significantly reduced the LT-induced cytotoxicity in the RAW 264.7 cells), whereas 3.0 mg/ml native AAT did not inhibit LT cytotoxicity. As shown in the same figure, HI AAT replicated the native AAT results almost identically, with 5.0 mg/ml HI AAT significantly reducing LT-induced cytotoxicity. In this Figure results from 5 separate experiments are shown (mean±SEM), and *** indicates p<0.001 compared to Control (no AAT, closed bar). These data show that HI AAT is equivalent to native AAT as an inhibitor of anthrax cytotoxicity in vitro.

Methods

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

Apoptosis Assay. The protective effect of AAT on islets may address one of the major obstacles in islet transplantation today, namely the inadequacy of islet mass and post-isolation islet viability. Freshly isolated human islets activate stress signaling pathways and exhibit high rate of apoptosis due to the process of isolation, necessitating the use of more than one islet donor per diabetic patient (Nanji, (2004); Abdelli, S. et al. Intracellular stress signaling pathways activated during human islet preparation and following acute cytokine exposure. Diabetes 53, 2815-23 (2004)).

AAT dosage. Normal human plasma contains 0.8-2.4 mg/ml AAT, with a half life of 5-6 days.

Example 23

HI AAT Reduces LT Induced Lethality in a Murine Model of Anthrax Toxicity

Figure 27:
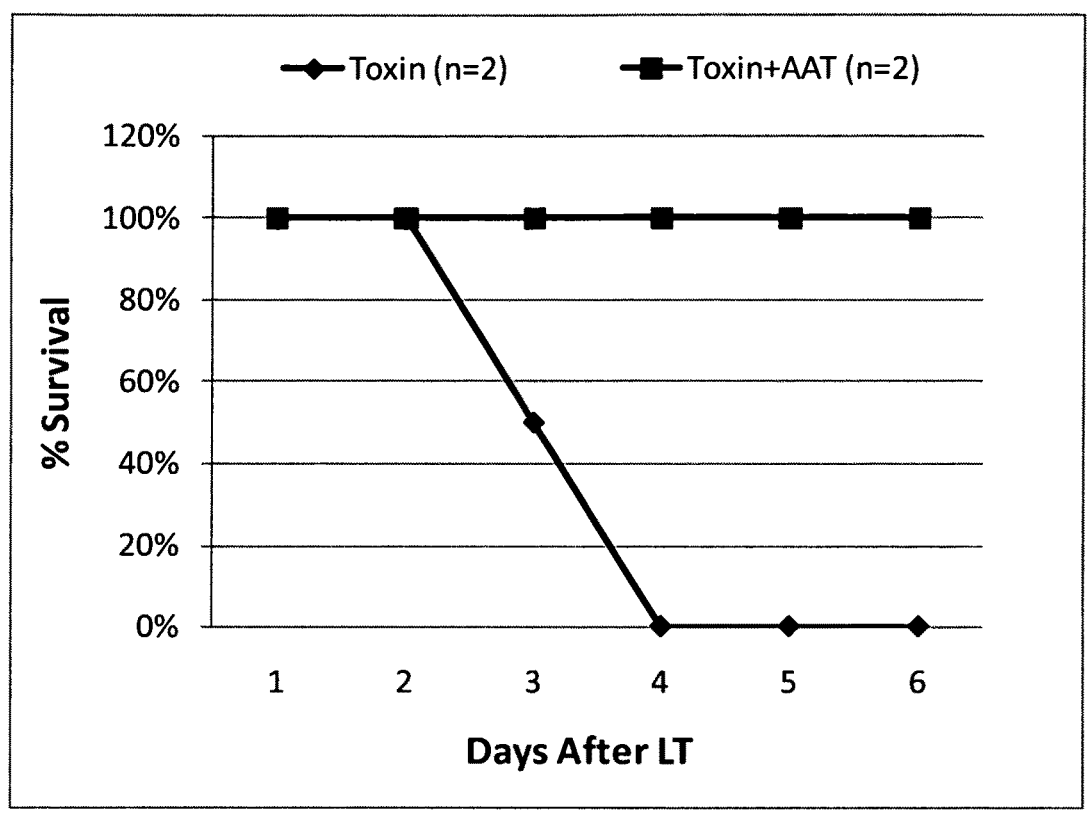
FIG. 27 represents an exemplary experiment of post-toxin treatment of mice with and without heat-inactivated AAT.

Post-Toxin Treatment: For this experiment, LT (60 μg PA and 20 μg LF) was administered as a single intraperitoneal (ip) injection to induce lethality in female Balb/c mice (Jackson Laboratory, Bar Harbor, Me.). HI AAT was introduced as a subcutaneous (sc) injection at the nape of the neck in order to separate HI AAT from LT and avoid artifact due to physical combination at the point of delivery. For the treatment arm (n=2), 2 mg of HI AAT was given immediately after LT injection (i.e., t=0). The results using this model of anthrax LT-induced lethality with HI AAT as a candidate therapy are summarized in the survival curves shown in FIG. 27. As depicted, both mice given LT alone died by day 4 (n=2; diamonds). In contrast, both of the mice given HI AAT in addition to LT remained clinically healthy through day 6 (n=2; squares). It is also important to note that the mice treated with HI AAT remained clinically healthy throughout the observation period.

Figure 28:
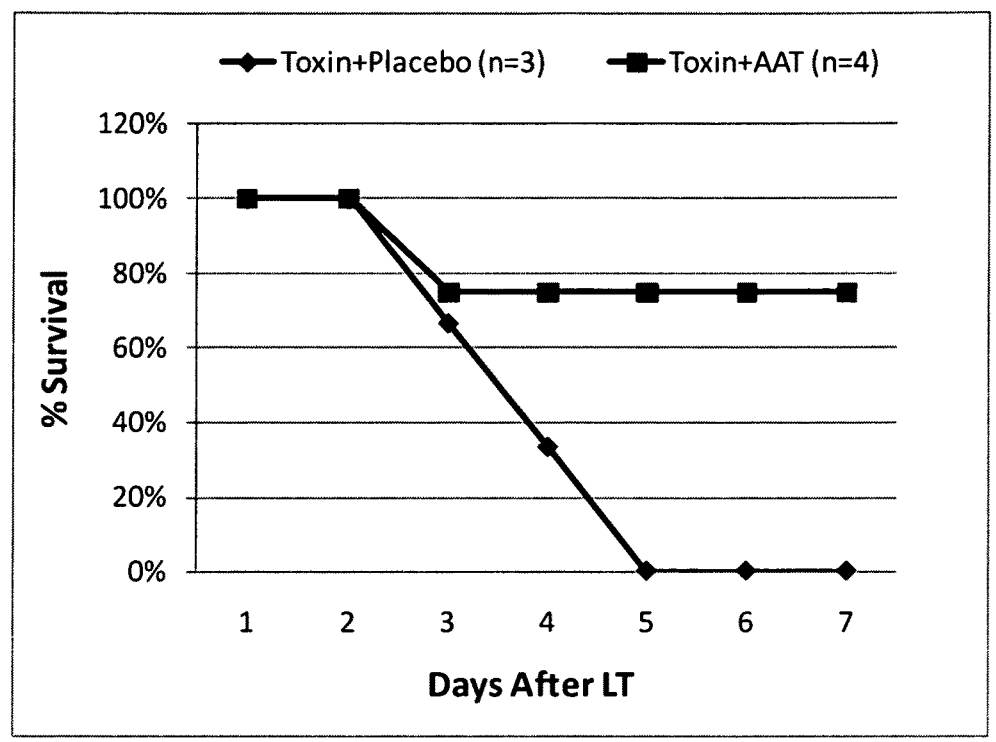
FIG. 28 represents an exemplary experiment of post-toxin treatment of mice with heat-inactivated AAT or placebo.

Post-Toxin Treatment with HI AAT or Placebo: For this experiment LT (60 μg PA and 20 μg LF) was administered as a single intraperitoneal (ip) injection to induce lethality in female Balb/c mice (Jackson Laboratory, Bar Harbor, Me.). HI AAT, or human albumin as a benign placebo protein, were introduced as a subcutaneous (sc) injection at the nape of the neck in order to separate HI AAT or albumin from LT and avoid artifact due to physical combination at the point of delivery. For the treatment arm, 2 mg of AAT was given once immediately after LT injection; and for the placebo arm, 2 mg of human albumin was given once immediately after LT injection. The results using this model of anthrax LT-induced lethality with HI AAT as a candidate therapy are summarized in the survival curves shown in FIG. 28. As depicted, all mice given LT and placebo (n=3) died by day 5 (diamonds). In contrast, only one of the mice given LT followed by HI AAT (n=4) died through day 7 (open squares); representing an observed treatment efficacy of 75%.

In order to assess the potential for HI AAT to ameliorate symptoms associated with exposure to anthrax toxin, the mice in this experiment were also scored on a scale of 1 to 5 for their clinical well being over time; with a score of 1 representing completely healthy and a score of 5 indicaticatin that the mice were unable to move even after prodding. As seen in Table 1, in addition to preventing the symptom of death; with one exception, HI AAT treatment also almost entirely prevented any observable-clinical symptoms associated with exposure to anthrax LT.

TABLE 1

Clinical Disease Progression in female Balb/c mice exposed to LT and treated with HI AAT or Placebo (human albumin):

| Day | Toxin + Placebo (n = 3) Mouse | | | Toxin + HI AAT (n = 4) Mouse | | | |
|-----|---|---|---|---|---|---|---|
|     | A | B | C | D | E | F | G |
| 1 | 1 | 1 | 1 | 1 | 1 | 1 | 1 |
| 2 | na | na | na | na | na | na | na |
| 3 | dead | 4.5 | 4.5 | dead | 1 | 1 | 1 |
| 4 | dead | dead | 4.5 | dead | 1 | 1 | 1 |
| 5 | dead | dead | dead | dead | 1 | 1 | 1 |
| 6 | dead | dead | dead | dead | 1 | 1 | 1 |
| 7 | dead | dead | dead | dead | 1 | 1 | 1 | na: no observations
1 Healthy
5 Very Sick
6 Dead

Example 24

Figures 29A, 29B:
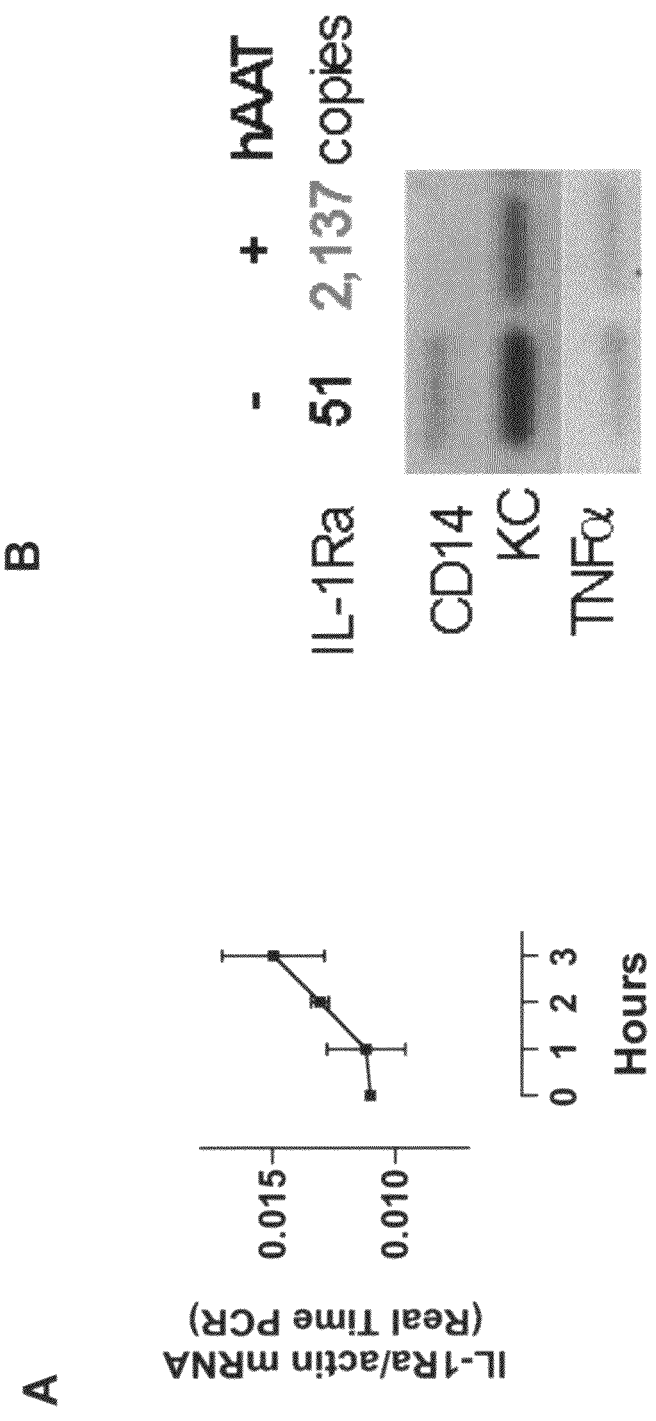
FIGS. 29A-29B represent in A. an exemplary plot measuring levels of an interleulin protein compared to a control and in B an exemplary gel illustrating levels of an interleukin in the presence or absence of AAT.

FIGS. 29A and 29B represent effects of AAT on islet-derived IL-1Ra. In one study, islet IL-1Ra mRNA was shown to increase during AAT treatment of cultured mouse islets (FIG. 29A) and that AAT-treated grafted islets contain more IL-1Ra transcripts 48 hrs after transplantation, corresponding to decreased intragraft CD14, KC and TNFα levels (FIG. 29B). (A) in vitro. Mouse islets (50 per well in triplicates) were incubated with 0.5 mg/ml hAAT (Aralast, Baxter) and mRNA was generated at indicated time points. mRNA transcript levels were determined by real-time PCR. (B) In vivo. 450 mouse islets were incubated for 48 hours with or without hAAT (0.5 mg/ml) and then grafted into allogeneic recipient mice. 48 hours later grafts were excised and RT-PCR performed. IL-1Ra was determined by real-time PCR, proinflammatory markers by semi-quantitative PCR. Representative results from three transplantations.

Figures 30A, 30B, 30C:
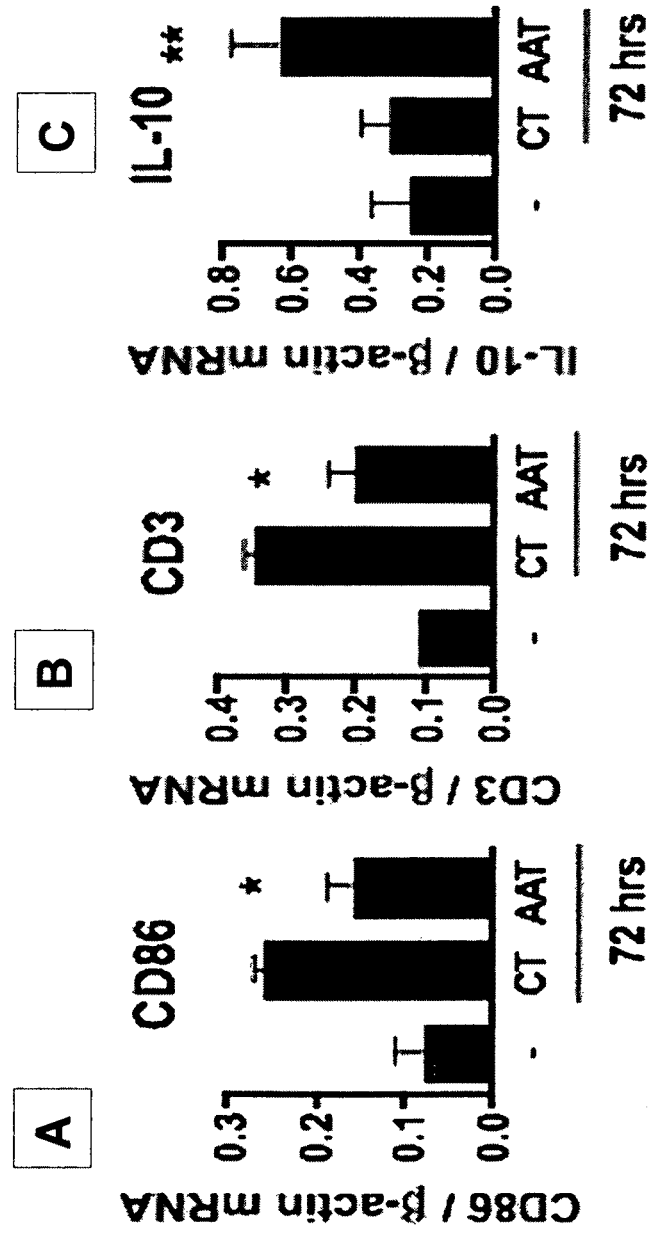
FIGS. 30A-30C represent exemplary plots of levels of various cytokines in the presence or absence of AAT at pre-determined time periods of certain embodiments of the present invention.

FIGS. 30A-30C illustrates effect of AAT on dendritic cell maturation. Seventy-two hours after allogeneic skin grafting under the renal capsule, renal DLNs were harvested and examined by RT-PCR. DLN from nongrafted mice (left bar) is compared with 72-h DLN gene expression from untreated (CT) and hAAT-treated (AAT) mice. Shown are mean±SEM from three experiments. *P<0.05; **P<0.01 between CT and AAT.

Example 25

FIG. 31 illustrates a table representing mutation in hAAT reactive center loop chosen for analysis. The choice of the minimal point mutation required for loss of elastase inhibition. Top frame, native hAAT; Bottom frame, hAATcys in which Proline is replace by cysteine.

Example 26 pEF-hAAT, contains the EF vector from Epstein Barr Virus (EBV). EBV is a human herpes virus that is capable of maintaining its genome extra-chromosomally in dividing primate cells and targets the liver upon infection. The EF vector is also able to hold large genetic sequences. pEF-hAAT holds the entire hAAT gene (introns/exons/promoter) which makes this plasmid a useful tool in hAAT gene therapy experiments. The mice used in the following experiments are C57BI/6 heterozygote for hAAT cDNA which is expressed only in the lungs, as recently reported by our group. The hAAT heterozygote mice display undetectable hAAT levels in their serum, as tested by ELISA, but are able to accept exogenous hAAT without mounting an immune response to the human protein. In vitro, the mouse hepatocytic cell line HepalC can be used for the study of transfected hAAT.

Figure 32:
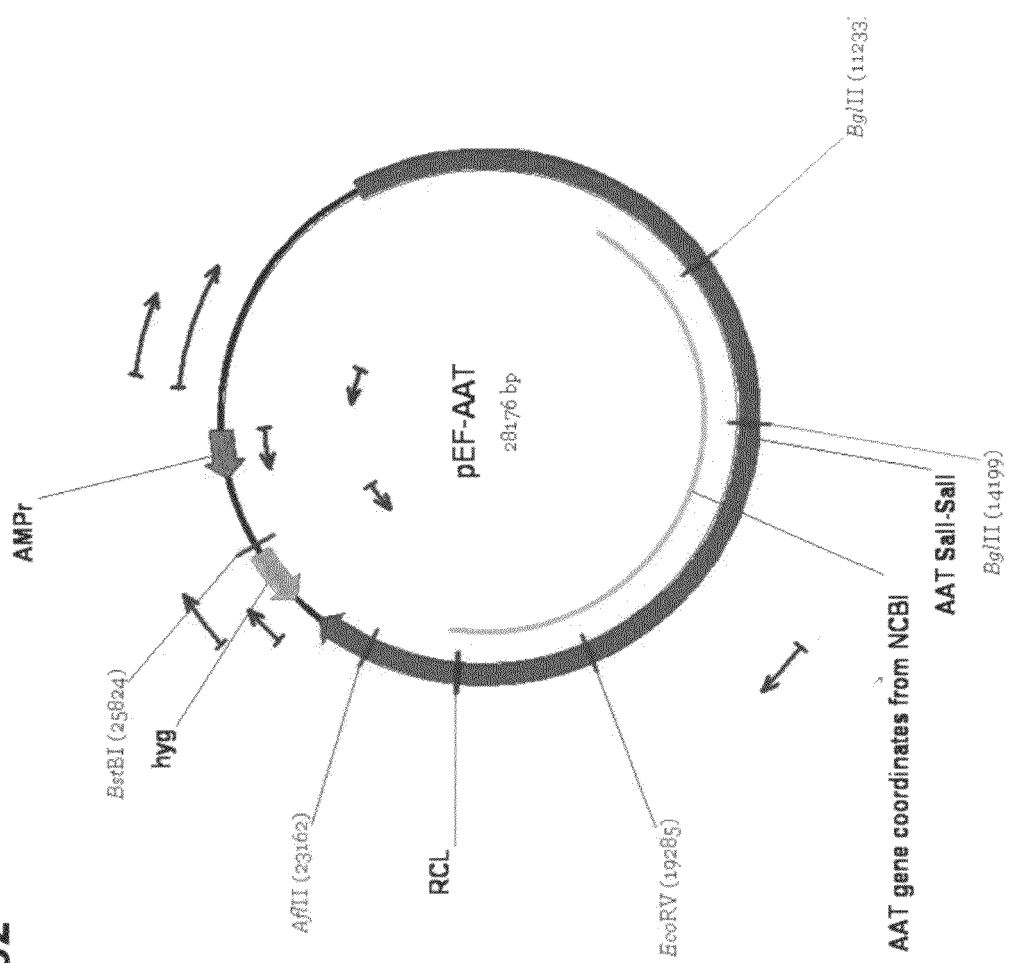
FIG. 32 represents an exemplary construct of certain embodiments of the present invention.

Characteristics of pEF-hAAT. FIG. 32 illustrates one exemplary AAT construct having no significant serine protease inhibitor activity. This constructs contains EBV elements, the sequence favors incorporation into hepatocytes. EF elements allow for extra-chromosomal replication without the risk of random integration into the genome. hAAT is contained as a whole gene, including promoter region and introns, improving long-term housing of the element without cDNA-related silencing. A point mutation in pEF-hAAT is set to be introduced at the protease-binding site sequence (reactive center loop, RCL), as shown in FIG. 32. For this purpose the plasmid is initially cut into two smaller fragments; the 6.5 kb fragment contains the RCL sequence and serves as template for point mutation. Upon successful conversion of the sequence to a non-protease inhibiting hAAT, the mutated 6.5 kb fragment sequence is ligated back into the 21.5 kb sequence and the 28.1 kb mutated plasmid (hAATmut) introduced into animals for structure-function analysis.

Figure 33:
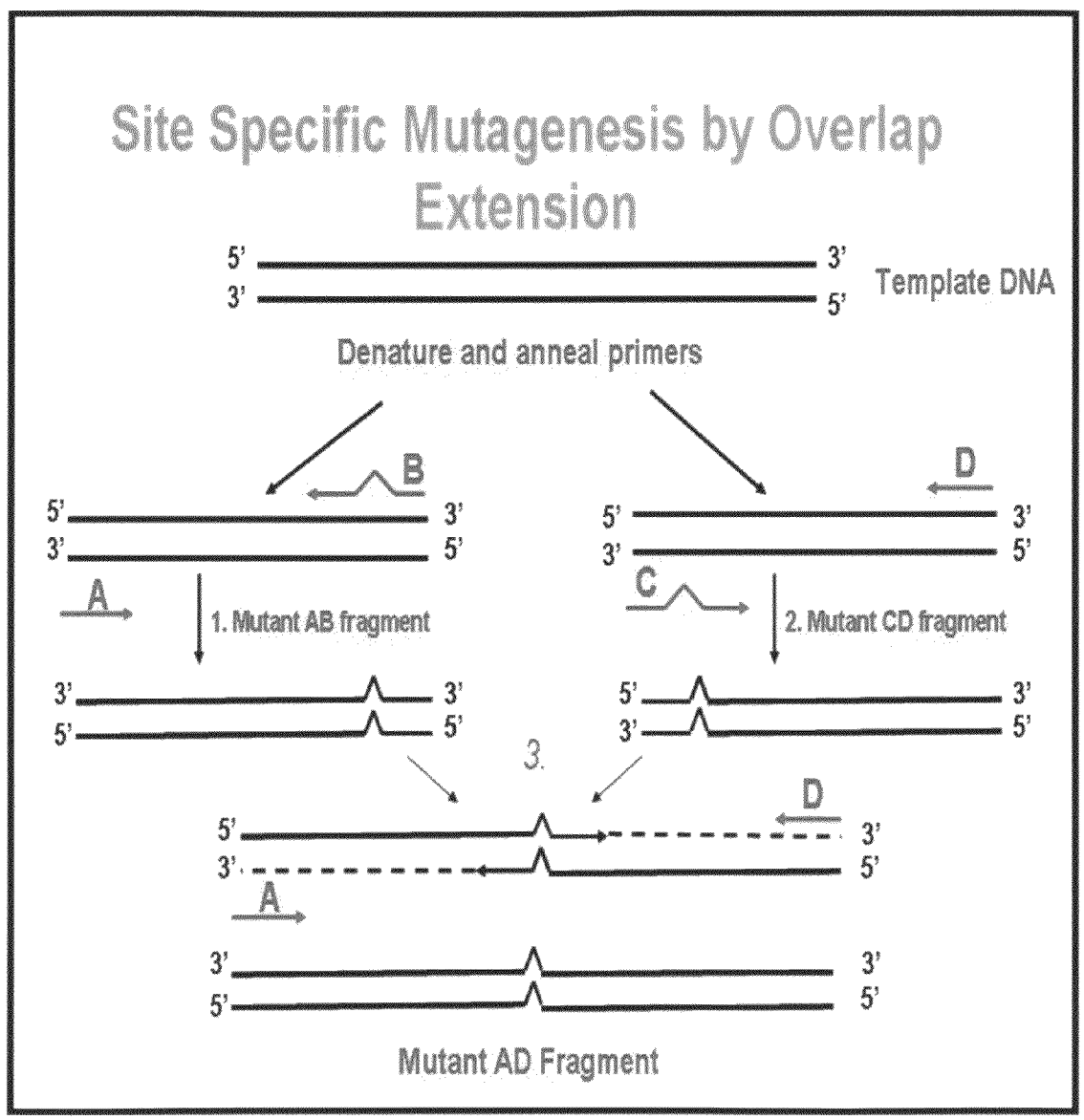
FIG. 33 represents an exemplary protocol for generating a mutant of certain embodiments of the present invention.

FIG. 33 illustrates an example strategy for plasmid point mutation. This exemplary technique involves the design of four PCR primers of which two that overlap contain the desired mutation. The process is performed on a fragment of the original plasmid which is subsequently re-introduced into the cleaved plasmid and the full sequence restored, containing the new mutated sequence.

Figure 34:
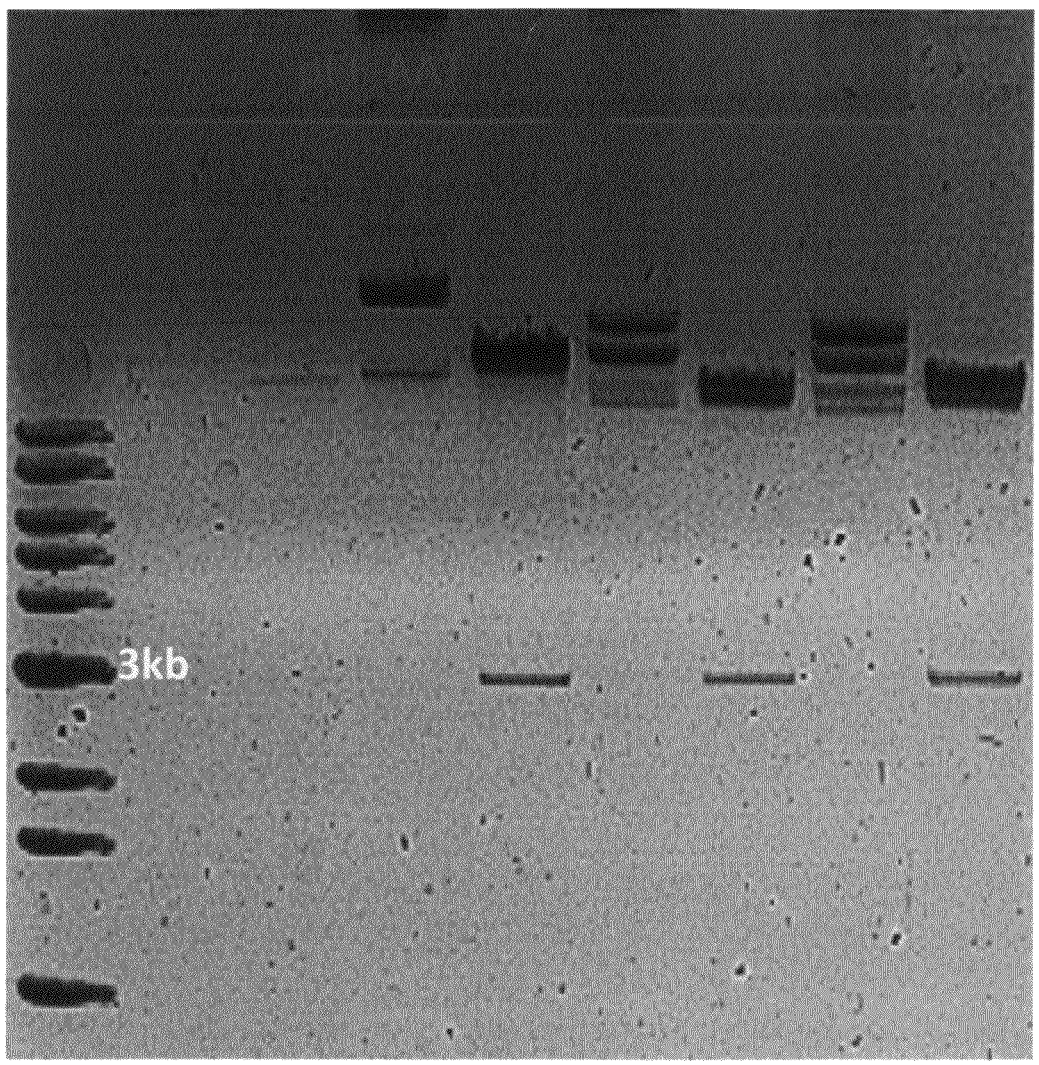
FIG. 34 represents an exemplary gel illustrating different AAT mutants isolated from exemplary protocols of certain embodiments of the present invention.

FIG. 34 illustrates a gel of the plasmid having a point mutation in order to analyze cut versus uncut native and mutated AAT (e.g. pEF-AAT versus PEF-AAT$^{cys}$). Diagnostic specific restriction enzyme analysis confirms the predicted outcome at the end of the ligation process.

Figure 35:
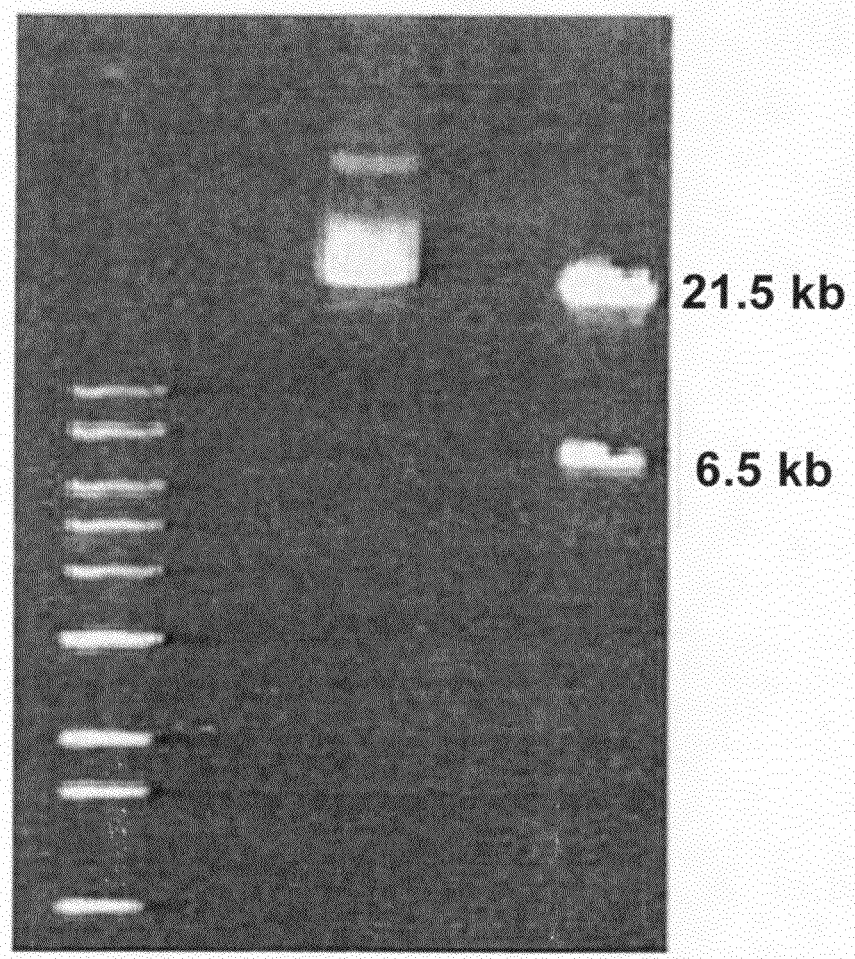
FIG. 35 represents an exemplary gel before and after isolation of an AAT mutant having no significant serine protease inhibitor activity.

FIG. 35 illustrates an exemplary digest of pEF-hAAT and preparation of pEF-hAAT plasmid for mutation and expression in vivo. A 6.5 kb plasmid fragment was excised by restriction enzymes to facilitate point mutation in upcoming experiments. Blue line/frame, the segment containing the protease-binding site sequence (RCL).

FIG. 36 illustrates a portion of the reactive center loop sequences of hAAT compared to a hAAT cysteine mutant, SEQ ID NOs.: 102 and 103.

Example 27

Figure 37:
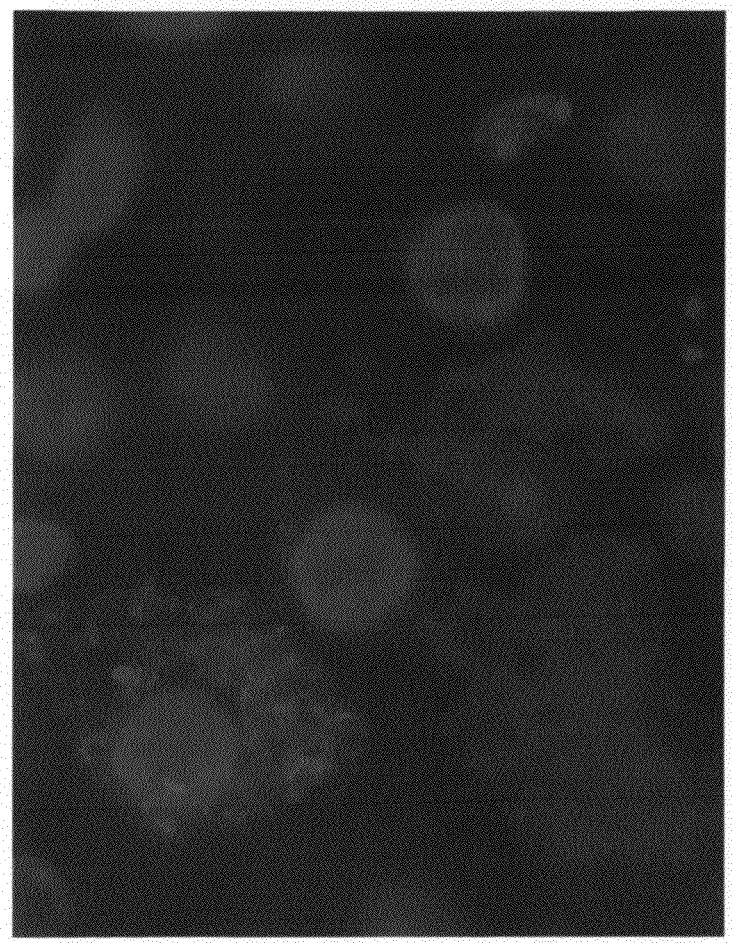
FIG. 37 represents an exemplary photograph of an immunohistochemical analysis of human AAT.

FIG. 37 represents an exemplary photograph of an immunohistochemical analysis illustrating the presence of human AAT.

Figures 38A, 38B, 38C:
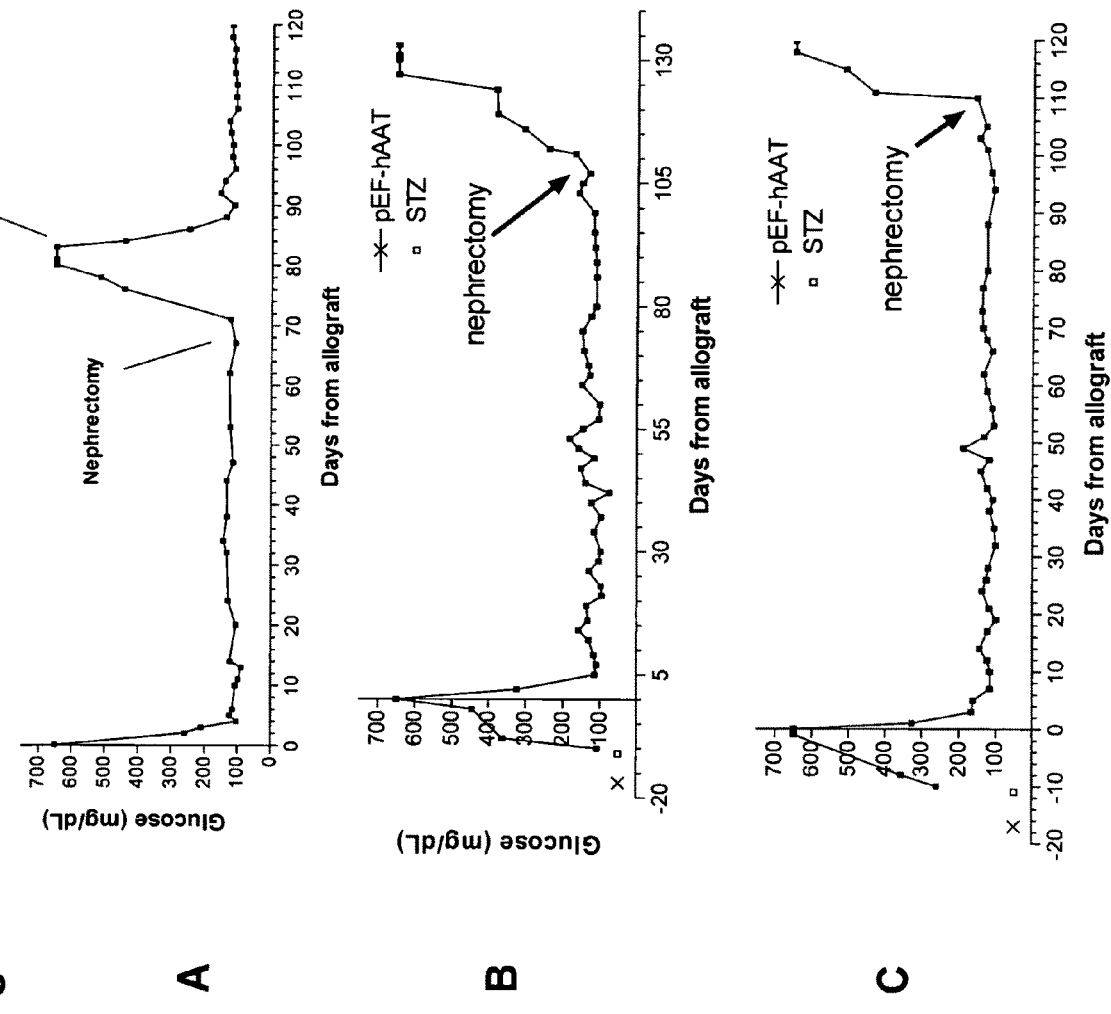
FIGS. 38A-38C represent exemplary plots of glucose produced in an animal model for transplant in the presence or absence of an AAT mutant having no significant serine protease inhibitor activity of certain embodiments of the present invention.
Figures 39A, 39B, 39C, 39D:
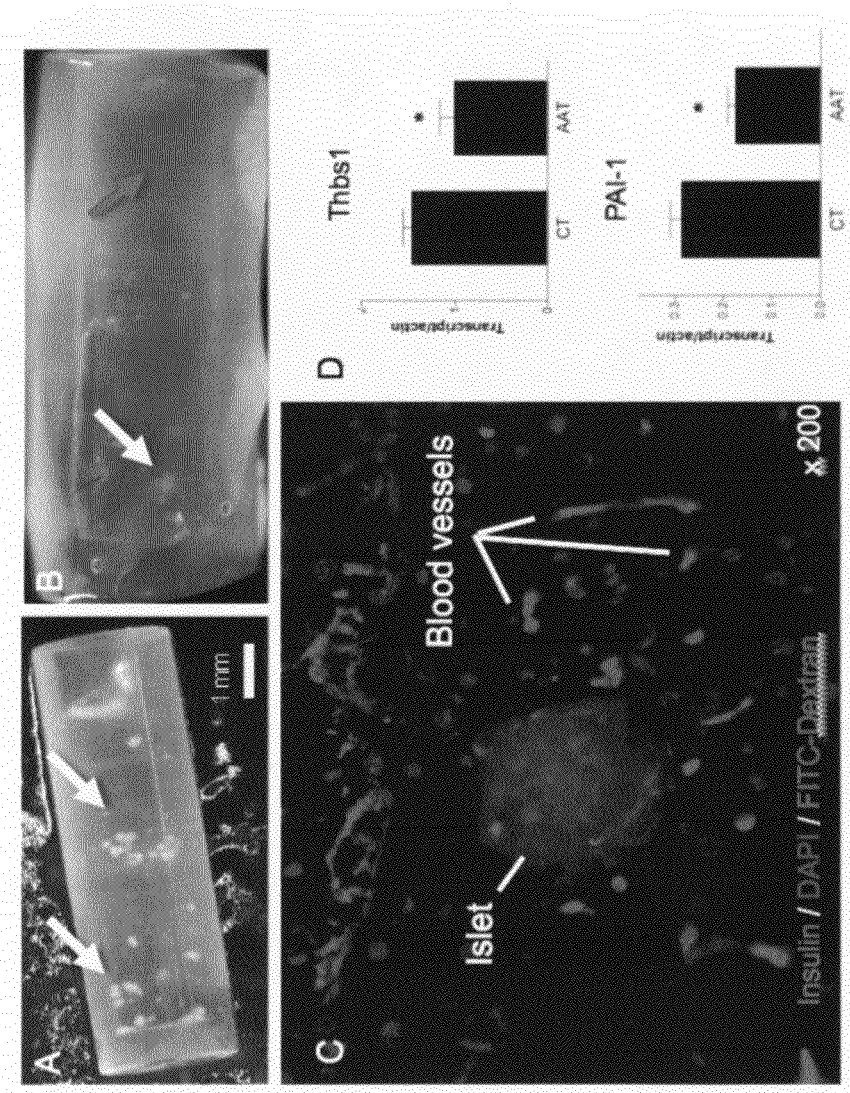
FIGS. 39A-39D represent re-vascularization experiments of some embodiments of the present invention.

FIGS. 38A-38C represent expression of hAAT in mice by introduction of plasmid. 30 days after liver is introduced with 100 micrograms of pEF-hAAT by hydrodynamic injection, human AAT can be demonstrated in mouse hepatocytes. Red, species specific antibodies to hAAT; blue, nuclear stain. FIG. 38A represents effect of plasmid-derived hAAT on islet allograft rejection. FIG. 38B is representative glucose follow-up of diabetic mice that exhibited hAAT serum levels of 1-350 micrograms/ml. FIGS. 38A-38C also illustrate time of nephrectomy, the process of graft removal. One animal was tested for same-strain grafting after regaining hyperglycemia and had accepted the islets.

Example 28

FIGS. 39A-39D represent re-vascularization experiments. A two-millimeter-wide silicone cylinder capsule with a single open end is loaded with twenty islets before engraftment under the skin (39A and 39B). The 'plug' is explanted 9 days after transplantation to examine vessel formation. Blood can be seen in the matrigel compartment. One of the measurements involves perfusion of islets by tail-vein injected FITC-Dextran to directly depict the irrigation of islets by the blood system. Immunohistochemistry of a perfused islet was performed and detected by FITC-dextran (green). Insulin (red), DAPI nuclear background staining (blue); healthy pancreas (39C). RT-PCR of explanted islet grafts depicting two major anti-angiogenic factors was analyzed (39D). In examining possible mechanisms by which AAT may facilitate mature vessel formation, after demonstrating that the pivotal angiogenic factor, VEGF, is elevated by AAT, factors that are detrimental to the formation of vessels were analyzed. Anti-angiogenic factors are reduced in expression intensity in matrigel-grafted islet implants treated by AAT. In vivo hAAT plasmid studies Example 29

Figures 40A, 40B, 40C, 40D, 40E, 40F, 40G:
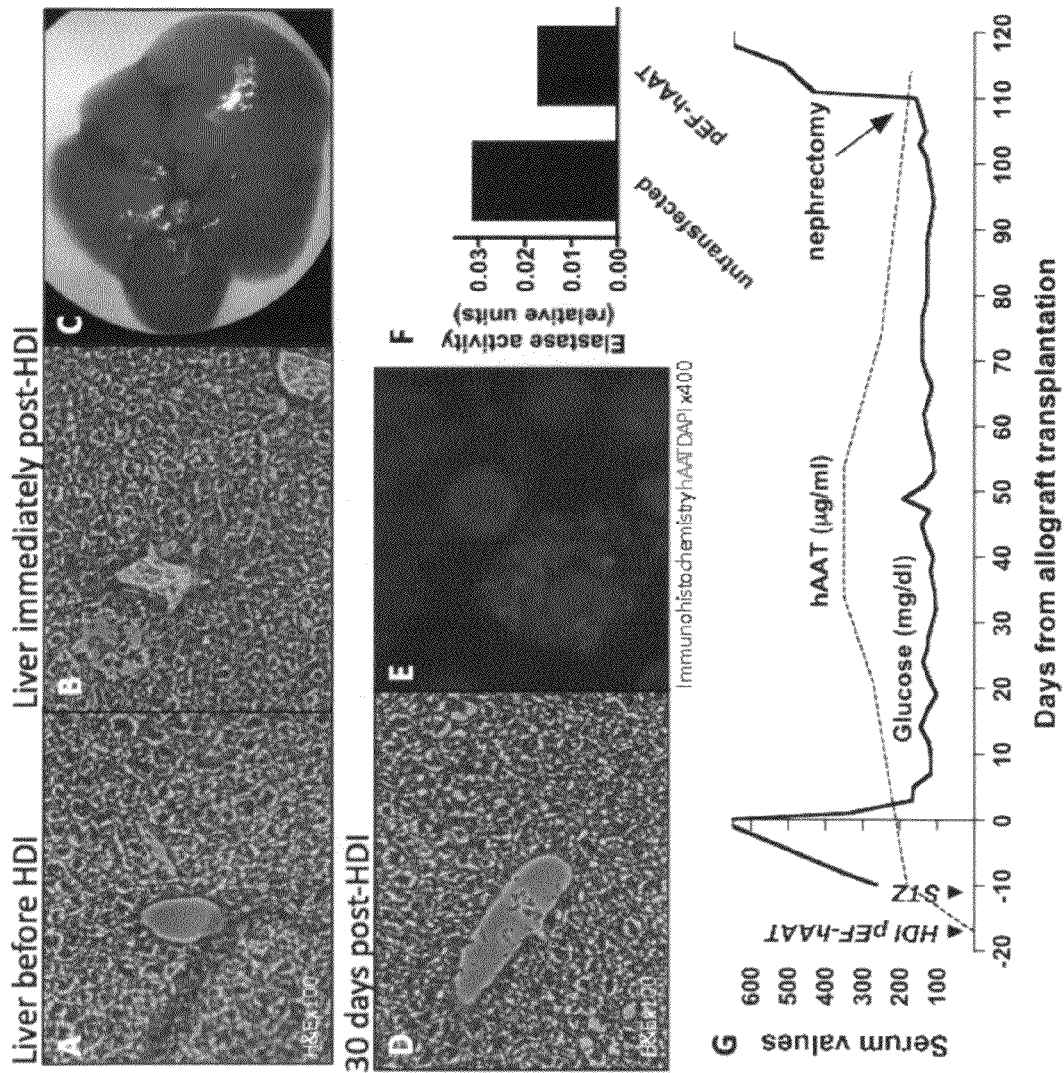
FIGS. 40A-40G represent exemplary data directed to analysis of transplantation in the presence or absence of mutant AAT constructs having no significant serine protease inhibitor activity of certain embodiments of the present invention.

In this study, the 28.1 kb pEF-hAAT plasmid can replace exogenous commercial hAAT. The plasmid was grown in bacteria and pEF-hAAT was purified. The material was introduced to mice in vivo by hydrodynamic tail vein injection (HDI). In the HDI method the plasmid extravasates into the interstitial space of the liver and is uptaken by hepatocytes. Hydrodynamic tail vein injection of plasmid is represented in FIGS. 40A-40D. The procedure achieves expression of foreign genetic material after a rapid injection of soluvle plasmid into the liver. In the first 24 hours liver damage occurs and regeneration initiated, as the plasmid becomes incorporated. The liver damage that occurs from the process (FIGS. 40B-C) results in a 24-hour period of cellular division and repair after which the liver regains its normal architecture (FIG. 40D). The incorporated plasmid produces hAAT protein (FIG. 40E) that contains elastase-inhibiting properties (FIG. 40F) and is released into the circulation (FIG. 40G). Serum levels range from 1 to 350 µg/ml as the efficiency of the procedure is highly variable. In these preliminary studies, all mice that were introduced with the plasmid and that produced hAAT (n 6) were rendered hyperglycemic by single streptozotocin injection and were grafted with allogeneic islets (FIG. 40G). In all recipients, glucose levels were corrected and grafts were accepted. In 1 out of 6 mice progressive liver damage developed and ascites was evident about the time that the islet graft exhibited signs of failure (day 28, not shown). The development of ascites is easily detectable in mice by virtue of prompt rise in body weight due to the accumulation of abdominal fluid; therefore, the experimental set-up was adjusted to have the plasmid introduced at least 14 days prior to continuation of the study in the individual animal, at which time liver damage is excluded.

Example 30

FIGS. 40A-40G represent protection of islet allografts using pEF-hAAT plasmid expression in vivo. (A) Normal liver. (B) Damaged liver exhibiting microscopic disruption of cellular architecture immediately after introduction of pEF-hAAT by hydrodynamic tail vein injection (100 µg plasmid in a volume of 1.8 ml, injected in 6 seconds). (C) Edematic lesions observed macroscopically (entire liver). (D) 30 days after HDI the liver regains normal architecture. (E) Immunohistochemistry staining for hAAT in pEF-AAT HDI liver, representative image from 8 mice. (F) Anti-elastase activity in supernatant of Hepalc cells expressing pEF-hAAT and containing hAAT at 213±12 pg/ml. (G) Normoglycemia is sustained upon transplantation of allogeneic islets until elective graft removal by nephrectomy, (n=6, representative glucose follow-up). Continuous line: glucose monitoring, dashed line: circulating hAAT levels.

Figure 41:
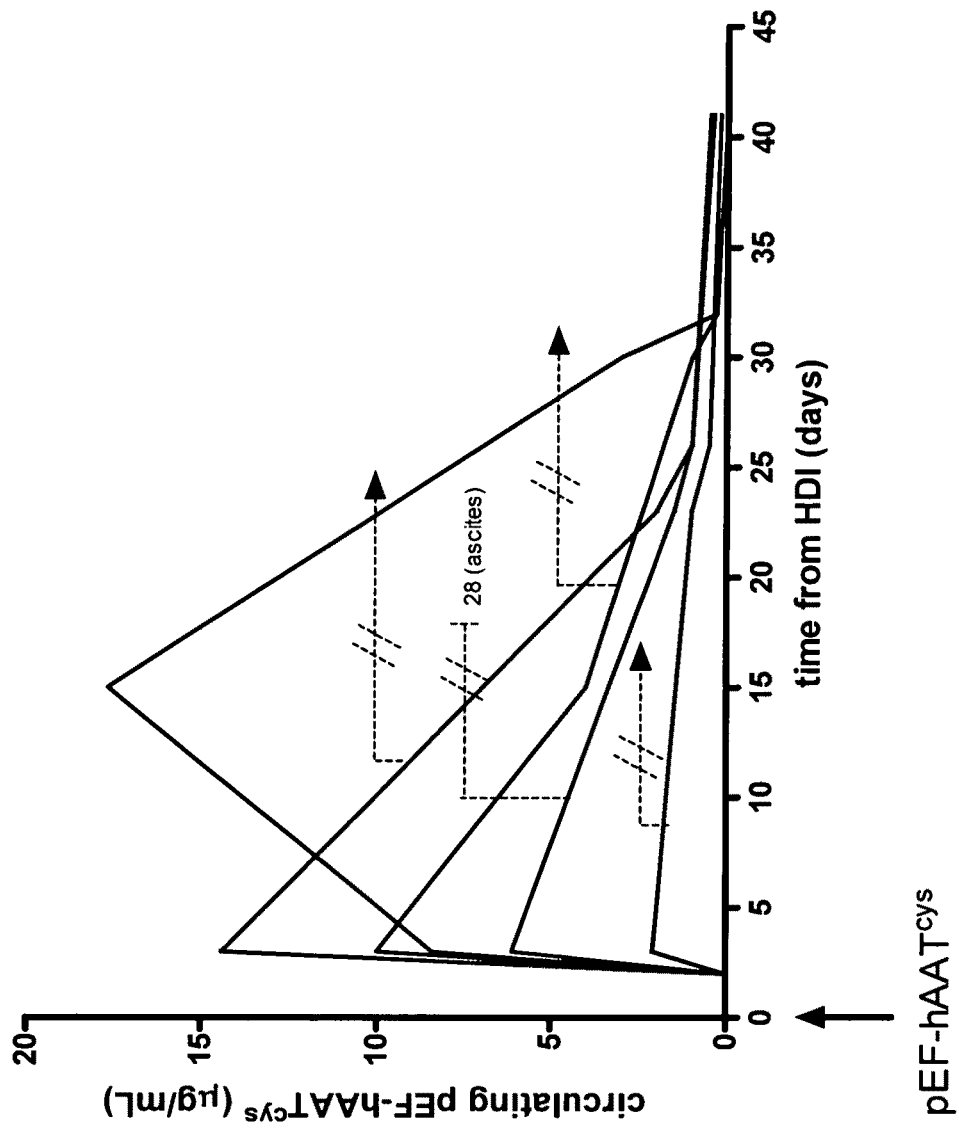
FIG. 41 represents an exemplary graph analysis of presence or absence of mutant AAT molecules isolated and measured in a transplant mouse model of certain embodiments of the present invention.

FIG. 41 illustrates serum levels of mutated hAAT. pEF-hAATcys levels exhibit a comparable circulating profile to that which is achieved by native pEF-hAAT. Four animals were rendered diabetic (point of merge between vertical dashed line and continuous line per individual case). The mice were then grafted with allogeneic islets. Dashed arrows, islet transplantation procedure; Black arrow-head, indefinite graft acceptance.

Figures 42A, 42B, 42C, 42D:
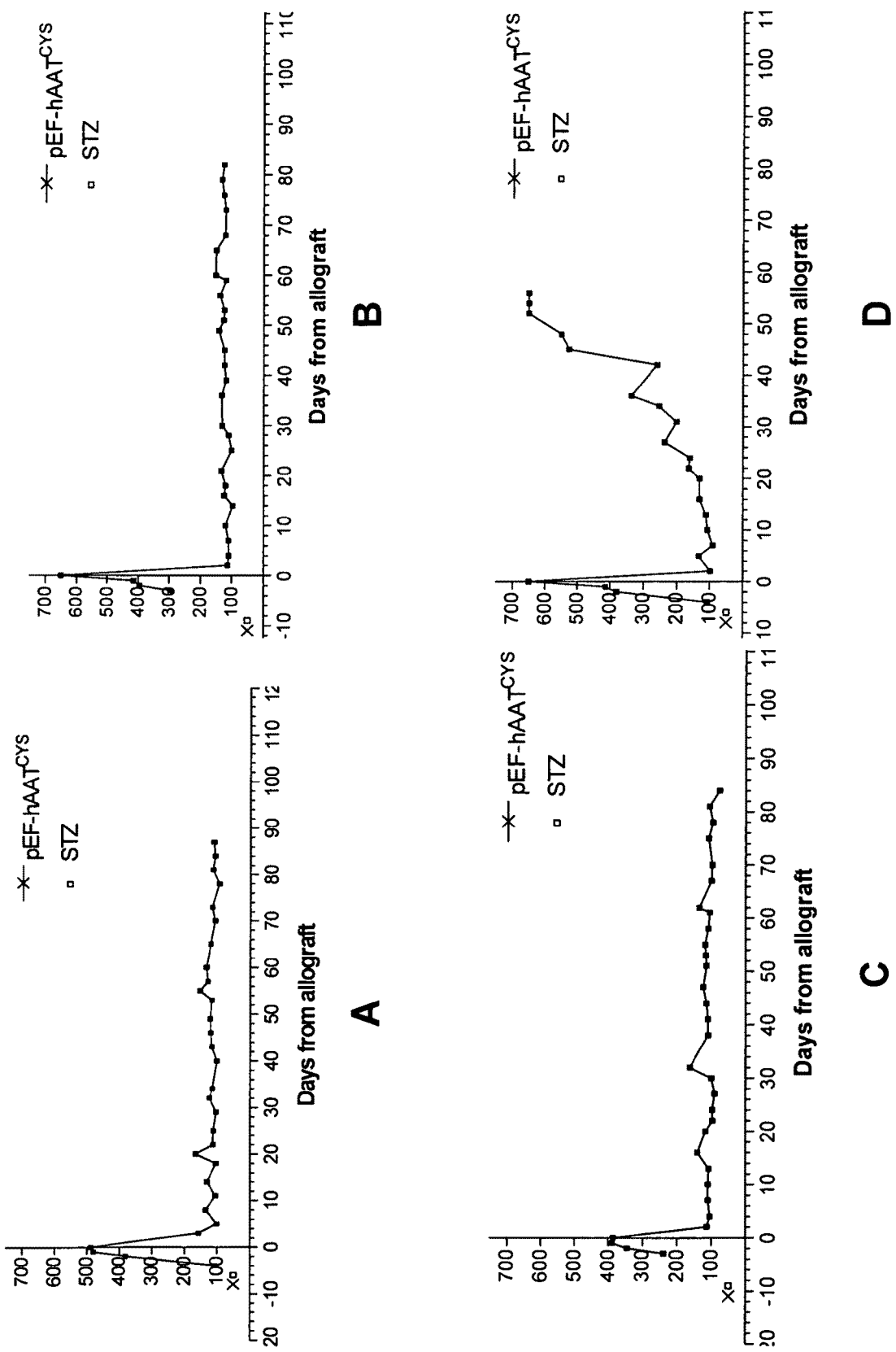
FIGS. 42A-42D represent exemplary plots of allografts in the presence of a human AAT mutant of certain embodiments of the present invention.

FIGS. 42A-42B illustrate days after allograft in a mouse model in the presence of pEF-hAATcys. It was demonstrated that a mutant hAAT having no significant serine protease inhibitor activity protected the allographs in an acceptable mouse model.

All of the COMPOSITIONS and METHODS disclosed and claimed herein may be made and executed without undue experimentation in light of the present disclosure. While the COMPOSITIONS and METHODS have been described in terms of preferred embodiments, it will be apparent to those of skill in the art that variation may be applied to the COM POSITIONS and METHODS and in the steps or in the sequence of steps of the METHODS described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed:

1. A pharmaceutical composition comprising: mutated human alpha-1 antitrypsin (AAT) wherein the mutated AAT comprises AAT with one or more mutations at one or more of residues 356-361 of SEQ ID NO: 61 wherein the mutations comprise a proline to cysteine substitution at position 357 or an alanine, glycine, arginine, leucine and asparagine substitution at corresponding positions 356-358, 360 and 361 respectively of SEQ ID NO: 61; and the one or more mutations significantly reduces or eliminates serine protease inhibition activity of the mutated AAT compared to a control human AAT; and a pharmaceutically acceptable excipient.

2. The pharmaceutical composition of claim 1, wherein the one or more mutations are introduced by site-directed mutagenesis.

3. The pharmaceutical composition of claim 1, further comprising an agent selected from the group consisting of an anti-inflammatory agent, an immunosuppressive agent, an immunomodulatory agent, an anti-microbial agent, an anti-viral agent, an anti-bacterial agent, an anti-fungal agent, an anti-parasitic agent or any combination thereof.

4. The pharmaceutical composition of claim 1, further comprising an immunosuppressive agent.

5. A kit comprising: a composition of claim 1; and at least one container.

6. The kit of claim 5, further comprising an agent selected from the group consisting of an anti-inflammatory agent, an immunosuppressive agent, an immunomodulatory agent, an anti-microbial agent, an anti-viral agent, an anti-bacterial agent, an anti-fungal agent, an anti-parasitic agent or any combination thereof.

7. The pharmaceutical composition of claim 1, wherein a protease-binding site within the mutated AAT's reactive center loop (RCL) remains intact.

8. The pharmaceutical composition of claim 1, wherein the mutated AAT is hAAT$^{cys}$ having a mutation at amino acid residue 357 of SEQ ID NO: 61 where proline is mutated to cysteine.

9. The pharmaceutical composition of claim 1, wherein the mutated AAT is part of a fusion polypeptide and wherein the fusion polypeptide comprises mutated AAT fused to an immunoglobulin constant region.

10. The pharmaceutical composition of claim 9, wherein the immunoglobulin constant region is a human IgG1 constant region.

\* \* \* \* \*